(12) United States Patent
Chater et al.

(10) Patent No.: US 7,316,914 B2
(45) Date of Patent: Jan. 8, 2008

(54) METHODS AND MATERIALS RELATING TO GENE EXPRESSION

(75) Inventors: Keith Frederick Chater, Norwich (GB); Celia Joyce Bruton, Norwich (GB); Sean Joseph O'Rourke, Cork (IE); Andreas Wilhelm Wietzorrek, Bodelshausen (DE)

(73) Assignee: Plant Bioscience Limited, Norwick, Norfolk (GB)

( * ) Notice: Subject to any disclaimer, the term of this patent is extended or adjusted under 35 U.S.C. 154(b) by 560 days.

(21) Appl. No.: 10/168,663

(22) PCT Filed: Dec. 20, 2000

(86) PCT No.: PCT/GB00/04972

§ 371 (c)(1),
(2), (4) Date: Oct. 25, 2002

(87) PCT Pub. No.: WO01/48228

PCT Pub. Date: Jul. 5, 2001

(65) Prior Publication Data

US 2004/0086962 A1    May 6, 2004

(30) Foreign Application Priority Data

Dec. 23, 1999  (GB) .................................. 9930477.6

(51) Int. Cl.
*C12P 21/02*    (2006.01)

(52) U.S. Cl. ................... 435/69.1; 435/320.1; 536/24.1

(58) Field of Classification Search ..................... None
See application file for complete search history.

(56) References Cited

OTHER PUBLICATIONS

Chater et al. EMBO. 1985; 4:1893-5.*
Neal et al. Gene. 1987; 58:229-41.*
Redenbach et al. J. Bact. 1998; 180:2796-99.*
Richards, F.M., 1997, Cell Mol. Life Sci 53:790-802.*
Holstege et al., 2006, Cell 124: 21-23.*
Onaka et al., 1997, J. Bacteriol. 179, 8: 2748-2752.*
Aguilar A., Hopwood D. A. (1982) J. Gen. Microbiol 128: 1893-1901 "Determination of methylenomycin A synthesis by the pSV1 plasmid from *Streptomyces* violaceus-ruber SANK 95570".
Alvarez, M. A., Chater K. F., Rodicio M. R. (1993) Mol. Microbiol. 8: 243-252 "Complex transcription of an operon encoding the Sall restriction-modification system of *Steptomyces albus G*".
Bruton, C. J., Guthrie E. P., Chater K. F. (1991) Bio/Technology 9: 652-656 "Phage vectors that allow monitoring of transcription of secondary metabolism genes in *Streptomyces*".
Bruton C. J., Chater K. F. (1987) Nucl Acids Res 15: 7053-7065 "Nucleotide sequence of IS110, an insertion sequence of *Streptomyces coelicolor* A3(2)".
Database NCBI Accession No. AJ276673 Brutin C J (2000) "*Streptomyces coelicolor* partial SCP1 plasmid including genes for methylenomycin biosynthesisl" XP002165370.
Bruton C., Woodburn L., Angel S., Chater K. (1990) 6th International Symposium on Genetics of Industrial Microorganisms GIM90 Abstract Book: Abstract A41 Strasbourg Palais des Congres Aug. 12-18, 1990 " Structure and regulation of the methylenomycin biosynthetic genes of *Streptomyces coelicolor* A3(2)".
Caffrey P, Bevitt D J, Staunton J, Leadlay P F (1992) FEBS Let. 304: 225-228. "Identification of DEBS1, DEBS2 and DEBS3, the multienzyme polypeptides of the erythromycin-producing polyketide synthase from *Saccharopolyspora erythraea*".
Chater, K. F., Bruton C. J., King A. A., Saurez J. E. (1982) Gene 19: 21-23. "The expression of *Streptomyces* and *Escherichia coli* drug resistance determinants cloned into the *Streptomyces* phage ΦC31".
Chater, K. F., Bruton C. J. (1983) Gene 26: 67-78. "Mutational cloning in *Streptomyces* and the isolation of antibiotic production genes".
Chater, K. F. and C. J. Bruton. (1985) EMBO J. 4: 1893-1897 "Resistance, regulatory and production genes for the antibiotic methylenomycin are clustered".
Chater, K. F. (1990) Bio/Technology 8: 115-121 "The improving prospects for yield increase by genetic engineering in antibiotic-producing *streptomycetes*".
Fernandez-Moreno, M. A. (1991) Cell 66: 769-780. "The act cluster contains regulatory and antibiotic export genes, direct targets for control by the bldA tRNA gene of *Streptomyces*".
Fisher S. H., Bruton C. J., Chater K. F. (1987) Mol. Gen. Genet. 206: 35-44. "The glucose kinase gene of *Streptomyces coelicolor* and its use in selecting spontaneous deletions for desired regions of the genome".
Guilfoile P G et al (1992) J. Bacteriol. 174(11): 3651-3658 "Sequence and Transcriptional Analysis of the *Streptomyces glaucescens* tcmAR Tetracenomycin C resistance and repressor gene Loci".
Guthrie, E. P., Chater K. F (1990) J. Bacteriol. 172 : 6189-6193 "The level of a transcript required for production of a *Streptomyces coelicolor* antibiotic is conditionally dependent on a tRNA gene".
Hillen W., Berens C. (1994) Annu. Rev. Microbiol. 48 : 345-369 "Mechanisms underlying expression of Tn10 encoded tetracycline resistance".
Hobbs, G., Obanye A. I. C., Petty J., Masson J. C., Barratt E., Gardner D. C. J., Flett F., Smith C. P., Broda P., Oliver S. G. (1992) J. Bacteriol. 174: 1487-1494 "An integrated approach to studying regulation of production of the antibiotic methylenomycin by *Streptomyces coelicolor* A3 (2)".
Hopwood, D. A. (1997) Chem. Rev. 97: 2465-2497. "Genetic contributions to understanding polyketide synthases".
Horinouchi, S., H. Suzuki, M. Nishiyama and T. Beppu. (1989) J. Bacteriol. 171: 1206-1210 "Nucleotide sequence and transcriptional analysis of the *Streptomyces griseus* gene (afsA) responsible for A-factor biosynthesis".
Horinouchi S., Kumada Y., Beppu T. (1984) J. Bacteriol. 158: 481-487 "Unstable genetic determinant of A-factor biosynthesis in *streptomycin*-producing organisms: cloning and characterization".

(Continued)

*Primary Examiner*—James Ketter
(74) *Attorney, Agent, or Firm*—Dann Dorfman Herrell and Skillman; Patrick J. Hagan, Esq.

(57) ABSTRACT

An expression cassette for expressing a nucleic acid of interest derived from the regulatory region of the methylenomycin gene cluster of the SCP1 plasmid of *Streptomyces coelicolor* A3(2), and related materials and methods.

50 Claims, 29 Drawing Sheets

OTHER PUBLICATIONS

Hornemann, U., Hopwood D. A. (1978) Tetrahed. Lett. 33:2977-2978 Isolation and characterization of desepoxy-4,5-didehydro-methylenomycin A, a precursor of the antibiotic methylenomycin A in SCP1+ strains of *Streptomyces coelicolor* A3 (2).

Ingram C., Brawner M., Youngman P., Westpheling J. (1989) J. Bacteriol. 171: 6617-6624 "xylE functions as an efficient reporter gene in *Streptomyces* spp.: use for the study of galP1, a catabolite-controlled promoter".

Janssen, G. R., Bibb M. J. (1993) Gene 124: 133-134. "Derivatives of pUC18 that have *Bgl*II sites flanking a modified multiple cloning site and that retain the ability to identify recombinant clones by visual screening of *Escherichia coli* colonies".

Kirby, R., Hopwood D. A. (1977) J. Gen. Microbiol. 98: 239-252 "Genetic determination of methylenomycin synthesis by the SCP1 plasmid of *Streptomyces coelicolor* A3 (2)".

Kirby R., Wright L. F., Hopwood D. A. (1975) Nature 254: 265-267. "Plasmid-determined antibiotic synthesis and resistance in *Streptomyces coelicolor*".

Lawlor E. J. (1987) PhD Thesis, University of Easr Anglia, UK "Molecular Genetics of bldA, a developmental gene of *Streptomyces coelicolor*".

Leskiw B., Guthrie E., Lawlor E., Daly B., Chater K. (1990) 6th International Symposium on Genetics of Industrial Microorganisms GIM90 Abstract Book: Abstract A43 Strasbourg Palais des Congres Aug. 12-18, 1990 "Differentiation and antibiotic production in *Streptomyces coelicolor* are regulated by a tRNA for a very rare codon".

Leskiw B. K., Lawlor E. J., Fernandez-Abalos J. M. and Chater K. F. (1991) Proc. Natl. Acad. Sci. USA 88: 2461-2465. "TTA codons in some genes prevent their expression in a class of developmental, antibiotic-negative *Streptomyces* mutants".

MacNeil D. J., Gewain K. M., Ruby C. L., Dezeny G., Gibbons P. H., MacNeil T. (1992) Gene 111: 61-68. "Analysis of *Streptomyces avermitilis* genes required for avermectin biosynthesis utilizing a novel integration vector".

DATABASE EMBL (1998) Accession No. AF072887 Moore R. A., DeShazer D., Reckseidler S., Weissman A., Woods D. E. "*Burkholderia pseudomallei* regulator AmrR (amrR), putative membrane fusion protein AmrA (amrA), and putative transporter AmrB (amrB) genes, complete cds".

Nakano H., Takehara E., Nihira T., Yamada Y. (1998) J. Bacteriol. 180: 3317-3322 "Gene replacement analysis of the *Streptomyces virginiae* barA gene encoding the butyrolactone autoregulator receptor reveals that BarA acts as a repressor in virginiamycin biosynthesis".

Neal R. J., Chater K. F. (1987) Gene 58: 229-241. "Nucleotide sequence analysis reveals similarities between protein determining methylenomycin A resistance in *Streptomyces* and tetracycline resistance in *eubacteria*".

Onaka H., Horinouchi S. (1997) Mol. Microbiol. 24: 991-1000. "DNA-binding activity of the A-factor receptor protein and its recognition DNA sequences".

Onaka H., Sugiyama M., Horinouchi S. (1997) J. Bacteriol. 179: 2748-2752. "A mutation at proline-115 in the A-factor receptor protein of *Streptomyces griseus* abolishes DNA-binding ability but not ligand-binding ability".

Onaka H., Nakagawa T., Horinouchi S. 1998 Mol. Microbiol. 28: 743-753. "Involvement of two A-factor receptor homologues in *Streptomyces coelicolor* A3 (2) in the regulation of secondary metabolism and morphogenesis".

Onaka H., Ando N., Nihira T., Yamada Y., Beppu T., Horinouchi S. (1995) J. Bacteriol. 177: 6083-6092. "Cloning and characterization of the A-factor receptor gene from *Streptomyces griseus*".

DATABASE EMBL (1998) Accession No. AB000385 Onaka H., Horinouchi S. "*Streptomyces coelicolor* gene from CprB, complete cds."

Ranganathan A., Timoney M., Bycroft M., Cortes J., Thomas I. P., Wilkinson B., Kellenberger L., Hanefeld U., Galloway I. S., Staunton J. and Leadlay P. F. (1999) Chem & Biol. 6: 731-741. "Knowledge-based design of bimodular and trimodular polyketide synthases based on domain and module swaps: a route to simple statin analogues".

Redenbach M et al., (1998) J Bacteriol. 180(10): 2796-2799 "Cloning and physical mapping of the EcoRI fragments of the giant linear plasmid SCP1".

Rodicio M. R., Chater K. F. (1988) Mol. Gen. Genet. 213: 346-353 "Cloning and expression of the *Sal*I restriction-modification genes of *Streptomyces albus* G".

Sugiyama M., Onaka H., Nakagawa T., Horinouchi S. (1998) Gene 222: 133-144. "Site-directed mutagenesis of the A-factor receptor protein: Val-41 important for DNA-binding and Trp-119 important for ligand-binding".

Tan H., Chater K. F. (1993) J. Bacteriol. 175: 933-940. "Two developmentally controlled promoters of *Streptomyces coelicolor* A3 (2) that resemble the major class of motility-related promoters in other bacteria".

White J., Bibb, M. (1997) J. Bacteriol. 179: 627-633 "bldA dependence of undecylprodigiosin production in *Streptomyces coelicolor* A3 (2) involves a pathway-specific regulatory cascade".

Zukowski M. M., Gaffney D. F., Speck D., Kauffmann M., Findeli A., Wisecup A., Lecocq J. P. (1983) Proc. Natl. Acad. Sci USA 80: 1101-1105. "Chromogenic identification of genetic regulatory signals in *Bacillus subtilis* based on expression of a cloned Pseudomonas gene".

Keith F. Chater et al., "The evolution of development in *Streptomyces* analysed by genome comparisons", FEMS Microbiol Rev., 30: 651-672 (2006).

Keith F. Chater, "*Streptomyces* inside-out: a new perspective on the bacteria that provide us with antibiotics", Phil. Trans. R. Soc. B, 361: 761-768 (2006).

S.D. Bentley et al., "SCP1, a 356 023 bp linear plasmid adapted to the ecology and developmental biology of its host . . . ", Molecular Microbiology, 51(6): 1615-28 (2004).

\* cited by examiner

Fig. 1.
(a) The genome of streptomyces coelicolor A3(2)
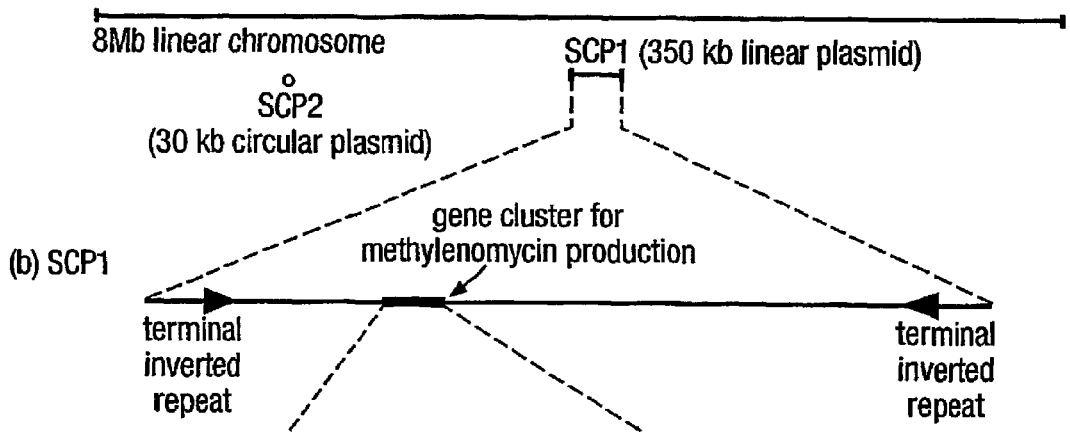
(c) Gene cluster for methylenomycin biosynthesis
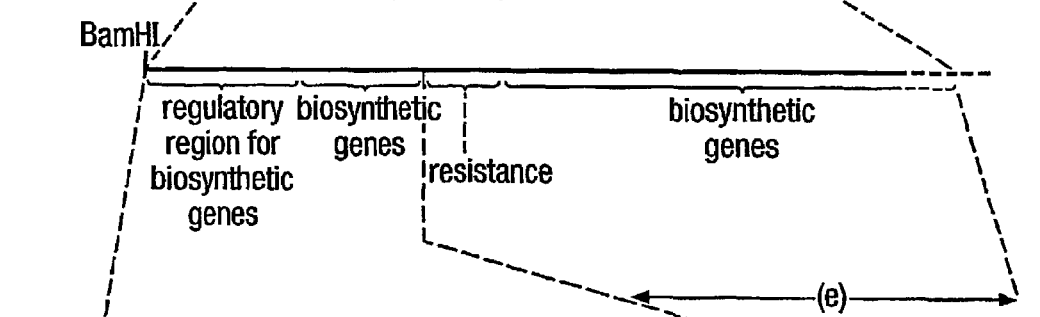
(d) "Regulatory portion"
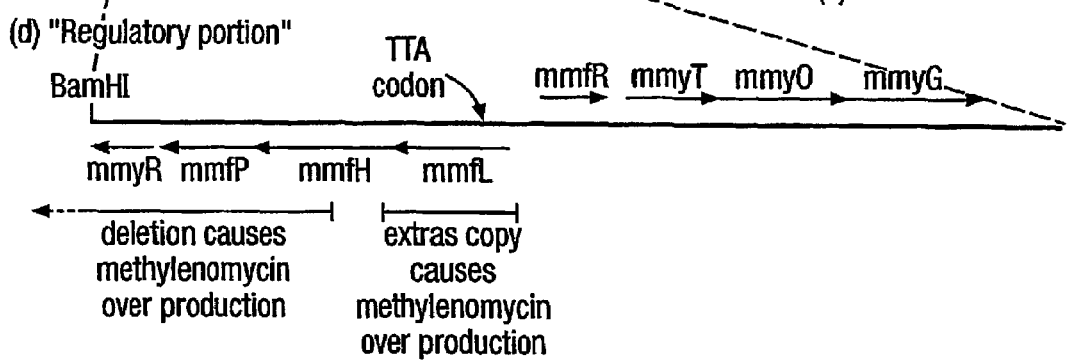
(e) Location of mmyB
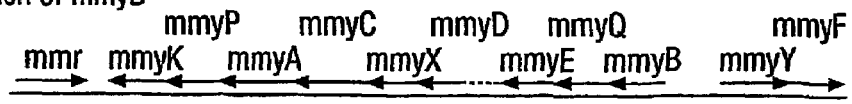

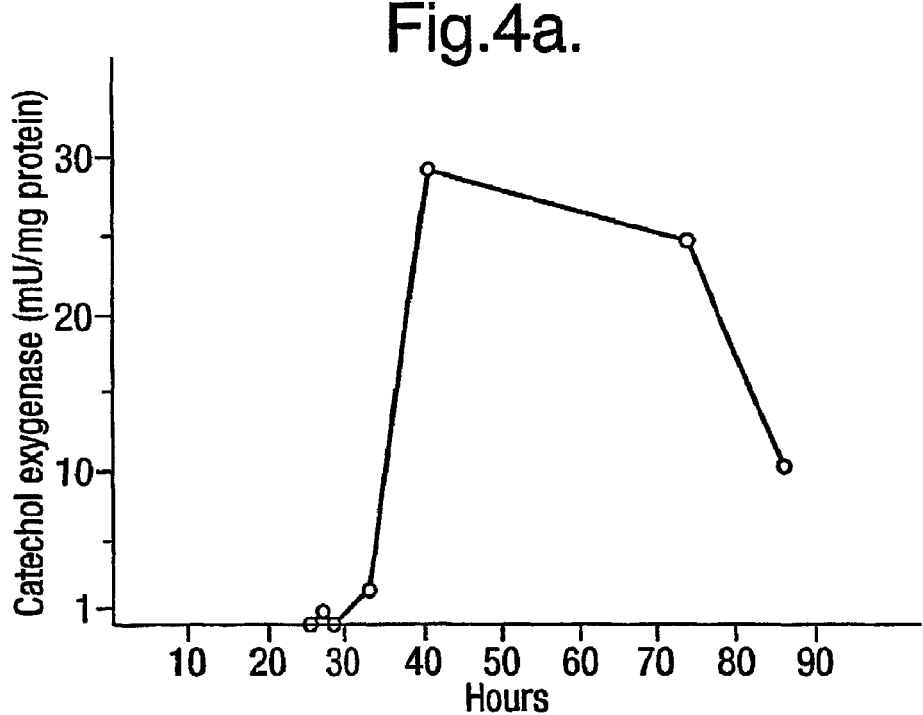
Fig.4a.
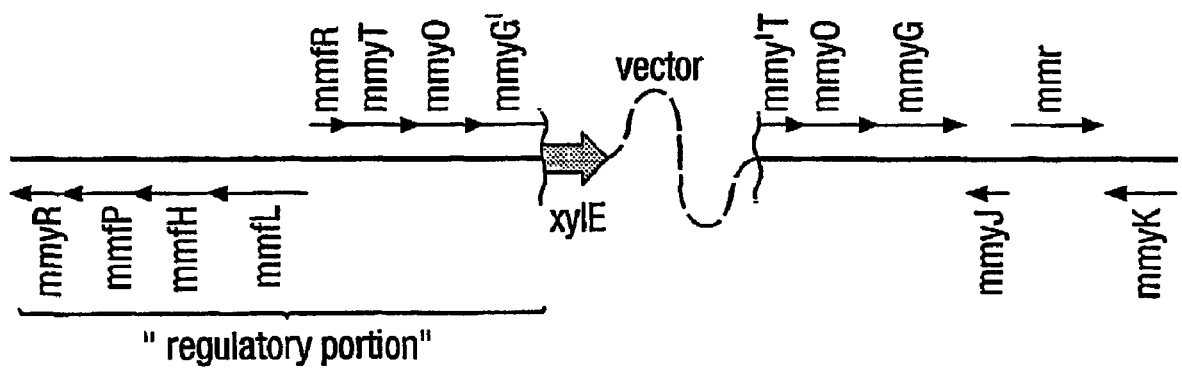

Fig.4b.
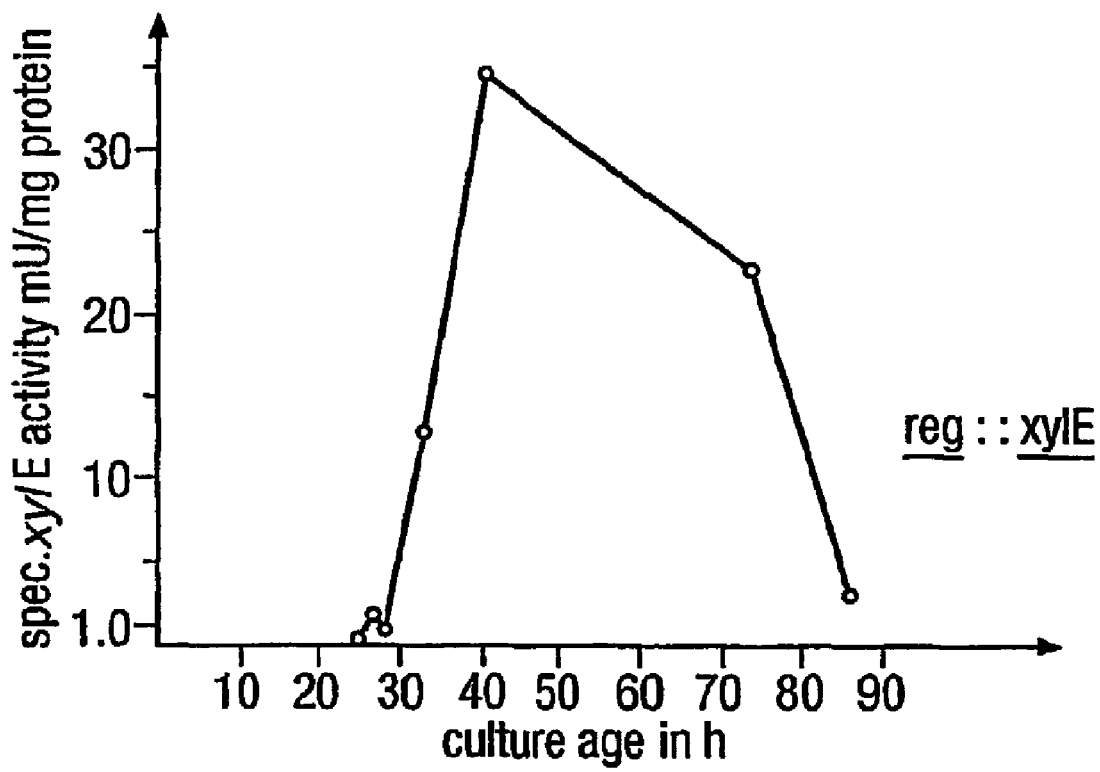
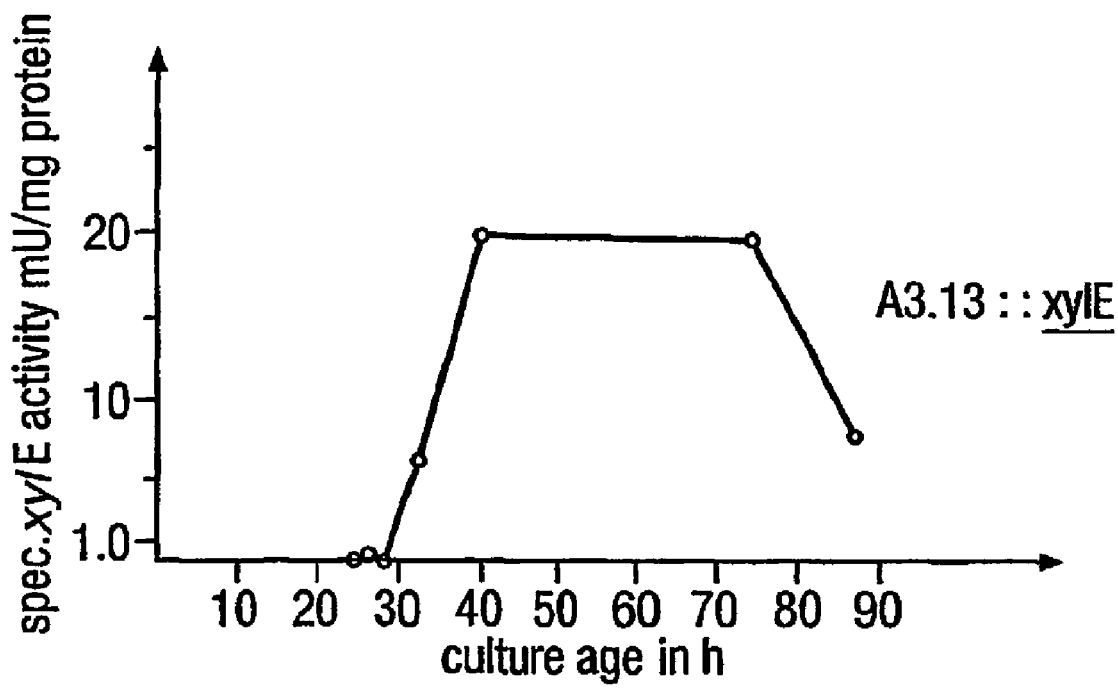

Fig.7.

```
XhoI
 |
      CTCGAGACATGGCTGGCATCGAGGTCGACGACACCACTGCGGACGAGCTGCGGGCCCTGG
  1   ------------+---------+---------+---------+---------+---------+  60
      GAGCTCTGTACCGACCGTAGCTCCAGCTGCTGTGGTGACGCCTGCTCGACGCCCGGGACC

CCGACGCGGCCGGGCTGCCGCTGGACGCCTACCTCGCGCAGGTCGCCGAGGAGAAGCGGC
 61   ------------+---------+---------+---------+---------+---------+ 120
      GGCTGCGCCGGCCCGACGGCGACCTGCGGATGGAGCGCGTCCAGCGGCTCCTCTTCGCCG

GCGAGCGCGCTGGCCGAGGGCGCGGAGATCTTCCGCCGGGTCACCGGCACCCCGGAGA
121   ------------+---------+---------+---------+---------+---------+ 180
      CGCTCGCGCGACCGGCTCCCGCGCCTCTAGAAGGCGGCCCAGTGGCCGTGGGGCCTCT

CCGTCGCCGCCTTCGACGCGGAGTACGGCGGCCCCGCGCAGGCGCAGACCGCCCCGCGGG
181   ------------+---------+---------+---------+---------+---------+ 240
      GGCAGCGGCGGAAGCTGCGCCTCATGCCGCCGGGGCGCGTCCGCGTCTGGCGGGCGCCC

CGGCCTGACCTGTGCCTGCCGAGTACTACGTCGACTACCGGTGGTTCCTGGAGCGCCAGG
241   ------------+---------+---------+---------+---------+---------+ 300
      GCCGGACTGGACACGGACGGCTCATGATGCAGCTGATGGCCACCAAGGACCTCGCGGTCC

CCGAGCTGCTGGACGATCTCGCGGTCAGCGACTACTCCGTCTTCGTCGGCCTAGCCGCCC
301   ------------+---------+---------+---------+---------+---------+ 360
      GGCTCGACGACCTGCTAGAGCGCCAGTCGCTGATGAGGCAGAAGCAGCCGGATCGGCGGG

GGCACAGGGTCGACCCGCCCCGTCACGACCAGCATCACCCGGACGCCTTCTGGCGGGCGG
361   ------------+---------+---------+---------+---------+---------+ 420
      CCGTGTCCCAGCTGGGCGGGGCAGTGCTGGTCGTAGTGGGCCTGCGGAAGACCGCCCGCC

CCGTGATGCTGGAGGAGTGCGTCGTGCTCCGGCCCCTGCCCGCCCGCAACGAGCTGTACG
421   ------------+---------+---------+---------+---------+---------+ 480
      GGCACTACGACCTCCTCACGCAGCACGAGGCCGGGGACGGGCGGGCGTTGCTCGACATGC

GCTTCGGCGTGGCCGTGGCGTACCTCGGGATGCACGGGAGCGGGTGAACACGAAAATTC
481   ------------+---------+---------+---------+---------+---------+ 540
      CGAAGCCGCACCGGCACCGCATGGAGCCCTACGTGCCCCTCGCCCACTTGTGCTTTTAAG

GAGGCCTGGCGGGACCTGATCTCCGACATCACCGCCCTGCGTCTCGACTCCTTCGCCGTC
541   ------------+---------+---------+---------+---------+---------+ 600
      CTCCGGACCGCCCTGGACTAGAGGCTGTAGTGGCGGGACGCAGAGCTGAGGAAGCGGCAG

GCCGAGCGGCTGCGCTCGCTCCGTCTGCCGCCGGCCTGACCTCGCTGTCGCTCTCCCCG
601   ------------+---------+---------+---------+---------+---------+ 660
      CGGCTCGCCGACGCGAGCGAGGCAGACGGCGGCCGGACTGGAGCGACAGCGAGAGGGGC

CAGGAAACGGACTGCCTGATCCGTAACCGGACGCCACGCGCTCTGGCGCTCTTCTTTGCC
661   ------------+---------+---------+---------+---------+---------+ 720
      GTCCTTTGCCTGACGGACTAGGCATTGGCCTGCGGTGCGCGAGACCGCGAGAAGAAACGG

SstI
                                                 |
      GGTGCCCGTGAGCCCGGAGCCGGCATGGTCTGCCTGGGCCGGAGCTCGTTGTCCGCCGGA
721   ------------+---------+---------+---------+---------+---------+ 780
      CCACGGGCACTCGGGCCTCGGCCGTACCAGACGGACCCGGCCTCGAGCAACAGGCGGCCT
```

Fig.7.

```
                                                              PstI
                                                               |
        TCCTGGTCGCCGCAGTCAGTTGTGGCAGGTTGAAATGTCCTCCAACTGCAGCGCAGTAAG
   781  ---------+---------+---------+---------+---------+---------+  840
        AGGACCAGCGGCGTCAGTCAACACCGTCCAACTTTACAGGAGGTTGACGTCGCGTCATTC

CAGGAGTTCCCACACCTTGTCAGTCGTGGCAGGTGAGCGTCCCGGCGCCCCTCGTTCAGC
   841  ---------+---------+---------+---------+---------+---------+  900
        GTCCTCAAGGGTGTGGAACAGTCAGCACCGTCCACTCGCAGGGCCGCGGGGAGCAAGTCG

CGCGAACGACAACCCATAGGCAACGGTCAGCAGCAGGTGGACCACCACGTCCGGTGGCTG
   901  ---------+---------+---------+---------+---------+---------+  960
        GCGCTTGCTGTTGGGTATCCGTTGCCAGTCGTCGTCCACCTGGTGGTGCAGGCCACCGAC

CGTGGCCAAGGGTGAGTAGGGGGCTTGCTGTTGCTGGGTGTCACGGGCGGCCGCGGCCAT
   961  ---------+---------+---------+---------+---------+---------+ 1020
        GCACCGGTTCCCACTCATCCCCCGAACGACAACGACCCACAGTGCCCGCCGGCGCCGGTA

CTCGCGGCGGATGCGGTCCAGGAGATCCGGCGCCCCGCCCGCGGGCATGGTGCAGTCCGC
  1021  ---------+---------+---------+---------+---------+---------+ 1080
        GAGCGCCGCCTACGCCAGGTCCTCTAGGCCGCGGGGCGGGCGCCCGTACCACGTCAGGCG

TGCCAGCCGCAGCGCCGCACGGAACCGGATGTCGTGCTTCATTTGACGGCTTACGGCCAG
  1081  ---------+---------+---------+---------+---------+---------+ 1140
        ACGGTCGGCGTCGCGGCGTGCCTTGGCCTACAGCACGAAGTAAACTGCCGAATGCCGGTC

CACGAGGGCACGCAAGGCGGTTTCGGGCGCGCAGGCGGTCTCGGCGATGGAGCGGCCGAT
  1141  ---------+---------+---------+---------+---------+---------+ 1200
        GTGCTCCCGTGCGTTCCGCCAAAGCCCGCGCGTCCGCCAGAGCCGCTACCTCGCCGGCTA

GGTGTTCCATGTCTCTGTCGACTGGCTCACCAGTTCGTCGGCGAGCGCCTTCTTGGATGG
  1201  ---------+---------+---------+---------+---------+---------+ 1260
        CCACAAGGTACAGAGACAGCTGACCGAGTGGTCAAGCAGCCGCTCGCGGAAGAACCTACC

GAAGTGCCCGTAGAGAGCGCCCTTCGTCATGCCTGTGCGTACGGCGACCGTTGCCAGATT
  1261  ---------+---------+---------+---------+---------+---------+ 1320
        CTTCACGGGCATCTCTCGCGGGAAGCAGTACGGACACGCATGCCGCTGGCAACGGTCTAA

GGTGCCTGCATAGCCGTGCAGGGCGAACTCTTCAGCCGCCGCATCCAGCACCTGGTCCCG
  1321  ---------+---------+---------+---------+---------+---------+ 1380
        CCACGGACGTATCGGCACGTCCCGCTTGAGAAGTCGGCGGCGTAGGTCGTGGACCAGGGC

GGTGCGCATCGCCCTTGCCTGCTTCACCAACGCCCGAGTCCTCTCAAGGTCGTGAGCCAA
  1381  ---------+---------+---------+---------+---------+---------+ 1440
        CCACGCGTAGCGGGAACGGACGAAGTGGTTGCGGGCTCAGGAGAGTTCCAGCACTCGGTT
                 <---      *          <---       *

CGGGCCCGGAAAACATACCCTCGGGAAGGTATGTTAGTGGGGCGGTCGGCGCACGTGGA
  1441  ---------+---------+---------+---------+---------+---------+ 1500
        GCCCGGGCCTTTTGTATGGGAGCCCTTCCATACAATCACCCCCGCCAGCCGCGTGCACCT

CGATGTCCCAGTCATCGGCGCAAAAGTGGAGGCAGCACGGCTACCGCGCGGCAGGATTCA
  1501  ---------+---------+---------+---------+---------+---------+ 1560
        GCTACAGGGTCAGTAGCCGCGTTTTCACCTCCGTCGTGCCGATGGCGCGCCGTCCTAAGT

ACCGATGGCCGACGGATCGTCGTGGCCTAGCGGGCCTGGACGCCGTGCGCATGCACAGCG
  1561  ---------+---------+---------+---------+---------+---------+ 1620
        TGGCTACCGGCTGCCTAGCAGCACCGGATCGCCCGGACCTGCGGCACGCGTACGTGTCGC

GGGTCCGCGTCGGCGGGCAGCACCGGCCAGTTGGACCCCTGGGCGTGGCGCACCAGCAC
  1621  ---------+---------+---------+---------+---------+---------+ 1680
        CCCAGGGCGCAGCCGCCCGTCGTGGCCGGTCAACCTGGGGACCCGCACCGCGTGGTCGTG
                                                              PstI
```

Fig.7.

```
        GAGGTCCGTGCCGACCACGACCGGGTTCCCCACGGCCTGCAGCATGCCGAAGTCGCTCTC
  681   ---------+---------+---------+---------+---------+---------+  1740
        CTCCAGGCACGGCTGGTGCTGGCCCAAGGGGTGCCGACGTCGTACGGCTTCAGCGAGAG

GTGGTCCCCGTAGGCAAAGCAGTCTGCCGGCACCACCCCCTCTTCGCCATCACTTCGGT
  741   ---------+---------+---------+---------+---------+---------+  1800
        CACCAGGGGCATCCGTTTCGTCAGACGGCCGTGGTGGGGGAGAAGCGGTAGTGAAGCCA

CACGGCCTCAGCCTTCGCTTCGCCGATCATCGGGCGATTCACCTCGCCGGTGAGGACGCC
 1801   ---------+---------+---------+---------+---------+---------+  1860
        GTGCCGGAGTCGGAAGCGAAGCGGCTAGTAGCCCGCTAAGTGGAGCGGCCACTCCTGCGG

CTGGGCGTCGGCGAACTGCTCGGTGCACAGAATCCGGTCCGCGCCGAGGTCCTGCGCCAG
 1861   ---------+---------+---------+---------+---------+---------+  1920
        GACCCGCAGCCGCTTGACGAGCCACGTGTCTTAGGCCAGGCGCGGCTCCAGGACGCGGTC

GGGCGTGAGCAGTGGCCGGGCCGAGCCCGAGATCAGAACGATCGTGTGGCCGGCCCGGCG
 1921   ---------+---------+---------+---------+---------+---------+  1980
        CCCGCACTCGTCACCGGCCCGGCTCGGGCTCTAGTCTTGCTAGCACACCGGCCGGGCCGC

GTGCCGAGCGAGTGCCGCCAGGCCGGCCCTGACGTAGCCGTCCGGCCGCGTGCGGTAAGC
 1981   ---------+---------+---------+---------+---------+---------+  2040
        CACGGCTCGCTCACGGCGGTCCGGCCGGGACTGCATCGGCAGGCCGGCGCACGCCATTCG

PstI
                                           |
        GTGGTACCAGTCGCGGCCGGCCTCCTGCAGGCGAGCCAGGGAAACACCGGCGTAGCGCCG
 2041   ---------+---------+---------+---------+---------+---------+  2100
        CACCATGGTCAGCGCCGGCCGGAGGACGTCCGCTCGGTCCCTTTGTGGCCGCATCGCGGC

GTAGTAGACGCGGTTCATCTCCACCCGGCTCGCCCCTCGGCGCCGCATCGCCGTCAGATC
 2101   ---------+---------+---------+---------+---------+---------+  2160
        CATCATCTGCGCCAAGTAGAGGTGGGCCGAGCGGGGAGCCGCGGCGTAGCGGCAGTCTAG

GGCATCAGCACTGTGGCGTTGCCCGCTCGCCTGCGCGGTGATGTCGTCCCGCAAGCTGTG
 2161   ---------+---------+---------+---------+---------+---------+  2220
        CCGTAGTCGTGACACCGCAACGGGCGAGCGGACGCGCCACTACAGCAGGGCGTTCGACAC

CGGCGCCTGCCGTGCGAAGTCGAGCATGCTCTTGGCGGTGATCAGTGTCTCGTCCACATC
 2221   ---------+---------+---------+---------+---------+---------+  2280
        GCCGCGGACGGCACGCTTCAGCTCGTACGAGAACCGCCACTAGTCACAGAGCAGGTGTAG

GAAGAAGGCGATGGGCGTATGGCGGGCGACCGGTTCGCGGCTGTGCGACGTTCGCGCGG
 2281   ---------+---------+---------+---------+---------+---------+  2340
        CTTCTTCCGCTACCCCGCATACCGCCCGCTGGCCAAGCGCCGACACGCTGCAAGCGCGCC

GGGCTCGGGCATCACGCCGTACGTCTTTCTGTGTCTGGTGCGGTCGCGGTTCTGCCGGGT
 2341   ---------+---------+---------+---------+---------+---------+  2400
        CCCGAGCCCGTAGTGCGGCATGCAGAAAGACACAGACCACGCCAGCGCCAAGACGGCCCA

GGGCCGGCCGGCCGCCCCGGCTCGGCGGGGCCGACGCCGGTCGATGGGTCCGCACGGTCG
 2401   ---------+---------+---------+---------+---------+---------+  2460
        CCCGGCCGGCCGGCGGGCCGAGCCGCCCCGGCTGCGGCCAGCTACCCAGGCGTGCCAGC

AAGAGAGCAGGCGTGTATGCGCCGGCTGCTGCGTCGATGCTCAGGGCCCTGTGCGTGGCA
 2461   ---------+---------+---------+---------+---------+---------+  2520
        TTCTCTCGTCCGCACATACGCGGCCGACGACGCAGCTACGAGTCCCGGGACACGCACCGT

GCGGTGGTGATGTCCCGCCAGTGGCGCTGTACCGGGTCGTCTTCTGCCTGGCCACGTGAT
 2521   ---------+---------+---------+---------+---------+---------+  2580
        CGCCACCACTACAGGGCGGTCACCGCGACATGGCCCAGCAGAAGACGGACCGGTGCACTA

CCCGAGGCGCGCAGCAGTTGGTCGACGGCTTCGGAGCACAGTTCCACAGCCGCGGCGGCG
```

Fig.7

```
       GGGCTCCGCGCGTCGTCAACCAGCTGCCGAAGCCTCGTGTCAAGGTGTCGGCGCCGCCGC
2581 ---------+---------+---------+---------+---------+---------+ 2640
       CCCGAGGCGCGCAGCAGTTGGTCGACGGCTTCGGAGCACAGTTCCACAGCCGCGGCGGCG

TCCCGCTGCCCCTCGGCGACGAGGAGCGGGGTCACTGGCGCGTGGTCGGCCCGCTCTGCC
2641 ---------+---------+---------+---------+---------+---------+ 2700
       AGGGCGACGGGGAGCCGCTGCTCCTCGCCCCAGTGACCGCGCACCAGCCGGGCGAGACGG

GCTGCCTCCAGGAGCAGGCCTGCGGCGCGTATGCGTGCTGCTGCTCTGGTCAGGGTGTTG
2701 ---------+---------+---------+---------+---------+---------+ 2760
       CGACGGAGGTCCTCGTCCGGACGCCGCGCATACGCACGACGACGAGACCAGTCCCACAAC

GACGCCGGGGCACTGCGGTGCCCTGTCGTTCTGTGGCGGCGTGTGTCCAGGCGTCAAGA
2761 ---------+---------+---------+---------+---------+---------+ 2820
       CTGCGGCCCCCGTGACGCCACGGGACAGCAAGACACCGCCGCACACAGGTCCGCAGTTCT

SstI
        |
       GCTCCGCGGGCCGCCCCGAGAACCGGAAAGGCGAACATCAGCGCGCCCACCATGGCGTAG
2821 ---------+---------+---------+---------+---------+---------+ 2880
       CGAGGCGCCCGGCGGGGCTCTTGGCCTTTCCGCTTGTAGTCGCGCGGGTGGTACCGCATC

GGCACCGTGTGGCAGCGGGCCGAGCCGGGCAGGGGAGCAGCAGGTCCGACAAGGTGCAG
2881 ---------+---------+---------+---------+---------+---------+ 2940
       CCGTGGCACACCGTCGCCCGGCTCGGCCCGTCCCCCTCGTCGTCCAGGCTGTTCCACGTC

GTGCGGTGGCGGGGAACCAGCACCCCGTCCGCCTCGACGGTGTTGCTGCCGGTCCCGCGC
2941 ---------+---------+---------+---------+---------+---------+ 3000
       CACGCCACCGCCCCTTGGTCGTGGGGCAGGCGGAGCTGCCACAACGACGGCCAGGGCGCG

ATGCCGAGGGTGTGCCAGGTGTCGGTGACCGTCAGCTCGTCCCTGGGGACGGCGAACAGC
3001 ---------+---------+---------+---------+---------+---------+ 3060
       TACGGCTCCCACACGGTCCACAGCCACTGGCAGTCGAGCAGGGACCCCTGCCGCTTGTCG

CGGTGCCGCTCGGGAACGTTCCGGCCCGGTGTCCAGCTTGCGAGCAGCACCCAGTCGGCG
3061 ---------+---------+---------+---------+---------+---------+ 3120
       GCCACGGCGAGCCCTTGCAAGGCCGGGCCACAGGTCGAACGCTCGTCGTGGGTCAGCCGC

XhoI
                                                            |
       TGGTCGACGCCGCTGGCGAATCCCCAGCGCCCGGTGAGCCGCCAGCCGCCCGGCTCGAGG
3121 ---------+---------+---------+---------+---------+---------+ 3180
       ACCAGCTGCGGCGACCGCTTAGGGGTCGCGGGCCACTCGGCGGTCGGCGGGCCGAGCTCC

TTGGCCTCGCCCGACGGGGGCATGATGGCCGCGGCGATACGGGCGTCGGGCGAGGAGTGC
3181 ---------+---------+---------+---------+---------+---------+ 3240
       AACCGGAGCGGGCTGCCCCGTACTACCGGCGCCGCTATGCCCGCAGCCCGCTCCTCACG

CACAGTTCGCGTTGGGCCTTTTCGGGCAGGTACGAGGCCAGCCGCCCATGGGCCGCATAC
3241 ---------+---------+---------+---------+---------+---------+ 3300
       GTGTCAAGCGCAACCCGGAAAAGCCCGTCCATGCTCCGGTCGGCGGGTACCCGGCGTATG

AGCGTGGCGCACCAGGCGGTGGCGGCGCAGGTCCGGGCGAGCGTGGTCGCCGCCGTGAGC
3301 ---------+---------+---------+---------+---------+---------+ 3360
       TCGCACCGCGTGGTCCGCCACCGCCGCGTCCAGGCCCGCTCGCACCAGCGGCGGCACTCG

AGTTCGCCGAAGGTCCCGGCGCGGCCGCCGAAGCGCCGGGGGACGAAGTGGCGTGGAAAG
3361 ---------+---------+---------+---------+---------+---------+ 3420
       TCAAGCGGCTTCCAGGGCCGCGCCGGCGGCTTCGCGGCCCCCTGCTTCACCGCACCTTTC

CCGACGTCGGTGACCGCCCGGGCCACGTCGTCTGTGAGTCGTCGGTGTGTCTCCTGGACT
3421 ---------+---------+---------+---------+---------+---------+ 3480
       GGCTGCAGCCACTGGCGGGCCCGGTGCAGCAGACACTCAGCAGCCACACAGAGGACCTGA

CCGTGGTCCCGGTGCGCGAGAGCCACGGCGTGTTCCACCCCGTCGCGGGAAAACTCCCTG
```

Fig.7.

```
3481 ---------+---------+---------+---------+---------+---------+ 3540
     GGCACCAGGGCCACGCGCTCTCGGTGCCGCACAAGGTGGGGCAGCGCCCTTTTGAGGGAC

AGCGGCGCGGTCATGAGGCCACCGCCTTCGTCTGGTCGCCGTGGTGCGGGACGGTGGGCC
3541 ---------+---------+---------+---------+---------+---------+ 3600
     TCGCCGCGCC AGTA CTCCGGTGGCGGAAGCAGACCAGCGGCACCACGCCCTGCCACCCGG

CGGGGCTTCCCGTCCCGGCTGTCGTCGTCGTGGTGACGGTCGCGGTGATGAGCGTGCGGC
3601 ---------+---------+---------+---------+---------+---------+ 3660
     GCCCCGAAGGGCAGGGCCGACAGCAGCAGCACCACTGCCAGCGCCACTACTCGCACGCCG

TGCCTTGCCGGGCGGTGAGTTGCAGCGTACGTGTGCCGCTGTCCGGGCTGTGCCCGTGGG
3661 ---------+---------+---------+---------+---------+---------+ 3720
     ACGGAACGGCCCGCCACTCAACGTCGCATGCACACGGCGACAGGCCCGACACGGGCACCC

CGGCGGGGAGGGTGGTGATGGTGACAGGGGAGTCGAGTTCGCCGAATGCCTGGTAGGAAC
3721 ---------+---------+---------+---------+---------+---------+ 3780
     GCCGCCCCTCCCACCACTACCACTGTCCCCTCAGCTCAAGCGGCTTACGGACCATCCTTG

TTGCGACGGCCGTGAGGGCCACCTGCCGCGGGCCGAAGGCTCCGGGCGCGGGTGGGGTGA
3781 ---------+---------+---------+---------+---------+---------+ 3840
     AACGCTGCCGGCACTCCCGGTGGACGGCGCCCGGCTTCCGAGGCCCGCGCCCACCCCACT

GGGCTGTGGCGGCCTGACGGCAGGCCTCCAGCAGTGCCATGCCGGAAATGTGGTCCGATT
3841 ---------+---------+---------+---------+---------+---------+ 3900
     CCCGACACCGCCGGACTGCCGTCCGGAGGTCGTCACGGTACGGCCTTTACACCAGGCTAA

CGTGGTCGAAGAGGACCGGATGGTCCCGGCGCAGCCGCAGTTGCCAGGCTGTATCGGGCA
3901 ---------+---------+---------+---------+---------+---------+ 3960
     GCACCAGCTTCTCCTGGCCTACCAGGGCCGCGTCGGCGTCAACGGTCCGACATAGCCCGT

GGCCTTGCGCGGTGGCAAGCAGGACGTGCAGGTCGTCGTGGAAGCCGACGGTTTCGGGAG
3961 ---------+---------+---------+---------+---------+---------+ 4020
     CCGGAACGCGCCACCGTTCGTCCTGCACGTCCAGCAGCACCTTCGGCTGCCAAAGCCCTC

GAAGGGCGGTCGCCGCGCCTGCGGCTGCCTGCTGTGCGGGGCGCTCTGCCCGCCTGGCGC
4021 ---------+---------+---------+---------+---------+---------+ 4080
     CTTCCCGCCAGCGGCGCGGACGCCGACGGACGACACGCCCCGCGAGACGGGCGGACCGCG

GATCGCGGATCATCGCGTACCGCCGGGGGCGAGGACCTCGAAGCGGATGGCGCAGCGGC
4081 ---------+---------+---------+---------+---------+---------+ 4140
     CTAGCGCCTAGTAGCGCATGGCGGCCCCCGCTCCTGGAGCTTCGCCTACCGCGTCGCCG

CGCGGTGGAGTCCGGCCACGTACACGTCGGCGTTCAACGCCCTGGCCATCCGGCGCGGT
4141 ---------+---------+---------+---------+---------+---------+ 4200
     GCGCCACCTCAGGCCGGTGCATGTGCAGCCGCAAGTTGCGGGACCGGTAGGCCGCGCCCA

TCGTGGTGGTCTTCGTACTCGTGACGTCCAGGACGACAGGCAGCGGGCCGGAGTCCCAGA
4201 ---------+---------+---------+---------+---------+---------+ 4260
     AGCACCACCAGAAGCATGAGCACTGCAGGTCCTGCTGTCCGTCGCCCGGCCTCAGGGTCT

CAGGGAGATCGAGATCAAGATCGAGGCCCGACAGCACGAAGTGGTGGCCTATGGGCACGT
4261 ---------+---------+---------+---------+---------+---------+ 4320
     GTCCCTCTAGCTCTAGTTCTAGCTCCGGGCTGTCGTGCTTCACCACCGGATACCCGTGCA

CACAGAAGGTGTGTGAGAGGTGGATCGCCGACTGTCGTATGGTCTCCGCGGCTAGGAGGG
4321 ---------+---------+---------+---------+---------+---------+ 4380
     GTGTCTTCCACACACTCTCCACCTAGCGGCTGACAGCATACCAGAGGCGCCGATCCTCCC

GGTCGCACGGGCTCGATGTCGCGCGGTGCGCGAGGAAGGTGTTTCGGGGCCACAGGGCGG
4381 ---------+---------+---------+---------+---------+---------+ 4440
     CCAGCGTGCCCGAGCTACAGCGCGCCACGCGCTCCTTCCACAAAGCCCCGGTGTCCCGCC

CGACGGCGAACCGGTTCTCGCCCAGCGGTCGCGCGTCGGTGAGGAGTACTTCTGCCGCGG
```

Fig. 7.

```
                GCTGCCGCTTGGCCAAGAGCGGGTCGCCAGCGCGCAGCCACTCCTCATGAAGACGGCGCC
4441 ---------+---------+---------+---------+---------+---------+ 4500

CAGCCTTGTGTACGTCGGCCGGCGGCAGGGGCGCGCGAAGGAGAGCGGAGGGCAGCCGT
4501 ---------+---------+---------+---------+---------+---------+ 4560
     GTCGGAACACATGCAGCCGGCCGCCGTCCCCCGCGCGCTTCCTCTCGCCTCCCGTCGGCA

CGAACAGGAGGTCGTGGGGGGCGGGCAGTAAAAGACGGTTTGTATGGTTCATAGGGGCGC
4561 ---------+---------+---------+---------+---------+---------+ 4620
     GCTTGTCCTCCAGCACCCCCCGCCCGTCATTTTCTGCCAAACATACCAAGTATCCCCGCG

TACATCTCCCGGTGTGTCCTCGTACGGGACCACCGGCTGGCTTGCCGCGCTGCAAGACAG
4621 ---------+---------+---------+---------+---------+---------+ 4680
     ATGTAGAGGGCCACACAGGAGCATGCCCTGGTGGCCGACCGAACGGCGCGACGTTCTGTC

CCGGGATCGGTAAGCTGACCGAGAGAAATATACCTGCGGGAAGGTATTATGCAATGGGTT
4681 ---------+---------+---------+---------+---------+---------+ 4740
     GGCCCTAGCCATTCGACTGGCTCTCTTTATATGGACGCCCTTCCATAATACGTTACCCAA

TCCGTGCCGACCCGGGTCGCACCAGCATGGCGCCCGCAGGGCCCGCACACACGAAGGAAG
4741 ---------+---------+---------+---------+---------+---------+ 4800
     AGGCACGGCTGGGCCCAGCGTGGTCGTACCGCGGGCGTCCCGGGCGTGTGTGCTTCCTTC

GCAGCCATGACGAGCGCCCAACAACCCACGCCTTTCGCGGTCCGGTCCAACGTGCCGCGT
4801 ---------+---------+---------+---------+---------+---------+ 4860
     CGTCGGTACTGCTCGCGGGTTGTTGGGTGCGGAAAGCGCCAGGCCAGGTTGCACGGCGCA

GGACCTCACCCGCAGCAGGAGCGGTCGATCAAGACCCGGGCCCAGATCCTGGAGGCGGCG
4861 ---------+---------+---------+---------+---------+---------+ 4920
     CCTGGAGTGGGCGTCGTCCTCGCCAGCTAGTTCTGGGCCCGGGTCTAGGACCTCCGCCGC

TCGGAGATCTTCGCGTCGCGCGGCTACCGAGGGGCCTCCGTCAAGGACGTTGCCGAGCGT
4921 ---------+---------+---------+---------+---------+---------+ 4980
     AGCCTCTAGAAGCGCAGCGCGCCGATGGCTCCCCGGAGGCAGTTCCTGCAACGGCTCGCA

GTCGGCATGACCAAGGGCGCGGTGTACTTCCACTTCCCCAGCAAGGAATCACTGGCCATC
4981 ---------+---------+---------+---------+---------+---------+ 5040
     CAGCCGTACTGGTTCCCGCGCCACATGAAGGTGAAGGGGTCGTTCCTTAGTGACCGGTAG

GCCGTGGTGGAGGAGCACTACGCGCGCTGGCCCGCAGCGATGGAAGAGATCCGCATCCAG
5041 ---------+---------+---------+---------+---------+---------+ 5100
     CGGCACCACCTCCTCGTGATGCGCGCGACCGGGCGTCGCTACCTTCTCTAGGCGTAGGTC

GGCTTCACACCGCTGGAGACGGTCGAGGAGATGCTCCATCGCGCGGCGCAGGCCTTCCGC
5101 ---------+---------+---------+---------+---------+---------+ 5160
     CCGAAGTGTGGCGACCTCTGCCAGCTCCTCTACGAGGTAGCGCGCCGCGTCCGGAAGGCG

PstI
                                       |
     GACGACCCCGTGATGCAGGCCGGTGCCCGGCTGCAGAGTGAGCGCGCCTTCATCGACGCG
5161 ---------+---------+---------+---------+---------+---------+ 5220
     CTGCTGGGGCACTACGTCCGGCCACGGGCCGACGTCTCACTCGCGCGGAAGTAGCTGCGC

GAGCTGCCCCTGCCCTACGTGGACTGGACCCACCTGCTGGAGGTGCCGTTGCAGGACGCC
5221 ---------+---------+---------+---------+---------+---------+ 5280
     CTCGACGGGGACGGGATGCACCTGACCTGGGTGGACGACCTCCACGGCAACGTCCTGCGG

PvuII
                                       |
     CGTGAGGCCGGCCAGTTGCGGGCGGGCGTCGATCCCGCAGCAGCTGCCCGTTCCCTGGTG
5281 ---------+---------+---------+---------+---------+---------+ 5340
     GCACTCCGGCCGGTCAACGCCCGCCCGCAGCTAGGGCGTCGTCGACGGGCAAGGGACCAC

GCCGCCTTCTTCGGCATGCAGCACGTCTCCGACAATCTGCACCAGCGAGCGGACATCATG
```

Fig.7.

```
5341 --------+---------+---------+---------+---------+---------+ 5400
     CGGCGGAAGAAGCCGTACGTCGTGCAGAGGCTGTTAGACGTGGTCGCTCGCCTGTAGTAC

GAGCGGTGGCAGGAGCTGCGGGAGCTGATGTTCTTCGCTCTCCGCGCCTGACGGGGAGCG
5401 --------+---------+---------+---------+---------+---------+ 5460
     CTCGCCACCGTCCTCGACGCCCTCGACTACAAGAAGCGAGAGGCGCGGACTGCCCCTCGC

TCCGCAAAACTGGTGGTGCCACTGATAGGAGAATCTCCCTCTTTTCCCTGCGCTCCAGCA
5461 --------+---------+---------+---------+---------+---------+ 5520
     AGGCGTTTTGACCACCACGGTGACTATCCTCTTAGAGGGAGAAAAGGGACGCGAGGTCGT

CCGATTACGTTCTCTGCATGATTGCGGACACCGCGACGACCAGCGCGCGGACGGGAGCCC
5521 --------+---------+---------+---------+---------+---------+ 5580
     GGCTAATGCAAGAGACGTACTAACGCCTGTGGCGCTGCTGGTCGCGCGCCTGCCCTCGGG

CGGCCGCAGCGTTGCGTCTGTTCTGTTTTCATCATGCAGGAGGCCAGGGAACAGCATTCC
5581 --------+---------+---------+---------+---------+---------+ 5640
     GCCGGCGTCGCAACGCAGACAAGACAAAAGTAGTACGTCCTCCGGTCCCTTGTCGTAAGG

TCGGATGGCAGAAGAGACTGGGAGCGCGGGCGGAGGTGATTCCCGTCCGGCTGCCCCCGC
5641 --------+---------+---------+---------+---------+---------+ 5700
     AGCCTACCGTCTTCTCTGACCCTCGCGCCCGCCTCCACTAAGGGCAGGCCGACGGGGCG

PstI
               |
     CCGAGGACGTCTCTGCAGAGACAGCGGACGGGAGCGGAATGTCGATGACCCTCGTAGTCG
5701 --------+---------+---------+---------+---------+---------+ 5760
     GGCTCCTGCAGAGACGTCTCTGTCGCCTGCCCTCGCCTTACAGCTACTGGGAGCATCAGC

CTTCCCTCGATCACGAACTCGGCCCAATGCTGCGGCGGCCCTTCCTGTTCTACGGGCACA
5761 --------+---------+---------+---------+---------+---------+ 5820
     GAAGGGAGCTAGTGCTTGAGCCGGGTTACGACGCCGCCGGGAAGGACAAGATGCCCGTGT

GCATGGGCGCTCTCGTGGCCTACCACCTCACCCGCCTGCGCCAGTCCCGCGGCCGGCCCC
5821 --------+---------+---------+---------+---------+---------+ 5880
     CGTACCCGCGAGAGCACCGGATGGTGGAGTGGGCGGACGCGGTCAGGGCGCCGGCCGGGG

TGCCGGAGCGGTTGCTCATCGGCGCCTACCCGGCCCCCCATCTGCCGCACCGGCTCGCCC
5881 --------+---------+---------+---------+---------+---------+ 5940
     ACGGCCTCGCCAACGAGTAGCCGCGGATGGGCCGGGGGGTAGACGGCGTGGCCGAGCGGG

ACTGCACGCACTTGCCTGACGAGGACCTGCTCGCGCTGCTGCCGCCGCACCCTGCCGGCC
5941 --------+---------+---------+---------+---------+---------+ 6000
     TGACGTGCGTGAACGGACTGCTCCTGGACGAGCGCGACGACGGCGGCGTGGGACGGCCGG

ACTCTCGCCTGCTGCGCCAGGCGCCCGGCCTGGCGACAGCGACTGCGGCGCGGCTGCGCC
6001 --------+---------+---------+---------+---------+---------+ 6060
     TGAGAGCGGACGACGCGGTCCGCGGGCCGGACCGCTGTCGCTGACGCCGCGCCGACGCGG

TGCACCTCGGCCTGTGTGACAGCGCCGCGCCGGCGGCACCGAACCCCGCGCAGCACACCG
6061 --------+---------+---------+---------+---------+---------+ 6120
     ACGTGGAGCCGGACACACTGTCGCGGCGCGGCCGCCGTGGCTTGGGGCGCGTCGTGTGGC

GCCACGGTTCCCCGCAGGGGAGGAGTGAACCGCTGAGGTGTCCGGTGGATGTGTTCACCG
6121 --------+---------+---------+---------+---------+---------+ 6180
     CGGTGCCAAGGGGCGTCCCCTCCTCACTTGGCGACTCCACAGGCCACCTACACAAGTGGC

GGATCAGCGATCCGCTGGTGACGGACGCCGAGGCAGCCGCATGGCGGCACCACACCCGCG
6181 --------+---------+---------+---------+---------+---------+ 6240
     CCTAGTCGCTAGGCGACCACTGCCTGCGGCTCCGTCGGCGTACCGCCGTGGTGTGGGCGC

CAGGCTGCCGTATACACCGCATCCCCGGCGGGCATTTCTTCACGCGCGAGACCCCGGAAT
6241 --------+---------+---------+---------+---------+---------+ 6300
     GTCCGACGGCATATGTGGCGTAGGGGCCGCCCGTAAAGAAGTGCGCGCTCTGGGGCCTTA
```

Fig.7.

```
      CTAGGGCCGCGTTCTTCGACCGGCTGTGCACGGTGCTTGCAGGGCCGTCGGAATGGGCGG
6301  ------------+---------+---------+---------+---------+---------+ 6360
      GATCCCGGCGCAAGAAGCTGGCCGACACGTGCCACGAACGTCCCGGCAGCCTTACCCGCC

CCGGAGCATCGGGTCCCCTCCCTGTCACCGTCGCTTCGTAAAAGCGTTTCCCGCAACCCA
6361  ------------+---------+---------+---------+---------+---------+ 6420
      GGCCTCGTAGCCCAGGGGAGGGACAGTGGCAGCGAAGCATTTTCGCAAAGGGCGTTGGGT

GGAGGACGTTCATGTACCCCGAGACGCTCGGATTCGGTGCTTTCCTCTCCCCCATGCATC
6421  ------------+---------+---------+---------+---------+---------+ 6480
      CCTCCTGCAAGTACATGGGGCTCTGCGAGCCTAAGCCACGAAAGGAGAGGGGGTACGTAG

CGCTGGGCGAGAATCCCACGCTGCAATTTCAGCGCGACCTTGAGCTGATAGAACTCCTCG
6481  ------------+---------+---------+---------+---------+---------+ 6540
      GCGACCCGCTCTTAGGGTGCGACGTTAAAGTCGCGCTGGAACTCGACTATCTTGAGGAGC

ACCGGCTCGACTACAACGAATTCTGGGTCGGCGAGCATCACTCCATGGGCTGGAACACCA
6541  ------------+---------+---------+---------+---------+---------+ 6600
      TGGCCGAGCTGATGTTGCTTAAGACCCAGCCGCTCGTAGTGAGGTACCCGACCTTGTGGT

TCGGCAGCCCGGAGCTGATGGTTGCGGCTGCCGCCGAGCGGACCCGTCGTATCACCCTGG
6601  ------------+---------+---------+---------+---------+---------+ 6660
      AGCCGTCGGGCCTCGACTACCAACGCCGACGGCGGCTCGCCTGGGCAGCATAGTGGGACC

CCACCGGTGTGATGACGCTGCCGTACCACCACCCGTTCATGGTGGCGAGCCGTGCGGTGC
6661  ------------+---------+---------+---------+---------+---------+ 6720
      GGTGGCCACACTACTGCGACGGCATGGTGGTGGGCAAGTACCACCGCTCGGCACGCCACG

ACCTCGACCATCTGACCCGTGGCCGGTTCGTGCTCGGTGTGGGCGCGGGCGGCATCCCGA
6721  ------------+---------+---------+---------+---------+---------+ 6780
      TGGAGCTGGTAGACTGGGCACCGGCCAAGCACGAGCCACACCCGCGCCCGCCGTAGGGCT

CCGACGCCCGCATGATCGGCCGTGAGATGAGCGAACTGCGCACCATGTTCGGCGAGGCAC
6781  ------------+---------+---------+---------+---------+---------+ 6840
      GGCTGCGGGCGTACTAGCCGGCACTCTACTCGCTTGACGCGTGGTACAAGCCGCTCCGTG

TGGAGGCGGTCGTCGCGCTGGTCAACGGCGAGGAGCGGGTGACCAAGAAGACCTCGTGGT
6841  ------------+---------+---------+---------+---------+---------+ 6900
      ACCTCCGCCAGCAGCGCGACCAGTTGCCGCTCCTCGCCCACTGGTTCTTCTGGAGCACCA

PvuII
                                        |
      TCACGCTGAAGGACGCCAAGCTCCAGCTGTCCCCGTACCGTGCATCAGGGCTGGAGATCG
6901  ------------+---------+---------+---------+---------+---------+ 6960
      AGTGCGACTTCCTGCGGTTCGAGGTCGACAGGGGCATGGCACGTAGTCCCGACCTCTAGC

CCGCTGCCAGCGTCGCCTCCGGCAACAGCATGCGGCTGGCCGGCCGCTACGGGATCAGCA
6961  ------------+---------+---------+---------+---------+---------+ 7020
      GGCGACGGTCGCAGCGGAGGCCGTTGTCGTACGCCGACCGGCCGGCGATGCCCTAGTCGT

CCGTCTCCTTCGGTGCGCCGCGGCCTGGTCATCCCCGACCCGACATGCGTACCCAGTGGT
7021  ------------+---------+---------+---------+---------+---------+ 7080
      GGCAGAGGAAGCCACGCGGCGCCGGACCAGTAGGGGCTGGGCTGTACGCATGGGTCACCA

CGTATGCGGAGGAGGCTGCGGCCGAACAGGGCACCACGGTGGACCGCAGGAACTGGCGAA
7081  ------------+---------+---------+---------+---------+---------+ 7140
      GCATACGCCTCCTCCGACGCCGGCTTGTCCCGTGGTGCCACCTGGCGTCCTTGACCGCTT

TCACCCTGCCGGTATACGTGGCAGAGACGCGCGAGCAGGCCCTTGCCGATGTCCGGGAGG
7141  ------------+---------+---------+---------+---------+---------+ 7200
      AGTGGGACGGCCATATGCACCGTCTCTGCGCGCTCGTCCGGGAACGGCTACAGGCCCTCC

GTTACGACCGCTGGGCCTACGGATACTGGGGCGACATCCGCGGCCTCGACGTCAGCGTCC
```

Fig.7.

```
7201 ---------+---------+---------+---------+---------+---------+ 7260
     CAATGCTGGCGACCCGGATGCCTATGACCCCGCTGTAGGCGCCGGAGCTGCAGTCGCAGG

CCGGCGTCAAGCGTGCGCAGGCTCTGGAGGCTGCCGTGGACGCGGGCAGCGCCATCGTCG
7261 ---------+---------+---------+---------+---------+---------+ 7320
     GGCCGCAGTTCGCACGCGTCCGAGACCTCCGACGGCACCTGCGCCCGTCGCGGTAGCAGC

GCTCCGTCGAGGACGTGGTGGCCGGCGTCGAGCGGCTCCGTGAGGAGGTCGGCGGCTTCG
7321 ---------+---------+---------+---------+---------+---------+ 7380
     CGAGGCAGCTCCTGCACCACCGGCCGCAGCTCGCCGAGGCACTCCTCCAGCCGCCGAAGC

GGACCCTGCTCGTCTACGCGCAGGACTGGGCCGACTGGGAGAAGACGAAGCGGAGCTATG
7381 ---------+---------+---------+---------+---------+---------+ 7440
     CCTGGGACGAGCAGATGCGCGTCCTGACCCGGCTGACCCTCTTCTGCTTCGCCTCGATAC

ACCTGCTGGCCCGCTACGTCGCCCCGCACTTCACCGGCTCCACCCGGCGACTGTACGAGT
7441 ---------+---------+---------+---------+---------+---------+ 7500
     TGGACGACCGGGCGATGCAGCGGGGCGTGAAGTGGCCGAGGTGGGCCGCTGACATGCTCA

CGGTGCAGTGGTACCAGGACAACCGCGACCTGTTTCCGCAGCTCATCCCGTAAACCGTGC
7501 ---------+---------+---------+---------+---------+---------+ 7560
     GCCACGTCACCATGGTCCTGTTGGCGCTGGACAAAGGCGTCGAGTAGGGCATTTGGCACG

ACGCCGTGCCTGCCGGCGCCACGGGCAGCTCCAGGCACGGCTCGGCATCCCTCCCTGGAG
7561 ---------+---------+---------+---------+---------+---------+ 7620
     TGCGGCACGGACGGCCGCGGTGCCCGTCGAGGTCCGTGCCGAGCCGTAGGGAGGGACCTC

TGACAGCGACACCCATGGCCACCGAACCGATACGCATCGGCGTGGTCGGCGCCTCCCCG
7621 ---------+---------+---------+---------+---------+---------+ 7680
     ACTGTCGCTGTGGGGTACCGGTGGCTTGGCTATGCGTAGCCGCACCAGCCGCGGAGGGGC

PstI
                                         |
     GACCGGGGCTGGGCCGCCGACGCACACCTGCCGGCCCTGCAGCACCTGCCGCAGTACAAG
7681 ---------+---------+---------+---------+---------+---------+ 7740
     CTGGCCCCGACCCGGCGGCTGCGTGTGGACGGCCGGGACGTCGTGGACGGCGTCATGTTC

ATCACCGCGGTCGGCACCCGCCGGGCGGACAGTGCGCACCGGGCCGCTCGCCGGTACGGG
7741 ---------+---------+---------+---------+---------+---------+ 7800
     TAGTGGCGCCAGCCGTGGGCGGCCCGCCTGTCACGCGTGGCCCGGCGAGCGGCCATGCCC

GCGACCCACGCTTTCACCGACCCCCGCAGCCTCGCCGCACATCCCGACGTGGAACTGGTC
7801 ---------+---------+---------+---------+---------+---------+ 7860
     CGCTGGGTGCGAAAGTGGCTGGGGGCGTCGGAGCGGCGTGTAGGGCTGCACCTTGACCAG

GCGATCGTCGTGAAAGTGCCGGACCATGCGCGGCTGGTGGAGGCGGCGCTCGCGGCGGGC
7861 ---------+---------+---------+---------+---------+---------+ 7920
     CGCTAGCAGCACTTTCACGGCCTGGTACGCGCCGACCACCTCCGCCGCGAGCGCCGCCCG

AAGCATGTCCTGTGCGAGTGGCCCCTTGCCCGGACCACCGAGGAGGCCGCCCAGCTAACG
7921 ---------+---------+---------+---------+---------+---------+ 7980
     TTCGTACAGGACACGCTCACCGGGGAACGGGCCTGGTGGCTCCTCCGGCGGGTCGATTGC

GCGGCCGCTCACGGAGCCGGTGTGGTGAACGCCGTCGGCCTCCAGGCGCGGCACACCCCG
7981 ---------+---------+---------+---------+---------+---------+ 8040
     CGCCGGCGAGTGCCTCGGCCACACCACTTGCGGCAGCCGGAGGTCCGCGCCGTGTGGGGC

ACGGTCGTCCGGGCCCGGGAACTGATCAGGCAGGGGTACGTCGGCCGGGTCACCTCGGTC
8041 ---------+---------+---------+---------+---------+---------+ 8100
     TGCCAGCAGGCCCGGGCCCTTGACTAGTCCGTCCCCATGCAGCCGGCCCAGTGGAGCCAG

ACCGTGTACAGCACGCGGGGGGTCGCGGCCGGGGGCGGCTGCCCGCCGCCTTCGCCTAC
8101 ---------+---------+---------+---------+---------+---------+ 8160
     TGGCACATGTCGTGCGCCCCCAGCGCCGGCCCCCGCCGACGGGCGGCGGAAGCGGATG
```

Fig.7.

```
          ACCCTCGACTCCACGAACGGCGCCGGCACCTTCGAGGTCGCCGGCGGGCACACGCTCGAC
8161      ------------+---------+---------+---------+---------+---------+  8220
          TGGGAGCTGAGGTGCTTGCCGCGGCCGTGGAAGCTCCAGCGGCCGCCCGTGTGCGAGCTG

GCGGTGCAGTACCTGCTCGGCAGGGAGATGACCGGCCTGTCGGCTGCGCTGTCCGTTCAG
8221      ------------+---------+---------+---------+---------+---------+  8280
          CGCCACGTCATGGACGAGCCGTCCCTCTACTGGCCGGACAGCCGACGCGACAGGCAAGTC

CATCCGCGGATCACACTCGACGAGGACGCCCGGCAGACGGGGGCGACCAGCCCCGATCAT
8281      ------------+---------+---------+---------+---------+---------+  8340
          GTAGGCGCCTAGTGTGAGCTGCTCCTGCGGGCCGTCTGCCCCCGCTGGTCGGGGCTAGTA

GTCGCGCTGCACGCGACGCTGGAAGGCGGCGCCGCGCTGGTGGTCCACATCCACGATGCC
8341      ------------+---------+---------+---------+---------+---------+  8400
          CAGCGCGACGTGCGCTGCGACCTTCCGCCGCGGCGCGACCACCAGGTGTAGGTGCTACGG

AAGAACAGCGGCGCGGGCACCCGCATCGAGATCTCCGGCACGCAAGGGGAGCTGGCCATC
8401      ------------+---------+---------+---------+---------+---------+  8460
          TTCTTGTCGCCGCGCCCGTGGGCGTAGCTCTAGAGGCCGTGCGTTCCCCTCGACCGGTAG

PstI
                                                 |
          GTATCCACCGGACCACGAAGCGGCAGCGGGCTGCAGATCAGCGAACTGGCCCTGCTCGGA
8461      ------------+---------+---------+---------+---------+---------+  8520
          CATAGGTGGCCTGGTGCTTCGCCGTCGCCCGACGTCTAGTCGCTTGACCGGGACGAGCCT

GCGCAGGGGACAGAGCCGTCCGGGCAGGAGCTGCCCTTTCCCGGCTCCTGGGGCACGGCC
8521      ------------+---------+---------+---------+---------+---------+  8580
          CGCGTCCCCTGTCTCGGCAGGCCCGTCCTCGACGGGAAAGGGCCGAGGACCCCGTGCCGG

GTGCCAGCGGACGGTCTCGATGCGGCCCAGCACACCATGGCTGTGCAGTACGCGGCTCTG
8581      ------------+---------+---------+---------+---------+---------+  8640
          CACGGTCGCCTGCCAGAGCTACGCCGGGTCGTGTGGTACCGACACGTCATGCGCCGAGAC

GCCGCGGACATCCGCGAGGGCGGCAGTCGTGTGCCTCGTTTCGCCGACGGGATCGAGCTG
8641      ------------+---------+---------+---------+---------+---------+  8700
          CGGCGCCTGTAGGCGCTCCCGCCGTCAGCACACGGAGCAAAGCGGCTGCCCTAGCTCGAC

CACCGGCTGCTGGACGCCGTACGGCTGTCCTCCGCAACCGGCTGCCGGCTGGAGCGCCGT
8701      ------------+---------+---------+---------+---------+---------+  8760
          GTGGCCGACGACCTGCGGCATGCCGACAGGAGGCGTTGGCCGACGGCCGACCTCGCGGCA

GCGGGCGAGCGGTGGCCGGTCAGCTCTCCCTGGCCGCGGCGTCGACGATCGCGGTGAGCA
8761      ------------+---------+---------+---------+---------+---------+  8820
          CGCCCGCTCGCCACCGGCCAGTCGAGAGGGACCGGCGCCGCAGCTGCTAGCGCCACTCGT

GGCCGGGGAAGGCCTGATCGAGATCATCGGTGCGAAGCGTGTTCATCTTCGAGGTGCCGA
8821      ------------+---------+---------+---------+---------+---------+  8880
          CCGGCCCCTTCCGGACTAGCTCTAGTAGCCACGCTTCGCACAAGTAGAAGCTCCACGGCT

TGTAGTACTGCCTGATGATCCCGGCCTGGCGCAACACCTTGAAGTGGTGAGTGCCGGTCG
8881      ------------+---------+---------+---------+---------+---------+  8940
          ACATCATGACGGACTACTAGGGCCGGACCGCGTTGTGGAACTTCACCACTCACGGCCAGC

PvuII
                                                                |
          AGCGGGAGACGGTGATGTCGAAGGTGCCGCAGGCGATGTCCTCGGGTGCCTTAGCCAGCT
8941      ------------+---------+---------+---------+---------+---------+  9000
          TCGCCCTCTGCCACTACAGCTTCCACGGCGTCCGCTACAGGAGCCCACGGAATCGGTCGA

GCCGGACGATGCTGCGGCGCACCGGATCGACCAGCGCGTCCAGGACGCCCTGGAGGGTGA
9001      ------------+---------+---------+---------+---------+---------+  9060
          CGGCCTGCTACGACGCCGCGTGGCCTAGCTGGTCGCGCAGGTCCTGCGGGACCTCCCACT
```

Fig.7.

```
           TGGCGTCAGCGTCCGGATGGTCGGTGATGCGCTCTGTCGTGATCCGTGCCGCCACGGCTG
  9061     ------------+----------+----------+----------+----------+----------+  9120
           ACCGCAGTCGCAGGCCTACCAGCCACTACGCGAGACAGCACTAGGCACGGCGGTGCCGAC
                                                                     ←
                                                                     *

TCCGCCTCCTCGTCGCGTGTCGTTCCACCATGGTACGACAGCCATCAAATGTTGACGGCC
  9121     ------------+----------+----------+----------+----------+----------+  9180
           AGGCGGAGGAGCAGCGCACAGCAAGGTGGTACCATGCTGTCGGTAGTTTACAACTGCCGG
                                              ←
                                              *

ATCAAAGTTTGACAGCCGTCGTCATATGAGCTTCAGTGAGAACGCACGGTAATTCCGGCG
  9181     ------------+----------+----------+----------+----------+----------+  9240
           TAGTTTCAAACTGTCGGCAGCAGTATACTCGAAGTCACTCTTGCGTGCCATTAAGGCCGC

CAGTTGGGCGGCCGCCATCCCCCCCCGGCCGCCCTCTGCCGGCCACTCCTCAGGACGCGG
  9241     ------------+----------+----------+----------+----------+----------+  9300
           GTCAACCCGCCGGCGGTAGGGGGGGGCCGGCGGGAGACGGCCGGTGAGGAGTCCTGCGCC

CCCATACCCGACCCCCACAGGAGCAGAACAGCATGACCACTGTCCGAACAGGCGGGGCGC
  9301     ------------+----------+----------+----------+----------+----------+  9360
           GGGTATGGGCTGGGGGTGTCCTCGTCTTGTCGTACTGGTGACAGGCTTGTCCGCCCCGCG
                                             →

AGACCGCCGAAGTCCCGGCGGGCGGCCGGCGCGATGTCCCCAGCGGGGTGAAGATCACCG
  9361     ------------+----------+----------+----------+----------+----------+  9420
           TCTGGCGGCTTCAGGGCCGCCCGCCGGCCGCGCTACAGGGGTCGCCCCACTTCTAGTGGC

CTCTGGCCACGGGATTCGTCATGGCGACCCTGGACGTCACCGTGGTGAACGTCGCCGGAG
  9421     ------------+----------+----------+----------+----------+----------+  9480
           GAGACCGGTGCCCTAAGCAGTACCGCTGGGACCTGCAGTGGCACCACTTGCAGCGGCCTC

PvuII
                                                       |
           CCACCATCCAGGAGAGCCTGGACACCACGCTGACCCAGCTG
  9481     ------------+----------+----------+---------+-  9521
           GGTGGTAGGTCCTCTCGGACCTGTGGTGCGACTGGGTCGAC
```

Enzymes that do cut:

PstI    PvuII    SstI    XhoI

Enzymes that do not cut:

NONE

Fig. 8a.

```
  1 VKQARAMRTR DQVLDAAAEE FALHGYAGTN LATVAVRTGM TKGALYGHFP  50
 51 SKKALADELV SQSTETWNTI GRSIAETACA PETALRALVL AVSRQMKHDI 100
101 RFRAALRLAA DCTMPAGGAP DLLDRIRREM AAAARDTQQQ QAPYSPLATQ 150
151 PPDVVVHLLL TVAYGLSFAA ERGAPGRSPA TTDKVWELLL TALQLEDIST 200
201 CHN*                                                  203
```

Fig. 8b.

```
VMPEPPRERR TAANRSPAIR PIAFFDVDET LITAKSMLDF ARQAPHSLRD
DITAQASGQR HSADADLTAM RRRGASRVEM NRVYYRRYAG VSLARLQEAG
RDWYHAYRTR PDGYVRAGLA ALARHRRAGH TIVLISGSAR PLLTPLAQDL
GADRILCTEQ FADAQGVLTG EVNRPMIGEA KAEAVTEVMA KRGVVPADCF
AYGDHESDFG MLQAVGNPVV VGTDLVLVRH AQGSNWPVLP ADAGPRCACA
RRPGPLGHDD PSAIG*
```

Fig. 8C.

```
MTAPLREFSR DGVEHAVALA HRDHGVQETH RRLTDDVARA VTDVGFPRHF
VPRRFGGRAG TFGELLTAAT TLARTCAATA WCATLYAAHG RLASYLPEKA
QRELWHSSPD ARIAAAIMPP SGEANLEPGG WRLTGRWGFA SGVDHADWVL
LASWTPGRNV PERHRLFAVP RDELTVTDTW HTLGMRGTGS NTVEADGVLV
PRHRTCTLSD LLLPLPGSAR CHTVPYAMVG ALMFAFPVLG AARGALDAWT
HAATERQGTA VPPASNTLTR AAARIRAAGL LLEAAAERAD HAPVTPLLVA
EGQRDAAAAV ELCSEAVDQL LRASGSRGQA EDDPVQRHWR DITTAATHRA
LSIDAAAGAY TPALFDRADP STGVGPAEPG GPAGPPGRTA TAPDTERRTA
     *
```

Fig.8d.

```
  1  MNHTNRLLLP APHDLLFDGC PPLSFARPLP PADVHKAAAA EVLLTDARPL  50
 51  GENRFAVAAL WPRNTFLAHR ATSSPCDPLL AAETIRQSAI HLSHTFCDVP 100
101  IGHHFVLSGL DLDLDLPVWD SGPLPVVLDV TSTKTTTNPR RMARALNADV 150
151  YVAGLHRGRC AIRFEVLAPR RYAMIRDRAR RAERPAQQAA AGAATALPPE 200
201  TVGFHDDLHV LLATAQGLPD TAWQLRLRRD HPVLFDHESD HISGMALLEA 250
251  CRQAATALTP PAPGAFGPRQ VALTAVASSY QAFGELDSPV TITTLPAAHG 300
301  HSPDSGTRTL QLTARQGSRT LITATVTTTT TAGTGSPGPT VPHHGDQTKA 350
351  VAS*                                                  353
```

Fig.8E.

```
  1  MTSAQQPTPF AVRSNVPRGP HPQQERSIKT RAQILEAASE IFASRGYRGA  50
 51  SVKDVAERVG MTKGAVYFHF PSKESLAIAV VEEHYARWPA AMEEIRIQGF 100
101  TPLETVEEML HRAAQAFRDD PVMQAGARLQ SERAFIDAEL PLPYVDWTHL 150
151  LEVPLQDARE AGQLRAGVDP AAAARSLVAA FFGMQHVSDN LHQRADIMER 200
201  WQELRELMFF ALRA*                                      214
```

Fig.8f.

```
VIPVRLPPPE DVSAETADGS GMSMTLVVAS LDHELGPMLR RPFLFYGHSM
GALVAYHLTR LRQSRGRPLP ERLLIGAYPA PHLPHRLAHC THLPDEDLLA
LLPPHPAGHS RLLRQAPGLA TATAARLRLH LGLCDSAAPA APNPAQHTGH
GSPQGRSEPL RCPVDVFTGI SDPLVTDAEA AAWRHHTRAG CRIHRIPGGH
FFTRETPESR AAFFDRLCTV LAGPSEWAAG ASGPLPVTVA S*
```

Fig. 8g.

MYPETLGFGA FLSPMHPLGE NPTLQFQRDL ELIELLDRLD YNEFWVGEHH

SMGWNTIGSP ELMVAAAAER TRRITLATGV MTLPYHHPFM VASRAVHLDH

LTRGRFVLGV GAGGIPTDAR MIGREMSELR TMFGEALEAV VALVNGEERV

TKKTSWFTLK DAKLQLSPYR ASGLEIAAAS VASGNSMRLA GRYGISTVSF

GAPRPGHPRP DMRTQWSYAE EAAAEQGTTV DRRNWRITLP VYVAETREQA

LADVREGYDR WAYGYWGDIR GLDVSVPGVK RAQALEAAVD AGSAIVGSVE

DVVAGVERLR EEVGGFGTLL VYAQDWADWE KTKRSYDLLA RYVAPHFTGS

TRRLYESVQW YQDNRDLFPQ LIP*

Fig. 8h.

MATEPIRIGV VGASPDRGWA ADAHLPALQH LPQYKITAVG TRRADSAHRA

ARRYGATHAF TDPRSLAAHP DVELVAIVVK VPDHARLVEA ALAAGKHVLC

EWPLARTTEE AAQLTAAAHG AGVVNAVGLQ ARHTPTVVRA RELIRQGYVG

RVTSVTVYST RGVAAGGRLP AAFAYTLDST NGAGTFEVAG GHTLDAVQYL

LGREMTGLSA ALSVQHPRIT LDEDARQTGA TSPDHVALHA TLEGGAALVV

HIHDAKNSGA GTRIEISGTQ GELAIVSTGP RSGSGLQISE LALLGAQGTE

PSGQELPFPG SWGTAVPADG LDAAQHTMAV QYAALAADIR EGGSRVPRFA

DGIELHRLLD AVRLSSATGC RLERRAGERW PVSSPWPRRR RSR*

P=PstI; S=SstI; B=BglII

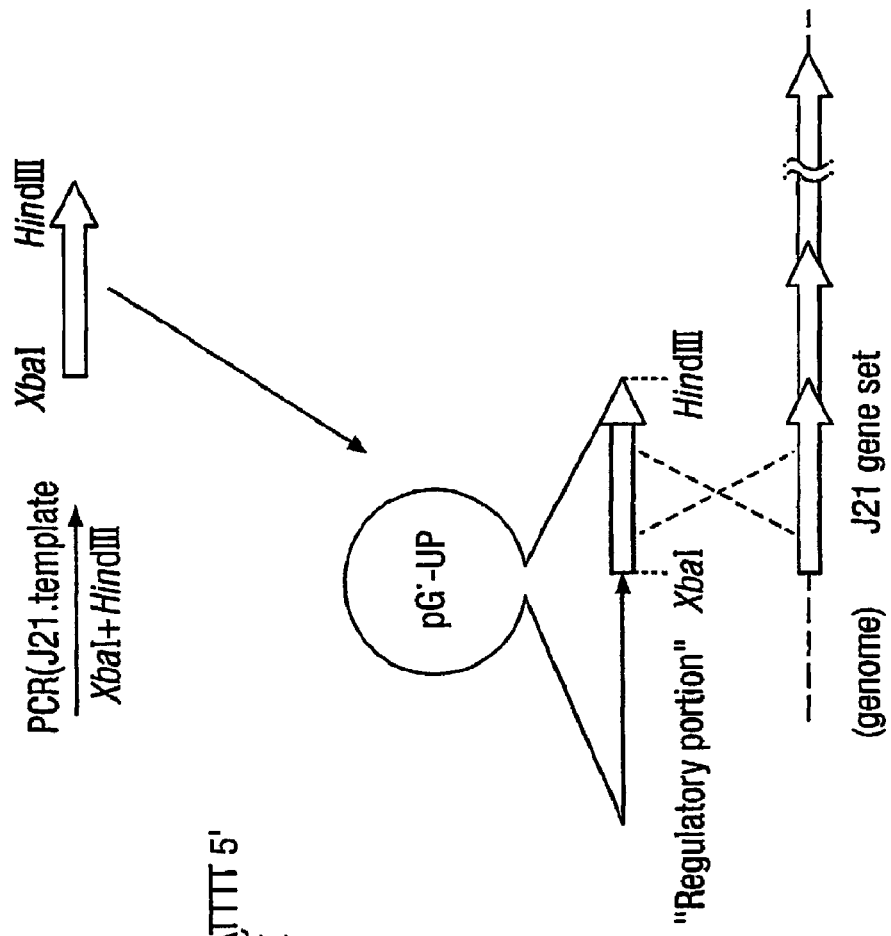

METHODS AND MATERIALS RELATING TO GENE EXPRESSION

The present invention relates to material derived from the SCP1 plasmid of *Streptomyces coelicolor* A3(2) and methods and uses relating thereto, in particular to material derived from the gene cluster for methylenomycin A biosynthesis.

Underlying the invention is work carried out by the inventors in sequencing and deducing the function of various genes in the methylenomycin A biosynthetic gene cluster.

The natural role of the DNA to which the present invention relates is the production of the antibiotic methylenomycin A and its congeners. The whole cluster of methylenomycin production, resistance and regulatory genes (the mmy gene cluster) is known only from studies of *Streptomyces coelicolor* A3(2) and *Streptomyces violaceoruber* No. 2416 SANK 95570 (Chater and Bruton, 1985). In these two bacteria the genes concerned with methylenomycin production are present on different plasmids, SCP1 and pSV1 (Aguilar and Hopwood, 1982). No other example is known of plasmid-specified antibiotic production in *Streptomyces*. Where studied, all naturally occurring *Streptomyces* plasmids, including SCP1, can be transferred to new *Streptomyces* hosts by conjugation.

The DNA sequence of a 9.5 kb stretch of this gene cluster has now been discovered, and the inventors have identified several genes and their transcriptional organisation. They found that the transcriptional organisation of this region is significantly different from that suggested previously, for example in Chater and Bruton (1985). The function of certain of the genes has newly been deduced from the discovery that they display high levels of homology with other genes which are involved in the regulation of other, chromosomally located, antibiotic biosynthetic gene clusters in diverse streptomycetes.

This discovery is particularly surprising in view of the fact that methylenomycin is the only Streptomyces antibiotic whose biosynthesis is known to be conferred by a plasmid, rather than native *Streptomyces* genomic DNA. It implies that these genes should be adapted to function in an appropriately controlled manner in any Streptomyces host to which these plasmids may be transmitted.

Further, the inventors have discovered that the insertion of a gene of interest into a particular transcriptional unit within this 9.5 kb stretch allows that gene to be regulated so as to be expressed only at high cell. density. This transcriptional unit contains three methylenomycin biosynthetic genes. Similar results were obtained for another transcriptional unit of the mmy gene cluster, indicating that other biosynthetic genes are similarly regulated, as well as for a transcriptional unit that is itself part of the regulatory system.

On the basis of these discoveries, the inventors now provide a model of how methylenomycin expression is regulated in *Streptomyces*.

This model allows predictions to be made about the effect of disrupting certain portions of the gene cluster. Observations consistent with these predictions have been made.

The inventors have sequenced and identified a block of eight genes, designated mmyR, mmfP, mmfH, mmfL, mmfR, mmyT, mmyO and mmyG. The arrangement of these genes in the sequenced stretch of DNA is shown in FIG. 1*d*. FIGS. 1*a-c* show the location of this stretch in the methylenomycin gene cluster and on the SCP1 plasmid.

The authors have further sequenced and identified five more genes, designated mmyK, mmyP, mmyA, mmyC and mmyX, which are part of an incompletely defined transcription unit, mmy . . . XCAPK, in a nearby block. The organisation of these genes, and further nearby genes, is shown in FIG. 1*e*. The sequence of this whole region, along with deduced amino acid sequences of the gene products, is now available in the GenBank/EMBL database, under accession number AJ276673.

At the heart of the system are the products of the two genes mmyR and mmfR. The inventors have discovered that these two genes encode proteins with very significant similarity to several other proteins from various *Streptomyces* spp. (FIG. 2). A known model member of this protein sub-family is ArpA, a protein of *Streptomyces griseus* (see e.g. Onaka and Horinouchi, 1997; Onaka et al., 1997; and Sugiyama et al., 1998). ArpA binds A-factor, an acyl-γ-butyrolactone (GBL), with high affinity. In the absence of A-factor, ArpA binds to specific sequences in the promoters of target genes, and prevents their expression. When ArpA binds A-factor, it loses its DNA-binding activity, and the target genes are expressed.

A-factor-like GBLs are a widespread family of molecules in streptomycetes, which accumulate outside the cells in culture; they appear to be freely exchanged between the cytoplasm and the medium. Only at high cell density does the concentration outside, and therefore inside, the cells become sufficient to cause detachment of cognate binding proteins (such as ArpA) from promoters. The result of this is that the target genes become active only at high cell density. Moreover, at least some of these target genes regulate sporulation and/or antibiotic production, processes which occur only in dense cultures.

The inventors have also discovered that the deduced amino acid sequence of the mmfL gene is very significantly similar to proteins which confer GBL production in other *Streptomyces* spp. (FIG. 3). It can be seen in FIG. 1 that the mmfL gene is located between the two repressor-encoding genes mmyR and mmfR, along with mmfP and mmfH.

Further, the inventors present experimental results, based on the insertion of a marker gene into the mmyG and mmfH genes, which show that mmyG and mmfH are selectively expressed at high cell density (FIG. 4). The gene chosen was xylE from a plasmid of pseudomonads (Bruton et al, 1991). The xylE gene product is the enzyme catechol oxygenase, which may be detected by colony staining (Ingram et al., 1989).

From sequence analysis, it newly appears that the mmyT, mmyO and mmyG genes are transcribed from a common promoter, within the non-coding region between mmfR and mmyT. Thus, the inventors suggest that all three genes of the mmyTOG region are selectively expressed at high cell density. Similarly, it newly appears that mmfL, mmfH and mmfP are transcribed from a common promoter, within the non-coding region between mmfL and mmfR, and that this promoter is similarly regulated.

Similar regulation of expression was obtained when xylE was inserted into the mmy . . . XCAPK transcription unit (FIGS. 4 and 5), indicating that the promoter for this region is similarly regulated.

Based on their studies, the inventors now provide a model for the regulation of methylenomycin production in *Streptomyces*. The products of the mmyR and/or mmfR genes, ArpA homologues, bind to the promoter(s) of gene(s) presumed to encode methylenomycin biosynthetic enzymes or positive regulators of methylenomycin biosynthesis, thereby preventing methylenomycin production. MmfL, the product of the mmfL gene, directs the synthesis of a GBL, which binds to the products of the mmyR and/or mmfL genes. At sufficiently high cell density (and hence sufficiently high mmfL-specified GBL concentration in the medium), this latter binding is sufficient to prevent binding of the mmyR and/or mmfR gene products to the promoter(s) whose activation is necessary for methylenomycin production. Included among these are the promoters of mmyTOG, mmfLHP and mmy . . . XCAPK. It is further deduced that the induction of the mmfLHP promoter forms a "gearing" system, amplifying the production of GBL, and "committing" the cells to uninhibited expression from the mmyTOG and mmy . . . XCAPK promoters.

As a result of further experiments, it is further suggested that the product of another gene, mmyB, is also involved in this commitment (see Example 4).

The inventors now predict from this model that disruption of the mmyR and/or mmfR genes will cause increased methylenomycin production, because loss of repressors releases target promoters from repression. Observations have confirmed this prediction and show that none of the mmyR, mmfP and mmfH genes is a positive regulator; that none of them encodes an essential biosynthetic enzyme for methylenomycin biosynthesis; and that mmyR acts negatively.

As a result of further experiments, the inventors also predict that an additional gene, mmyB, is also involved in the operation of the regulatory scheme. Observations reported in Example 4 have supported this prediction.

The inventors also believe that the presence of an extra copy of mmfL would cause increased methylenomycin production, since this should lead to increased GBL synthesis and hence more efficient lifting of repression. Observations have confirmed this prediction also.

The sequencing of the mmfL gene shows that it contains an unusual feature, namely the presence of a TTA codon (position shown in FIG. 1). TTA (=UUA in mRNA) is one of six codons which encode leucine. However, from the fact that there are fully viable mutant strains of Streptomyces which lack the ability to translate this codon, it is known that the TTA codon is not used in any essential genes of Streptomyces spp. Such mutants are defective in the bldA gene which directly encodes the transfer RNA responsible for recognising the UUA codon (Leskiw et al., 1991). Translation of mmfL mRNA into MmfL protein would therefore be severely impaired in a bldA mutant. Observations reported in Example 4 have strongly supported this prediction.

The present inventors also predict that there would be a failure of GBL production in a bldA mutant, which would lead to non-production of methylenomycin, since their model indicates that mmfL confers production of a GBL needed to relieve repression of methylenomycin synthesis. Observations reported in Example 4 have strongly supported this prediction.

Experiments are described herein in which an appropriately orientated foreign gene encoding an easily detectable enzyme (xylE) was inserted into different transcription units in the methylenomycin gene cluster. Expression of xylE was detected at high levels in, for example, bldA$^+$ strains carrying mmyG::xylE, mmfH::xylE or mmy . . . XCAPK::xylE fusions, but was undetectable in bldA mutants carrying the same fusions, confirming the prediction of the model.

The pattern of expression of catechol oxygenase in bldA$^+$ strains carrying mmyG::xylE, mmy . . . XCAPK::xylE or mmfH::xylE fusions was that early in growth there was no detectable activity, whereas later in growth the specific activity rose very sharply (FIG. 4), demonstrating that the promoter driving xylE expression is very specifically regulated.

For comparison when xylE was fused to the redX transcription unit for production of undecylprodigiosin, a different antibiotic, in the chromosome of *S. coelicolor*, much lower specific activity was obtained, albeit in different growth conditions (Guthrie and Chater, 1990). Thus the promoter driving mmyG::xylE expression is very strong, by comparison to those of genes for other *Streptomyces* antibiotics. Similarly strong expression is indicated for the promoters driving expression of mmyK and mmfH.

In continuing sequencing of the methylenomycin genes one other target TTA sequence for bldA action has been discovered, indicating that the TTA codon in mmfL may not be the sole reason for bldA-dependence of methylenomycin production. Observations have verified this prediction (see Example 4b).

From their model, the inventors teach that the insertion of a nucleic acid of interest (e.g. a gene or genes) into the mmyTOG region, in the correct orientation, and in the presence of the mmyR-mmf-mmyTOG region left of the insertion site, provides self-regulating, strong expression of the nucleic acid of interest specifically late in culture, to give a high level of expression only in conditions when the main growth phase has been completed (i.e. at high biomass and high mycelium density). This has four main advantages for the expression of the nucleic acid of interest: (1) reduced or no expression earlier in growth, avoiding toxic effects of some gene products on growth; (2) there is no requirement for an exogenously added inducer, avoiding various constraints on the culture medium or problems of the cost of adding inducers to large fermenters or of removing them from the desired end product; (3) the methylenomycin cluster, naturally present on a highly transmissible plasmid, is likely to have evolved to permit properly regulated expression in diverse *Streptomyces* hosts (see above), which is important commercially because virtually every antibiotic or other *Streptomyces* product made commercially involves a different strain; and (4) the expression is driven by a strong promoter, leading to high yield of the desired end product. Further experiments appear to indicate that the host strain used for expression should contain those mmy genes to the right of mmr, or at least the mmyB gene.

The inventors similarly teach that similar results could be obtained with the nucleic acid of interest inserted in the appropriate orientation into the mmy . . . XCAPK region, in the presence of the mmy . . . XCAPK region to the right of the insertion site and in the presence of the mmy . . . XCAPK promoter, or with the nucleic acid of interest inserted in the appropriate orientation into the mmfLHP region, in the presence of the mmfLHP region to the right of the insertion site and in the presence of the mmfLHP promoter.

Similar results may also be obtained with the nucleic acid of interest inserted in the appropriate orientation into the mmyBQE region, in the presence of the mmyBQE region to the right of the insertion site and in the presence of the mmyBQE promoter, or with the nucleic acid of interest inserted in the appropriate orientation into the mmyYF region, in the presence of the mmyYF region to the left of the insertion site and in the presence of the mmyYF promoter.

Furthermore, it is believed that certain regions of the 9.5 kb stretch which has been investigated are of greater importance than others. In particular, the model teaches that interplay between the products of the mmfR, mmyR, mmfL and mmyB genes and the promoters of the mmyTOG, mmy . . . XCAPK and mmfLHP regions is key to the regulation of methylenomycin production. Consequently, it is taught that the combination of the nucleic acid of interest and minimal regulatory portions which include an mmfR gene and/or an mmyR gene; an mmfL gene; an mmyB gene; and an mmyTOG promoter and/or an mmy . . . XCAPK promoter and/or an mmfLHP promoter and/or an mmyBQE promoter and/or an mmyYF promoter will also lead to increased expression of the nucleic acid of interest at higher cell density relative to lower cell density.

However, it is also contemplated that the mmfP and mmfH genes may be of importance in regulation of methylenomycin production, for example in some conditions their products may modify the structure of the GBL whose production is conferred by the mmfL gene, resulting in changes in the details of interactions between the GBL and the mmyR and/or mmfR gene products. Consequently these genes may also be present in the regulatory portion.

Moreover, having found that three different promoters of methylenomycin biosynthetic and positive regulatory genes are regulated in the same way, the inventors expect that other promoters of methylenomycin biosynthetic genes will also be similarly regulated.

In a first aspect, therefore, the present invention provides an expression cassette for the expression of a nucleic acid of interest, the expression cassette including:

a regulatory portion or portions including:
    a first regulatory element which includes either an mmyR gene encoding an MmyR polypeptide, or an mmfR gene encoding an MmfR polypeptide, or both;
    a second regulatory element which includes an mmfL gene encoding an MmfL polypeptide; and
    a promoter (the "repressible promoter"), the function of which is repressed by the expression product of the first regulatory element, that repression being alleviated or removed by a product, the production of which is conferred by the MmfL polypeptide, and
the nucleic acid of interest, in operative association with said promoter.

Such a construct represents the minimal expression cassette which may be predicted by the above model to cause expression of the nucleic acid of interest in Streptomyces at high cell density.

Preferably, the expression cassette is capable of expressing the nucleic acid of interest at increased levels in stationary phase cultures of Streptomyces compared to early exponential phase cultures.

Preferably the regulatory elements, promoter and nucleic acid of interest are provided on a single expression cassette, but it is contemplated that they may be provided separately, for example on two vectors which may be co-introduced into a desired host, or that one or more of the regulatory elements and promoter may be provided by the SCP1 plasmid.

Accordingly in this first aspect, the present invention also provides a set of nucleic acids for the expression of a nucleic acid of interest, the set of nucleic acids together including:

a regulatory portion or portions including:
    a first regulatory element which includes either an mmyR gene encoding an MmyR polypeptide, or an mmfR gene encoding an MmfR polypeptide, or both;
    a second regulatory element which includes an mmfL gene encoding an MmfL polypeptide;
    a promoter (the "repressible promoter"), the function of which is repressed by the expression product of the first regulatory element, that repression being alleviated or removed by a product, the production of which is conferred by the MmfL polypeptide, and
the nucleic acid of interest, in operative association with said promoter.

Preferably the set is an isolated set of nucleic acids.

Preferably both an mmyR gene and an mmfR gene will be provided in the regulatory portion(s) of this aspect.

Preferably an mmyB gene encoding an MmyB polypeptide will be provided within, or in addition to, the expression cassette or set of nucleic acids, as a mediator of the regulatory effects of the regulatory portion. In a preferred embodiment, the mmyB gene is incorporated into a third regulatory element of the regulatory portion(s). Preferably some or all of other mmy genes to the right of the mmr gene (as shown in FIG. 1e) are also provided.

The repression of the function of the repressible promoter by the expression product of the first regulatory element may be direct repression by the expression product, or it may arise from the absence of an activator which is itself repressed by the first regulatory element.

Preferably the regulatory portion(s) comprise at least a portion of the 9.5 kb newly sequenced stretch of nucleic acid as shown in FIG. 7, or a variant thereof.

Preferably, the mmyR gene encodes an MmyR polypeptide having the amino acid sequence of FIG. 8a (optionally excluding the first 6 listed amino acids). More preferably it comprises residues 1407 to 796 of FIG. 7, lower strand (optionally excluding residues 1407 to 1390).

Preferably, the mmfR gene encodes an MmfR polypeptide having the amino acid sequence of FIG. 8e. More preferably it comprises residues 4807 to 5451 of FIG. 7, upper strand.

Preferably, the first regulatory element also includes a promoter operatively linked to the mmyR or mmfR gene. In embodiments where both genes are present, they are preferably operatively linked to respective promoters. Still more preferably, the promoter to which the mmyR gene is linked is an mmyR promoter and/or the promoter to which the mmfR gene is linked is an mmfR promoter. Even more preferably the promoter to which the mmyR gene is linked comprises some or all of residues 1557 to 1390 of FIG. 7, lower strand (optionally excluding residues 1409 to 1390) and/or the promoter to which the mmfR gene is linked comprises some or all of residues 4613 to 4806 of FIG. 7, upper strand.

Preferably, the mmfL gene encodes an MmfL polypeptide having the amino acid sequence of FIG. 8d. More preferably, it comprises residues 4612 to 3551 of FIG. 7, lower strand.

Preferably, the second regulatory element also includes a promoter operatively linked to the mmfL gene. Still more preferably, the promoter to which the mmfL gene is linked is an mmfL promoter. Even more preferably the promoter to which the mmfL gene is linked comprises some or all of residues 4806 to 4613 of FIG. 7, lower strand.

It will be observed that the preferred promoters for mmfL and mmfR both comprise some or all of residues 4806 to 4613 of FIG. 7. This region is thought to include a bi-directional promoter for both these genes. Preferably the promoter(s) for mmfL and/or mmfR include a palindromic sequence having a high degree of sequence identity or complete sequence identity with a palindromic sequence having the half-site 5'-GG(T/C)CGGT(A/T) (T/C)G(T/G)-3' (SEQ ID NO: 1), which is the consensus sequence for binding of DNA by the ArpA protein. In this context high sequence identity preferably represents sequence identity at seven or more, more preferably 8 or more, 9 or more, or 10 or more corresponding positions within the half-site. More preferably the palindromic sequence has the half-site 5'-GGAAGGTATTA-3' (SEQ ID NO: 2) (or a variant thereof). In a particularly preferred embodiment, the regulatory portion comprises residues 3551 to 5451 of FIG. 7, upper strand (or a variant thereof).

Preferably the repressible promoter is a promoter of a methylenomycin biosynthetic or regulatory gene.

More preferably the repressible promoter comprises an mmyTOG promoter or an mmy . . . XCAPK promoter or an mmfLHP promoter or an mmyBQE promoter or an mmyYF promoter.

However, it is also thought that other promoters of methylenomycin biosynthetic genes may be regulated in the same way as mmyTOG, mmy . . . XCAPK and mmfLHP. Accordingly, the repressible promoter may comprise a promoter of any other methylenomycin biosynthetic gene which is regulated by the mmyR and/or mmfR genes and the mmfL gene, typically mediated by the mmyB gene.

Preferably the mmyTOG promoter comprises some or all of residues 5452 to 5675 of FIG. 7; upper strand.

Preferably the mmfLHP promoter comprises some or all of residues 4613 to 4806 of FIG. 7, lower strand.

The mmy . . . XCAPK, mmyBQE and mmyYF promoters remain to be accurately located. However, this may be accomplished routinely by sequencing and sequence analysis of, for example, the restriction fragments A4.2 and A3.13 (Chater and Bruton, 1983), which make available different parts of the mmy . . . XCAPK cluster, or by analysis of EMBL accession number AJ276673. It is thought that the mmy . . . XCAPK promoter comprises some or all of residues 15404 to 15977 of EMBL AJ276673 and that the mmyBQE promoter comprises some or all of residues 18892 to 19123 of EMBL AJ276673, or that the mmyBQEDX-CAPK genes are all transcribed from a single promoter which comprises some or all of residues 18892 to 19123 of EMBL AJ276673. It is thought that the mmyYF promoter comprises some or all of residues 18892 to 19123 of EMBL AJ276673.

Apart from the repressible promoter, the nucleic acid of interest is preferably not additionally in operative association with any exogenous promoter, i.e. any promoter which is not derived from (or a variant of) a promoter present in the methylenomycin gene cluster. For example, in preparing the expression cassette (or set of nucleic acids) according to this aspect of the invention, the nucleic acid of interest is preferably brought into operative association with the repressible promoter in the functional absence of any promoter with which it may have previously been associated (for example a promoter of a cloning vector).

Preferably, the mmyB gene encodes an MmyB polypeptide having the deduced amino acid sequence shown for this gene in EMBL AJ276673. More preferably, it comprises the complement of residues 18032 to 18892 of the nucleic acid sequence shown in EMBL AJ276673.

Preferably, the third regulatory element also includes a promoter operatively linked to the mmyB gene. Still more preferably, the promoter to which the mmyB gene is linked is an mmyB promoter. Even more preferably the promoter to which the mmyB gene is linked comprises some or all of residues 18892 to 19123 of EMBL AJ276673.

Since it is thought that they may be of importance in directing expression to high cell density cultures in some fermentation conditions, an mmfP gene and/or an mmfH gene, preferably both, are preferably included in the regulatory portion(s). However in some embodiments, in which an mmyLHP promoter is operatively linked to the nucleic acid of interest, one or more of these genes may be replaced or disrupted by the nucleic acid of interest.

When an mmyTOG promoter is used, at least part of at least one of an mmyT, an mmyO and/or an mmyG gene is suitably present in the regulatory portion, in operative association with the mmyTOG promoter. However, there may in particular be a 3' (right hand end) truncation of the mmyTOG coding region.

When an mmfLHP promoter is used, at least part of at least one of an mmfH and/or an mmfP gene is suitably present in the regulatory portion, in operative association with the mmfLHP promoter. However, there may in particular be a 3' (left hand end) truncation of the mmfLHP coding region. Preferably an intact mmfL gene is also in operative association with the same mmfLHP promoter.

When an mmy . . . XCAPK promoter is used, at least part of at least one of an mmyX, an mmyC, an mmyA, an mmyP, an mmyK gene, and/or an mmyD gene (mmyD is a co-transcribed gene located between mmyx and the putative mmy . . . XCAPK promoter) is suitably present in the regulatory portion, in operative association with the mmy . . . XCAPK promoter. However, there may in particular be a 3' (left hand end) truncation of the mmy . . . XCAPK coding region.

When an mmyBQE promoter is used, at least part of at least one of an mmyB, an mmyQ and/or an mmyE gene is suitably present in the regulatory portion, in operative association with the mmyBQE promoter. However, there may in particular be a 3' (left hand end) truncation of the mmyBQE coding region.

The same applies mutatis mutandis to the situation where an mmyBQEDXCAPK promoter is used.

When an mmyYF promoter is used, at least part of at least one of an mmyY and an mmyF gene is suitably present in the regulatory portion, in operative association with the mmyYF promoter. However, there may in particular be a 3' (right hand end) truncation of the mmyYF coding region.

The location and sequence of the individual genes with the mmyDXCAPK, mmyBQE (or mmyBQEDXCAPK) and mmyYF regions is given in EMBL AJ276673. The sequences of the corresponding promoters may be deduced by sequence analysis and/or routine experimentation on the basis of this sequence information (e.g. using DNase footprinting experiments).

Desirably, the nucleic acid of interest is inserted into the regulatory portion, preferably within an mmyT, mmyO or mmyG gene (when an mmyTOG promoter is used) or within an mmyD, mmyX, mmyC, mmyA, mmyP or mmyK gene (when an mmY . . . XCAPK promoter is used) or within an mmfH or mmfP gene (when an mmfLHP promoter is used) or within an mmyQ or mmyE gene (when an mmyBQE promoter is used) or within an mmyQ, mmyE, mmyD, mmyX, mmyC, mmyA, mmyP or mmyK gene (when an mmyBQEDXCAPK promoter is used) or within an mmyY or mmyF gene (when an mmyYF promoter is used).

The nucleic acid of interest may be inserted into the regulatory portion by means of homologous recombination (e.g. using a vector containing a fragment of the mmyTOG, mmy . . . XCAPK, mmyBQE, mmyBQEDXCAPK, mmyYF or mmfLHP coding region). Accordingly, the regulatory portion may contain an entire mmyTOG, mmy . . . XCAPK, mmyBQE, mmyBQEDXCAPK, mmyYF or mmfLHP coding region, which is interrupted by the nucleic acid of interest.

Preferably, the mmyT gene encodes an MmyT polypeptide having the amino acid sequence of FIG. 8f, or a variant thereof. More preferably, it comprises residues 5676 to 6401 of FIG. 7, upper strand.

Preferably the mmyO gene encodes an MmyO polypeptide having the amino acid sequence of FIG. 8g. More preferably, it comprises residues 6432 to 7553 of FIG. 7, upper strand.

Preferably, the mmyG gene encodes an MmyG polypeptide having the amino acid sequence of. FIG. 8*h*. More preferably, it comprises residues 7636 to 8817 of FIG. 7, upper strand.

Preferably, the mmfL gene encodes an MmfL polypeptide having the amino acid sequence of FIG. 8*d*. More preferably, it comprises residues 3551 to 4612 of FIG. 7, lower strand.

Preferably, the mmfH gene encodes an MmfH polypeptide having the amino acid sequence of FIG. 8*c*. More preferably, it comprises residues 3554 to 2352 of FIG. 7, lower strand.

Preferably, the mmfP gene encodes an MmfP polypeptide having the amino acid sequence of FIG. 8*b*. More preferably, it comprises residues 3554 to 1558 of FIG. 7, upper strand.

The same applies, mutatis mutandis, to the mmyDX-CAPK, mmyBQE and mmyYF genes, based on the respective amino acid and nucleic acid sequences given in EMBL AJ276673.

Preferably the nucleic acid of interest is heterologous, i.e. having a sequence not present in or derived from the 9.5 kb stretch of newly sequenced DNA, more preferably not present in or derived from the methylenomycin biosynthetic gene cluster.

In one preferred embodiment, the regulatory portion(s) include(s) an mmfR gene and an mmfL gene, with the mmfL promoter as the repressible promoter (for example the nucleic acid may be inserted into the mmfH or mmfP gene, downstream of mmfL under the control of the mmfLHP promoter).

In a more preferred embodiment, the regulatory portion(s) include(s) an mmfR gene, an mmfL gene and an mmrR gene, with the mmyB promoter as the repressible promoter (for example the nucleic acid may be inserted into the mmyB, mmyQ or mmyE gene, under the control of the mmyB promoter).

In a still more preferred embodiment, the regulatory portion(s) include(s) an mmfR gene, an mmfL gene, and mmyR gene, with the mmyTOG promoter, the mmyDX-CAPK or the mmyYF promoter as the repressible promoter, such regulatory portion(s) being suitable for use in the presence (either as a third regulatory portion or as another part of the expression system) of an mmyB gene.

In a highly preferred embodiment, the regulatory portion(s) may include nucleic acid having the sequence from residue 796 to a residue between 5676 and 8817 (inclusive) of FIG. 7 (or a variant thereof). When double stranded, this nucleic acid contains mmyR, mmfP, mmfH, mmfL and mmfR genes and intergenic regions between those genes and at least a region containing an mmyTOG promoter (i.e. the region upstream of mmyT), and optionally some or all of an mmyTOG coding region. The nucleic acid of interest may then be inserted into or downstream of the mmyTOG region (or part thereof) in operative association with the mmyTOG promoter.

In another highly preferred embodiment, the regulatory portion(s) may include nucleic acid having the sequence from residue 796 to residue 5451 (inclusive) of FIG. 7 (or a variant thereof). When double stranded, this nucleic acid contains mmyR, mmfP, mmfH, mmfL and mmfR genes and intergenic regions between those genes. The nucleic acid of interest may then be inserted into the mmfHP region in operative association with the mmfLHP promoter.

It is contemplated that elements contributing to promoter activity (e.g. enhancer elements) may lie outside the non-coding intergenic regions specified above. Accordingly, it is particularly preferred that the intergenic promoter regions are located in their natural immediate context, i.e. between genes (or parts of genes) which normally flank them. Accordingly embodiments using a cassette containing an intact mmyR-mmf-mmyTOG region, optionally with a disruption of or 3' (right-hand end) truncation of the mmyTOG region, are particularly preferred.

In a second aspect, the present invention provides a vector comprising an expression cassette according to the first aspect of the invention. Further it provides a set of vectors comprising a set of nucleic acids according to the first aspect of the invention.

Suitable vectors comprising nucleic acid for introduction into bacteria can be chosen or constructed, containing appropriate additional regulatory elements if necessary, including additional promoters, terminator fragments, enhancer elements, marker genes and other elements as appropriate. Vectors may be plasmids, viral e.g. "phage", or "phagemid", as appropriate. For further details see, for example, Sambrook et al, (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. (1992). Many aspects of the employment of these techniques in the context of *Streptomyces* spp. are described in detail in Hopwood et al (1985) and Kieser et al (2000). The disclosures of Sambrook et al, Ausubel et al, Hopwood et al and Kieser et al are all incorporated herein by reference for these and all other purposes.

In a third aspect, the present invention provides an expression system comprising an expression cassette or set of nucleic acids according to the first aspect of the invention and an expression system comprising a vector according to the second aspect of the invention.

Preferably the expression system is a host cell, although cell-free expression systems are also contemplated. Preferably the host cell is a bacterium, more preferably an actinomycete, further preferably a streptomycete. In particular, it has been shown (see Examples) that the invention can be applied successfully in streptomycete strains other the *S. coelicolor*, as expected on the basis of the transmissibility of the plasmid SCP1.

Preferably the expression system (usually a native or genetically modified host cell) contains an mmyB gene, more preferably as an additional part of the vector system used to introduce the expression cassette/set f nucleic acids. However, it is also contemplated that the mmyB gene may be present e.g. as part of the host cell genome and/or on a plasmid, e.g. SCP1 or pSV1 also present within the expression system. This is a less preferred embodiment as other methylenomycin gene promoters may sequester mmyB gene product, reducing its effectiveness in mediating expression from the expression cassette/set of nucleic acids.

In one preferred embodiment, the expression system lacks the ability to translate the codon TTA (UUA in mRNA), and the expression cassette, set of nucleic acids or vector(s) lacks TTA codons, and/or has been modified to eliminate one or more (preferably all) naturally occurring TTA codons. For example the expression system is preferably a cell of a bldA mutant strain of *Streptomyces* and the expression cassette preferably contains a variant of the mmfL gene in which the naturally occurring TTA codon has been altered (e.g. by site-directed mutagenesis) into another leucine-encoding codon. Preferably the mmyB gene included in this system (whether as part of an expression cassette or part of the host cell genome or on a plamsid also present in the system) has also been similarly altered so that its TTA codon has been changed to another leucine-encoding codon (see Example 10). This provides the advantage, particularly in *Streptomyces* spp., that expression of the nucleic acid of interest can be achieved with reduced expression of other products (for example antibiotics) which would otherwise also be expressed at high cell density via bldA-dependent mechanisms; i.e. this system provides a clean background for expression of the nucleic acid of interest. One or more TTA codons are present in the biosynthetic gene clusters for most streptomycete antibiotics, particularly in pathway-specific regulatory genes. TTA codons should not be present in genes whose expression is being carried out in a bldA mutant host. In some circumstances it may be necessary to use site-directed mutagenesis to convert a TTA codon to another leucine codon.

In another preferred embodiment the number of repressible promoters present in the expression system is limited. This may reduce expression-limiting sequestration of mmyB gene product by promoters other than the repressible promoter controlling expression of the nucleic acid of interest. Such limitation may involve the absence from the expression system of the SCP1 plamid and/or the pSV1 plasmid (though in such cases the mmyB gene is preferably otherwise present in the expression system). Additionally or alternatively, the expression cassette/set of nucleic acids may lack repressible promoters other than the promoter controlling expression of the nucleic acid of interest (however, promoters controlling expression of other genes of the expression cassette/set of nucleic acids may for this purpose be regarded as not being repressible promoters, e.g. the mmyTOG promoter may control the expression of the nucleic acid of interest and the mmfL and mmyB genes may be controlled by their native promoters). Lacking may be relative (i.e. there are fewer repressible promoters than in the native methylenomyin cluster), substantial or complete.

The introduction of the expression cassette, set of nucleic acids or vector(s) into a host cell, which may (particularly for in vitro introduction) be generally referred to without limitation as "transformation", may employ any available technique. For bacterial cells, suitable techniques may include calcium chloride transformation, polyethyleneglycol assisted transformation, electroporation, conjugation and transfection or transduction using bacteriophages.

In a fourth aspect, the present invention provides a method of expressing a nucleic acid of interest, the method comprising providing a host cell (or other expression system) according to preferred embodiments of the third aspect and culturing the host cell, so as to express the nucleic acid of interest.

Preferably the nucleic acid of interest is expressed substantially only when the host cell culture reaches high cell density, more preferably at or close to the stationary phase of host cell culture. Cell cultures at or close to stationary phase may have $OD_{650}$ values in the range of 1-20.

Known methods of culturing cells are well known in the art, for example from Sambrook et al (1989), Ausubel et al (1992), and (in particular for *Streptomyces* spp.) Hopwood et al (1985) and Kieser et al (2000).

In a fifth aspect, the present invention provides a method of expressing a nucleic acid of interest, the method comprising:
 providing in an expression system a regulatory portion or portions as defined in the first aspect;
 providing in the expression system the nucleic acid of interest;
 operatively associating the nucleic acid of interest with the repressible promoter of the regulatory portion(s); and
 expressing the nucleic acid of interest in the expression system.

The steps of the method need not be performed in the order recited. In particular, the operative association may occur prior to introduction regulatory portion(s) and nucleic acid of interest into the expression system.

The preferred features specified for the regulatory portion(s) in the context of the first aspect of the invention may also be present in the regulatory portion(s) used in this aspect. Preferably the expression system is a cell, more preferably a bacterium, further preferably an actinomycete and most preferably a streptomycete. Preferably the expression system contains an mmyB gene which may be introduced together with the regulatory cassette. The cell is preferably cultured for expression of the nucleic acid of interest.

The nucleic acid of interest may be brought into operative association with the repressible promoter in a variety of ways. For example, the nucleic acid of interest may be inserted into a nucleic acid molecule which contains the repressible promoter, downstream of the repressible promoter (FIGS. 6c and 6d). In a preferred example, the repressible promoter is an mmyTOG promoter and the insertion site is within an mmyTOG region.

Alternatively, the regulatory portion may be inserted into nucleic acid containing the nucleic acid of interest, for example by homologous recombination (FIG. 6b). Thus a fragment from the 5' end of the nucleic acid of interest may be included downstream of and in operative association with the repressible promoter to permit homologous recombination of the regulatory portion into the nucleic acid of interest.

This method may be advantageously used in a bldA mutant *Streptomyces* or other actinomycete host cell, with a regulatory portion or portions (and preferably mmyB gene) lacking TTA codons, to regulate the expression of a nucleic acid of interest which is native to the host cell and which preferably confers production of an antibiotic. This embodiment has the advantage that other antibiotics encoded by the host cell will generally not be expressed, since the pathway-specific regulatory genes for production of such other antibiotics in Streptomyces typically include a TTA codon. For example, in one preferred expression system, *S. coelicolor* A(3)2, major pathway-specific regulatory genes of each of two known chromosomally located antibiotic pathways contain TTA codons, and a bldA mutant therefore makes neither of these antibiotics in typical culture media (Fernandez-Moreno et al. 1991, White and Bibb 1997).

The expression products of the nucleic acids of interest of the fourth and fifth aspects may be collected and purified. This may be achieved by conventional methods. See for example McDaniel et al. (1993).

Where the nucleic acid of interest is for example a biosynthetic gene cluster, both the end product of the biosynthesis and the biosynthetic enzymes themselves may be regarded to be the expression product, but more usually the end product will be regarded to be the expression product.

In a sixth aspect, therefore, the present invention provides an expression product produced according to the method of either of the fourth or fifth aspects of the invention.

The nucleic acid of interest may be any nucleic acid. Preferred nucleic acids are genes, the expression of which is desired, or gene clusters, for example which encode the enzymes necessary for the biosynthesis of e.g. antibiotics. Gene clusters may have a plurality of genes within the same transcriptional promoter, so as to allow expression of all genes of the cluster from the repressible promoter. Alternatively, the nucleic acid of interest may be an unknown nucleic acid which it is desired to investigate, for example nucleic acid derived from a sample e.g. of soil.

In a seventh aspect, the present invention provides a nucleic acid molecule comprising an mmyR and/or an mmfR gene, an mmfL gene, and a repressible promoter, all as defined in the first aspect, wherein the molecule is capable of regulating the expression of a nucleic acid of interest when that nucleic acid is arranged in operative association with the repressible promoter.

The same preferred and optional features apply to this aspect as they apply to the first aspect.

Preferably the molecule of this aspect is other than pIJ519, as disclosed in Chater and Bruton (1985) and/or does not consist of or include the 350 kb SCP1 plasmid of *Streptomyces coelicolor* and/or the pSV1 plasmid of *Streptomyces violaceoruber*. However, such plasmids may be used in conjunction with the molecule of this aspect (e.g. to supply an mmyB gene).

Preferably, the molecule consists essentially of an approximately 4.8 to 8 kb stretch of DNA including mmyR, mmfP, mmfH, mmfL and mmfR genes and at least a portion of at least one of an mmyT gene, an mmyO gene and an mmyG gene. More preferably, the molecule includes the entire mmyT and mmyO genes and at least a portion of the mmyG gene.

Preferably the molecule consists essentially of the nucleic acid having the sequence from residue 796 to a residue between 5676 and 8817 (more preferably between 7636 and 8817) of FIG. 7.

In an alternative embodiment, the molecule consists essentially of a stretch of nucleic acid including mmyR, mmfP, mmfH, mmfL and mmfR genes in combination with a stretch of nucleic acid including an mmy . . . XCAPK promoter and at least a portion of at least one of an mmyD gene, an mmyX gene, an mmyC gene, an mmyA gene, an mmyP gene, an mmyK gene.

In an alternative embodiment, the molecule consists essentially of an approximately 5 kb stretch of DNA including mmyR, mmfP, mmfH, mmfL and mmfR genes.

In addition to the defined stretches of DNA, the molecule preferably comprises an mmyB gene. p In an eighth aspect, the present invention provides a nucleic acid molecule consisting essentially of one or more of an mmyB gene in which a naturally occurring TTA codon has been changed into another (preferably leucine encoding) codon, an mmyR gene, an mmfP gene, an mmfH gene, an mmfL gene (preferably in which a naturally occurring TTA codon has been changed into another (preferably leucine encoding) codon), an mmfR gene, an mmyT gene, an mmyO gene, and an mmyG gene, optionally with a respective upstream region or respective upstream regions. Where present, the upstream region(s) may comprise promoters (preferably as previously defined) for the genes. Where two or more genes are present, an upstream region for one or more of those genes may be provided in an intergenic region.

The genes may be as previously defined.

In a ninth aspect, the present invention provides the use of one or more nucleic acid molecules as defined in any one of the seventh or eighth aspects, in or for the regulation of expression of a nucleic acid of interest in an expression system. p In a tenth aspect, the present invention provides a polypeptide encodable by one of the following genes: an mmyR gene, an mmfP gene, an mmfH gene, an mmfL gene, an mmfR gene, an mmyT gene, an mmyO gene and an mmyG gene. Preferably the polypeptide is substantially isolated from other proteins with which it is naturally associated.

The polypeptide preferably has an amino acid sequence as shown in one of FIGS. 8a to 8h. However, this aspect also provides polypeptides which are variants of those amino acid sequences.

In an eleventh aspect, the present invention provides a vector including a nucleic acid according to the seventh or eighth aspect. In embodiments of the seventh and eighth aspects in which the nucleic acid lacks a promoter or promoters for the gene or genes it contains, the vector preferably includes a promoter in operative association with that gene or those genes.

In a twelfth aspect, the present invention provides an expression system containing one or more nucleic acids according to the seventh or eighth aspects and an expression system containing a vector according to the eleventh aspect.

Preferably the expression system is a cell. Where it is desired merely to express the polypeptide encoded by the nucleic acid, rather than for example to regulate the expression of another nucleic acid of interest, any appropriate cell may be used (e.g. a standard *E. coli* overexpression system). See for example Sambrook et al (1989) and Ausubel et al (1992). Otherwise, bacterial, actinomycete and streptomycete cells are preferred as previously indicated.

In a thirteenth aspect, the present invention provides a method of producing a polypeptide according to the tenth aspect, the method comprising producing the polypeptide in an expression system according to the twelfth aspect.

The polypeptide may be purified from the expression system by conventional methods.

References herein to genes, coding regions and nucleic acids are not to be interpreted as being restricted to genes, coding regions and nucleic acids having the specific nucleic acid sequences disclosed herein or in EMBL AJ276673. Rather, genes, coding regions and nucleic acids having variants of those sequences are also included. Genes, coding regions and nucleic acids having such specific sequences are preferred embodiments. Thus, for example, a reference to "an mmfR gene" is not to be interpreted as being restricted to a gene having the sequence from residue 4807 to residue 5451 of FIG. 7, but also includes variants.

Similarly, references herein to polypeptides are not to be interpreted as being restricted to polypeptides having the specific amino acid sequences disclosed herein or in EMBL AJ276673. Rather, polypeptides having variants of those sequences are also included. Polypeptides having such specific sequences are preferred embodiments. Thus, for example, a reference to "an MmfR polypeptide" is not to be interpreted as being restricted to a polypeptide having the amino acid sequence shown in FIG. 8e, but also includes variants.

References herein to promoters are not to be interpreted as being restricted to nucleic acids having the sequence of all or part of a specific intergenic region disclosed herein or in EMBL AJ276673. Again, promoters having variants of those intergenic sequences are also included and the specific intergenic sequences (or parts thereof) are preferred embodiments. Thus, for example, a reference to "an mmyTOG promoter" is not to be interpreted as being restricted to the specific mmyTOG promoter disclosed herein (i.e. a nucleic acid having all or part of the sequence from residues 5452 to 5675 of FIG. 7, upper strand), but also includes variants.

In all cases, where a preferred embodiment of a gene, nucleic acid, polypeptide or promoter is defined by reference to a specific sequence, the invention in its broader sense is intended to include embodiments having variants of that specific sequence.

The term "variant" as used herein in relation to a particular nucleic acid (the reference nucleic acid) denotes: any nucleic acid having a sequence which is different from that of the reference nucleic acid, but which is its complement or which shows significant nucleic acid sequence identity with, or hybridisation under stringent conditions to, the reference nucleic acid or its complement or a fragment of the reference nucleic acid or its complement; or any nucleic acid which encodes an amino acid sequence having significant amino acid sequence identity with the amino acid sequence encoded by the reference nucleic acid, or a fragment of that nucleic acid. The term "variant" also refers to nucleic acids which differ from each other due only to the degeneracy of the genetic code, and which therefore encode identical deduced amino acid sequences.

The term "variant" as used herein in relation to a particular polypeptide (the reference polypeptide) denotes: any polypeptide having an amino acid sequence which is different from, but which shows significant amino acid sequence identity with, the amino acid sequence of the reference polypeptide, or a fragment of that polypeptide.

Unless otherwise specified, significant amino acid sequence identity is preferably at least 80%, more preferably 85%, 90% or 95%, still more preferably 98% or 99% and/or significant nucleic acid sequence identity is preferably at least 50%, more preferably 60%, 70%, 80% or 90%, still more preferably 95%, 98% or 99%.

Significant amino acid sequence identity is preferably shown between the variant polypeptide (or a portion thereof) and a fragment of at least 10 amino acids of the reference polypeptide, more preferably a fragment of a least 20, 30 or 40 amino acids, still more preferably a fragment of 60, 80 or 100 amino acids, more preferably the entire reference polypeptide.

Significant nucleic acid sequence identity is preferably shown between the variant nucleic acid (or a portion thereof) and a fragment of at least 30 residues of the reference nucleic acid, more preferably a fragment of a least 60, 90 or 120 residues, still more preferably a fragment of 180, 240 or 300 residues, more preferably the entire reference nucleic acid.

In relation to variants of the specific mmyR gene disclosed herein, or of its product, MmyR, significant amino acid sequence identity is preferably shown with residues 40 to 49 of FIG. 8a, more preferably residues 38 to 49, more preferably residues 38 to 56, more preferably residues 38 to 59, still more preferably residues 21 to 59, still more preferably residues 3 to 59 and/or significant nucleic acid sequence identity is preferably shown with corresponding portions of FIG. 7 which encode the above amino acid residues.

In relation to variants of the specific mmfR gene disclosed herein, or of its product, MmfR, significant amino acid sequence identity is preferably shown with residues 61 to 70 of FIG. 8e, more preferably residues 59 to 70, more preferably residues 59 to 77, more preferably residues 59 to 80, still more preferably residues 42 to 80, still more preferably residues 24 to 80 and/or significant nucleic acid sequence identity is preferably shown with corresponding portions of FIG. 7 which encode the above amino acid residues.

In relation to variants of the specific mmfL gene disclosed herein, or of its product, MmfL, significant amino acid sequence identity is preferably shown with residues 77 to 87 and/or residues 240 to 255 of FIG. 8d, more preferably residues 77 to 95 and/or residues 231 to 255, more preferably residues 77 to 107 and/or residues 223 to 255 and/or significant nucleic acid sequence identity is preferably shown with corresponding portions of FIG. 7 which encode the above amino acid residues.

"Percent (%) amino acid sequence identity" is defined as the percentage of amino acid residues in a candidate sequence that are identical with the amino acid residues in the sequence with which it is being compared, after aligning the sequences and introducing gaps, if necessary, to achieve the maximum percent sequence identity, and not considering any conservative substitutions as part of the sequence identity. The % identity values used herein are generated by WU-BLAST-2 which was obtained from Altschul et al. (1996); http://blast.wustl/edu/blast/README.html. WU-BLAST-2 uses several search parameters, most of which are set to the default values. The adjustable parameters are set with the following values: overlap span=1, overlap fraction=0.125, word threshold (T)=11. The HSPS and HSPS2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region, multiplied by 100. The "longer" sequence is the one having the most actual residues in the aligned region (gaps introduced by WU-BLAST-2 to maximize the alignment score are ignored).

"Percent (%) nucleic acid sequence identity" is defined as the percentage of nucleotide residues in a candidate sequence that are identical with the nucleotide residues in the sequence under comparison. The identity values used herein were generated by the BLASTN module of WU BLAST-2 set to the default parameters, with overlap span and overlap fraction set to 1 and 0.125, respectively.

In relation to variants of the promoters used in the present invention, nucleic acid sequence identity is preferably assessed over a sequence of at least 30 residues, more preferably 40 or 50 residues, still more preferably 60 residues. Thus, for example, preferred variants of the embodied mmyTOG promoter may have sequences which show 80% (or more) sequence identity over a 30 (or more) residue sequence within residues 5452 to 5675 of FIG. 7, upper strand.

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

When a nucleic acid of interest is in "operative association" with a promoter, the promoter is able to direct transcription of the nucleic acid of interest in an appropriate expression system, with the nucleic acid of interest in the correct reading frame for translation. Preferably when a nucleic acid of interest is in operative association with a promoter, the transcript of the nucleic acid of interest contains an appropriately located ribosome binding site for expression in an appropriate expression system of the polypeptide encoded by the nucleic acid of interest. See for example Sambrook et al. (1989) and Ausubel et al. (1992).

Variants of the genes, coding regions, nucleic acids, polypeptides and promoters specifically disclosed herein preferably have the same function as those specifically disclosed. In relation to the mmyR, mmfR and mmfL genes such function may be encoding an MmyR, MmfR and MmfL polypeptide, respectively; in relation to the MmyR, MmfR and MmfL polypeptides and the repressible promoter (e.g. the mmyTOG promoter, the mmy . . . XCAPK promoter or the mmfLHP promoter) such function may be the ability to interact with each other according to the model proposed above.

As used herein "mmyTOG" denotes nucleic acid including MmyT, mmyO and mmyG genes. The same applies mutatis mutandis to "mmy . . . XCAPK", the dots indicating the previously unidentified mmyD gene upstream of mmyX in the same transcription unit, and possibly the mmyB, mmyQ and mmyE genes, although these may form a separate transcription unit under the control of a different (mmyBQE) promoter. "mmyBQE" denotes nucleic acid including mmyB, mmyQ and mmyE genes. "mmyBQEDXCAPK" denotes nucleic acid including mmyBQE and mmyDX-CAPK. "mmyYF" denotes nucleic acid including mmyY and mmyF genes. "mmf" denotes nucleic acid including mmfP, mmfH, mmfL and mmfR genes. "mmfLHP" denotes nucleic acid including mmfL, mmfH, and mmfP genes. "mmyR-mmf-mmyTOG" denotes nucleic acid including an mmyR gene and mmf and mmyTOG. "mmy . . . XCAPK promoter" may be a promoter which controls the transcription of mmyBQEDXCAPK, or a promoter which controls the transcription of mmyDXCAPK only.

The invention, in its various aspects, will now be described in detail, with reference to the following figures, in which:

FIG. 1 shows the origin of the regulatory portion.
(a) The genome of *Streptomyces coelicolor* A3 (2) consists of a linear chromosome and two plasmids—the circular SCP2 and the linear SCP1.
(b) The methylenomycin production genes form a large gene cluster on the SCP1 plasmid (Chater and Bruton, 1985; Redenbach et al., 1998).
(c) About 25 kb of DNA includes regulatory, resistance and biosynthetic genes associated with methylenomycin production.
(d) The leftmost ca. 8 kb of the gene cluster comprises regulatory portion of the present invention, i.e. genes involved negatively and positively in regulating levels of methylenomycin production, and promoters under the control of those regulatory genes (it also includes other genes which are transcribed from these promoters).
(e) DNA to the right of the regulatory portion shown in (d), comprising the mmr (methylenomycin resistance) gene and genes further to the right, indicating the location of mmyB.

FIG. 2 shows a comparison of the products of methylenomycin regulatory genes with GBL-binding proteins from various *Streptomyces* spp. The products of mmyR (mmyrep, SEQ ID NO: 12) and mmfR (mmyrep2, SEQ ID NO: 11) are aligned with GBL-binding proteins associated with the production of virginiamycin (bara, SEQ ID NO: 9; barb, SEQ ID NO: 3), streptomycin (arpa, (SEQ ID NO: 10) and showdomycin and mimimycin (fara, (SEQ ID NO: 7). Other probable GBL-binding proteins from *S. coelicolor* A3(2) (cpra, (SEQ ID NO: 5; cprb, SEQ ID NO: 6; scbr, SEQ ID NO: 8) and the jadomycin biosynthesis gene cluster (jadr2, SEQ ID NO: 4) are also shown.

FIG. 3 shows that the product of mmfL (abbreviated here as mmy, SEQ ID NO: 17) is homologous with *Streptomyces* proteins implicated in the biosynthesis of GBLs. The latter proteins are for biosynthesis of A-factor (afsa, SEQ ID NO: 13), a GBL of *S. coelicolor* (scba, SEQ ID NO: 14), virginiae butanolide (barx, SEQ ID NO: 15) and IM-2 (farx, SEQ ID NO: 16).

In FIGS. 2 and 3, dots (".") denote the absence of an amino acid at that position, or the insertion of a gap for optimal sequence alignment and asterisks. ("*") denote the end of an amino acid sequence.

FIG. 4a shows the expression of a foreign gene (xylE) from an expression cassette which comprises the regulatory portion and the foreign gene.
Lower panel: organisation of the methylenomycin gene cluster in a strain engineered to express xylE from the transcription unit containing mmyG. The vector KC861 (Bruton et al, 1991) was engineered to contain the PstI fragment C2.18 (Chater and Bruton, 1983) which is now known to extend from within mmyT to within mmyG: the insert permitted integration of the phage in the configuration indicated. mmyG' and mmy'T denote 3' and 5' truncated copies of those genes, respectively.
Upper panel: time course for catechol oxygenase activity in a strain (based on J1507: Bruton and Chater, 1983) carrying the fusion illustrated. Samples grown on cellophane membranes overlaid on R2YE were harvested after the indicated culture times, and extracts were made and assayed as in Guthrie and Chater (1990).

FIG. 4b shows the expression of a foreign gene (xylE) by fusing the foreign gene to different transcription units in the methylenomycin biosynthesis cluster. The fusions were made exactly as in FIG. 4a (lower panel), but with reg or A3.13 fragments (FIG. 9) replacing the C2.18 fragment.
Upper panel: fusion to the mmfLHP transcription unit via the reg fragment;
Lower panel: fusion to the mmy . . . XCAPK transcription unit via fragment A3.13.

FIG. 5 summarises the results of a Southern blot, demonstrating the extensive deletion of methylenomycin biosynthetic DNA from the R333 mutant. The probe, pIJ518 (Chater and Bruton, 1985) contains a large segment from the centre of the methylenomycin cluster. In a R333 digest (not shown), most of the PstI fragments are missing. Also shown is the organisation of genes within the methylenomycin biosynthetic gene cluster and to the right of the newly sequenced region. Also shown is an EcoRI segment of SCP1 DNA which, when sub-cloned and introduced into an SCP1⁻ *S. coelicolor* host, stimulated methylenomycin production by an adjacent culture of the indicator "convertor" strain R39 described by Kirby and Hopwood (1977).

FIG. 6, parts *a-d* show examples of situations in which the regulatory portion and/or expression cassette could be used to enhance production of useful products. See text for explanations. Preferably in parts b, c and d, either the host strain used contains the mmyB gene, or the mmyB gene is present in the vector containing the expression cassette.

FIG. 7 shows the entire double-stranded sequence of an approximately 9.5 kb stretch of nucleic acid from the SCP1 plasmid, containing the mmyR, mmfP, mmfH, mmfL, mmfR, mmyT, mmyO, mmyG and mmyJ genes and the start of the mmr (methylenomycin resistance) gene. Some restriction sites are shown. The top strand is SEQ ID NO: 18 and the bottom strand is SEQ ID NO: 19. Deduced start and end residues of the genes are as follows:

| Gene | Strand | Starts at residue number | Ends at residue number |
|---|---|---|---|
| MmyR | bottom | 1389 or 1407 | 796 |
| MmfP | bottom | 2352 or 2355 | 1558 |
| MmfH | bottom | 3554 | 2352 |
| MmfL | bottom | 4612 | 3551 |
| MmfR | top | 4807 | 5451 |
| MmyT | top | 5676 | 6401 |
| MmyO | top | 6432 | 7553 |
| MmyG | top | 7636 | 8817 |
| MmyJ | bottom | 9115 or 9151 | 8780 |
| Mmr | top | 9333 | not shown |

In the figure:
← denotes the start of a gene;
[ denotes the end of a gene; and
* denotes one of two possible start sites for a gene.

FIG. 8, parts a-h show the deduced amino acid sequences of the mmyR (SEQ ID NO: 12), mmfP (SEQ ID NO: 20), mmfH (SEQ ID NO: 21), mmfL (SEQ ID NO: 17), mmfR (SEQ ID NO: 11), mmyT (SEQ ID NO: 221), mmyO (SEQ ID NO: 23), and mmyG (SEQ ID NO: 24) genes, respectively.

FIG. 9 shows restriction sites flanking DNA fragments used to guide insertion of foreign DNA (such as xylE; FIG. 4) into the mmfHLP, mmyTOG, and mmy . . . XCAPK gene clusters (information from Chater and Bruton, 1993 and 1995, and FIG. 7). Only relevant sites are shown.

FIG. 10 shows the restriction sites used in a restriction analysis of KC861::C2.18 phages to determine orientation of the C2.18 insert. P=PstI, B=BamHI, S$_f$=SstI, Bg=BglII, r=right hand end, l=left hand end. Only relevant sites are shown.

FIG. 13 shows in part a the construction of pG-UP. Part b shows the preferred form, pG-UP*, which contains mmvB. The HindIII site of the illustrated version of pG-UP is used to introduce mmyB in a form that leaves a unique HindIII site between the expression cassette and mmyB.

FIG. 14 shows the use of pG-UP for the expression of the J21 gene set. Numbers on primers (forward: SEQ ID NO: 25; SEQ ID NO: 26) refer to base positions in FIG. 7.

Figure 15:
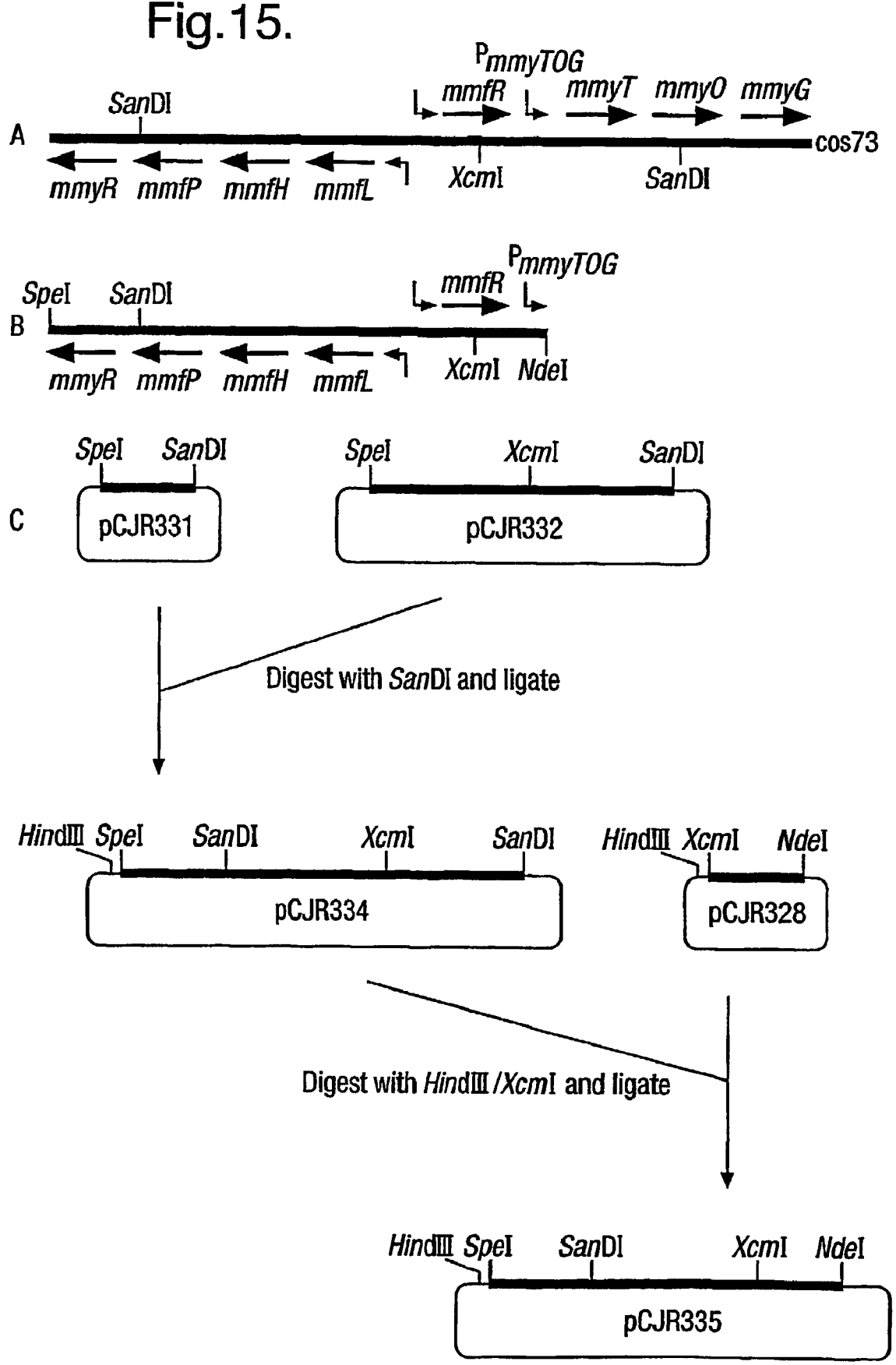

FIG. 15 shows in part a a fragment of cosmid cos73, containing the genes from mmyR to mmyG; part b shows this region engineered to terminate with the mmyTOG promoter, for use to control expression of a nucleic acid of interest; and part c shows the construction strategy

EXAMPLE 1

High Levels of Expression of a Foreign Gene Under the Control of Promoters in the Methylenomycin Biosynthetic Gene Cluster In order to determine expression levels at different points in the methylenomycin biosynthetic gene cluster (here termed the mmy cluster), derivatives of bacteriophage C31 containing the foreign gene xylE (a gene originating from Pseudomonas: Zukowski et al., 1983) were used to place xylE in defined positions and orientations within the mmy cluster contained in S. coelicolor strains J1507 (which contains the mmy cluster within SCP1$^{NF}$, a chromosomally integrated copy of SCP1; Bruton and Chater, 1983), or J1506 (a derivative of J1501 (Chater et al. 1982) which has an autonomous copy of SCP1).

Because KC861, the vector used, lacks the attP site normally used by C31 to permit its integration into the host chromosome during the establishment of lysogeny, it cannot form a prophage by the normal route (Bruton et al., 1991). It is, however possible to provide an alternative integration route by inserting a piece of Streptomyces host DNA into KC861, so that homologous recombination can integrate the prophage at the corresponding position in the host's DNA. Such events, which are quite rare, can be detected if the prophage carries a selectable resistance gene such as vph (viomycin resistance) or tsr (thiostrepton resistance) (Chater & Bruton, 1983; Bruton et al., 1991). In the present case, the mmy inserts placed in KC861 permitted the vector to integrate into particular positions in the mmy DNA of SCP1$^{NF}$ in J1507 or of SCP1 in J1506, with orientations that depended on the orientation of the insert in the vector. pBR327 and pBR322 recombinants (Chater & Bruton, 1983, 1985) were the DNA source for cloning the fragments reg, C2.18, mmr, A4.2 and A3.13 (FIG. 9) into the BamHI site of KC861. The reg fragment was a SstI-BglII subfragment of a larger insertion in pIJ519 (Chater and Bruton, 1985). The other four fragments had PstI boundaries. In order to provide them with BamHI compatible ends, they were introduced into the E. coli plasmid pIJ2925 (Janssen and Bibb, 1993). The mmy inserts were separated from the pBR327/322 vectors by digestion with PstI (or SstI and BglII for reg) and gel electrophoresis and were then ligated to suitably cut pIJ2925. JM101 was transformed with the ligations. The plasmid-host combination allowed blue/white screening for recombinants. For each fragment plasmid DNA of several white colonies was examined by BglII digestion to show whether it contained the insertion. A second enzyme was used to determine its orientation in relation to the polylinker of pIJ2925 (Table 1). This helped later to determine the orientation relative to the xylE gene in the phage vector.

TABLE 1

The orientation of mmy fragments inserted into pIJ2925

| Fragment | Derivative of pIJ2925 | Enzyme used to determine orientation | Orientation* |
|---|---|---|---|
| reg | pIJ560 | XhoI | r |
| C2.18 | pIJ561 | EcoRI | r |
| mmr | pIJ562 | PvuII | l |
| A4.2 | pIJ563 | SstI | l |
| A3.13 | pIJ564 | EcoRI | r |

*"r" indicates that the right end of the insert DNA is located at the right end of the pIJ2925 polylinker; "l" indicates that the left end of the insert DNA is located at the right end of the pIJ2925 polylinker.

The plasmids pIJ560-pIJ564 were cut with BglII and the purified digested DNA was ligated to KC861 DNA cut with BamHI. Protoplasts of S. lividans 1326 were transfected with the ligated DNA. 100-200 well separated plaques were picked to masterplates of 50 plaques each.

Figure 10:
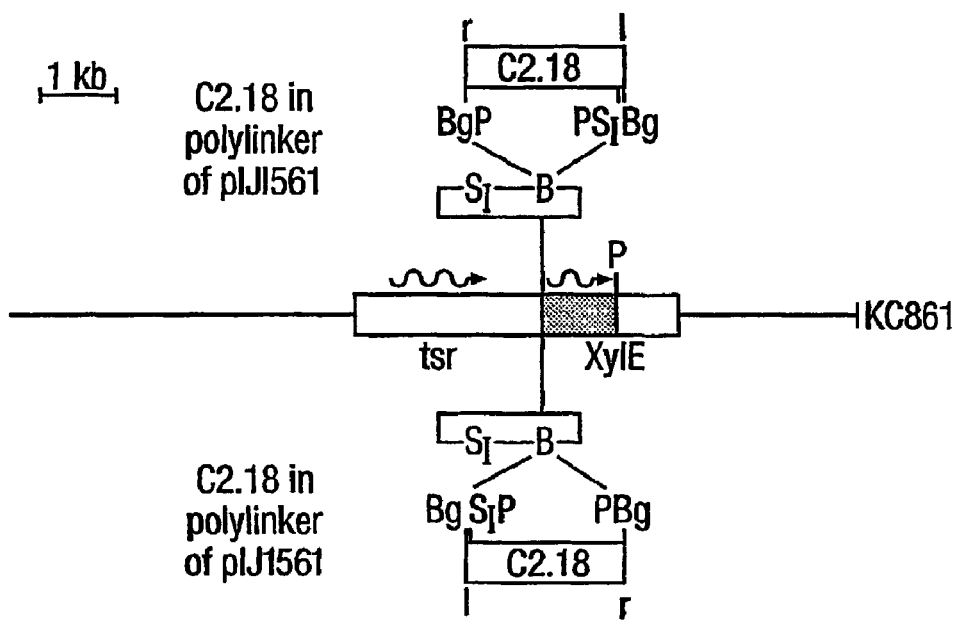

Phages with the desired insertion of mmy-DNA fragments were identified by a hybridisation signal on plaque lifts. The phage DNA was transferred from the plaques on the masterplate onto nitrocellulose (Benton & Davis, 1977). From the plasmids pIJ560-pIJ564 the inserted DNA fragments were isolated and labelled non-radioactively by the digoxigenin system of Boehringer Mannheim to prepare probe DNA for the hybridisation. Four positive plaques on the masterplate for each of the five insertions were purified to get phage suspensions from single plaques. Phage DNA was prepared and analysed by digestion with restriction enzymes to verify that it contained the expected insertion and to determine its orientation. As an example the situation is demonstrated for the insertion of C2.18 in FIG. 10. In this example restriction digests (not shown) of each sample with respectively PstI and SstI were used to determine the orientation of the insert in the sample. Table 2 shows the results of the DNA analysis and gives the names of the constructed phages.

TABLE 2

Structure of KC861 recombinants with mmy-DNA fused to xylE.

| Inserted fragment | Phage designation | Orientation of inserted fragment | Number of representatives in four analysed phages |
|---|---|---|---|
| reg (2.2 kb) | KC133 | r | 3 (A, B, C) |
|  | KC134 | l | 1 |
| C2.18 (2.05 kb) | KC135 | r | 2 (A, B) |
|  | KC136 | l | 2 (A, B) |
| mmr (2.5 kb) | KC137 | r | 3 (A, B, C) |
|  | KC138 | l | 1 |
| A4.2 (2.75 kb) | KC139 | r | 1 |
|  | KC140 | l | 3 (A, B, C) |
| A3.13 (2.28 kb) | KC141 | r | 3 (A, B, C) |
|  | KC142 | l | 1 |

A, B and C name the different isolated phages;
r indicates that the right end of the insert DNA is to the right of KC861; and
l indicates that the left end of the insert DNA is to the right of KC861.

The orientation was determined using SstI, for which there is a unique site in the polylinker regions of KC861 and pIJ2925. Information about the orientation of the cloned fragment in pIJ2925 was necessary (see Table 1).

Phage suspensions from selected single plaques were used to lysogenise the strains J1506 (SCPI$^+$) and J1507 (SCPI$^{NF}$). The integration of the phage conferred thiostrepton resistance on the lysogens and placed the xylE fusions into the mmy gene cluster of the host strain (FIG. 4a; FIG. 6a). To prepare suitable lysogens, 10-20 l of a phage suspension from a single plaque of each of KC133-KC142 was spotted on an R5 plate spread with $10^7$-$10^8$ spores of J1507 or J1506. After 5-7 days the cultures had sporulated and were replicated to minimal medium containing 50 gml$^{-1}$ thiostrepton. After c. four days resistant colonies were streaked on R5 plates containing 5 gml$^{-1}$ thiostrepton to get single colonies, which were then spread on the same medium to obtain spores of purified lysogens.

To check that the prophages had integrated at the expected locations, Southern blotting was done. Genomic DNA was prepared from 25 ml YEME cultures of the lysogens containing 4 gml$^{-1}$ thiostrepton. In each case an XhoI digestion of the DNA was used to investigate disruption in the mmy gene cluster. There is a unique XhoI site in KC861 upstream of the tsr gene. As the XhoI sites flanking or within the cloned fragments were located asymmetrically to their ends, it was possible deduce the orientation of the integrated phage and to confirm the results of the phage analysis. The same non-radioactive DNA probes as for the plaque lifts were used. Table 3 lists the results of the Southern analysis.

TABLE 3

Southern analysis of lysogens of J1507 and J1506.

| Cloned fragment | Distinctive band for wt | Integrated phage | Distinctive band for disruption | Obtained with J1507 | Obtained with J1506 |
|---|---|---|---|---|---|
| reg | 3.2 kb, 5.2 kb | KC133 | 2.35 kb | yes | — |
|  |  | KC134 | 3.7 kb | yes | — |
| C2.18 | 5.25 kb | KC135 | 4.55 kb | yes | yes |
|  |  | KC136 | 6.7 kb | yes | yes |
| mmr | 6.1 kb | KC137 | 7.75 kb | — | yes |
|  |  | KC138 | 4.75 kb | yes | yes |
| A4.2 | 6.1 kb | KC139 | 5.25 kb | — | yes |
|  |  | KC140 | 7.55 kb | yes | yes |
| A3.13 | 2.7 kb | KC141 | 4.4 kb | yes | yes |
|  |  | KC142 | 4.5 kb | — | yes |

Lysogens with the expected hybridisation pattern were obtained with every type of phage, though some of the strains tested did not show the expected pattern. Thus, J1507::KC137(A),137(B),139,142(A),142(B) were thiostrepton resistant, but the integration was not in the right place. As lysogens with the correct construction were obtained for these phages with J1506, no more J1507 lysogens were analysed.

The BamHI restriction site of KC861 into which the mmy DNA was inserted is part of a multiple cloning site (MCS) located close to, and just upstream of, the promoterless xylE gene. As illustrated by Guthrie and Chater (1990) and Bruton et al. (1991), this has the effect, upon integration of the phage by homologous recombination, of placing xylE under the control of the transcription unit from which the particular insert originated, provided that the transcription unit and xylE have the same orientation. Therefore, the level of expression of the relevant transcription unit is indicated by the level of xylE expression. Expression of xylE is readily monitored because the xylE gene product is an enzyme (catechol 2,3 dioxygenase) that converts colourless catechol into a yellow compound, 2-hydroxymuconic semialdehyde. This can be detected by eye as a yellow zone round colonies after spraying with catechol (the Ylo$^+$ phenotype), or quantitatively by spectrophotometry after cell-free extracts have been prepared (Zukowski et al., 1983; Ingram et al., 1989).

The in vivo assay for xylE activity of the lysogens (i.e. Ylo$^+$ phenotype) was carried out by spraying catechol onto colonies (Ingram et al., 1989; Bruton et al., 1991). Complete medium (CM; Hopwood et al., 1985), which gave strongest expression, was used throughout the experiments and HMM (Hobbs et al., 1992; solidified with 1% agar), in which the Ylo phenotype was more easily scored but which gave lower expression, was used only occasionally for comparison. Table 4 shows the combined results of repeated xylE tests for all fusion points. Cultures had been sprayed with catechol solution at ages of 42 h and 72 h.

TABLE 4

Plate assays for xylE activity in J1507 and J1506 lysogens (see following page).

| Cloned fragment | Lysogen | Ylo phenotype | Conclusion about transcription (see FIG. 9) |
|---|---|---|---|
| reg | J1507::KC133 | -- | not rightward across BglII at pos. 13.0 |
|  | J1507::KC134 | +++ | leftward across SstI at pos. 10.8 |
| C2.18 | J1507::KC135 | +++ | rightward across PstI at pos. 16.0 |
|  | J1506::KC134 | +++ | rightward across PstI at pos. 16.0 |
|  | J1507::KC136 | -- | not leftward across PstI at pos. 13.9 |
|  | J1506::KC136 | -- | not leftward across PstI at pos. 13.9 |
| mmr | J1506::KC137 | -- | not rightward across PstI at pos. 19.3 |
|  | J1507::KC138 | + | leftward across PstI at pos. 16.8 |
|  | J1506::KC138 | + | leftward across PstI at pos. 16.8 |
| A4.2 | J1506::KC139 | -- | not rightward across PstI at pos. 22.1 |
|  | J1507::KC140 | ++ | leftward across PstI at pos. 19.3 |
|  | J1506::KC140 | -- | leftward across PstI at pos. 19.3 |
| A3.13 | J1507::KC141 | -- | not rightward across PstI at pos. 25.0 |
|  | J1506::KC141 | -- | not rightward across PstI at pos. 25.0 |
|  | J1506::KC142 | +++ | leftward across PstI at pos. 22.7 |

Of particular relevance was the finding that the insert in KC135 gave rise to a strong Ylo$^{+++}$ phenotype in strain J1507::KC135. This was examined in closer detail by inoculating ca. $10^8$ J1507::KC135 spores onto each of a series of plates containing CM (Hopwood et al., 1985) supplemented with histidine (50 g ml$^{-1}$) and uracil (7.5 g ml$^{-1}$) overlaid with a cellophane disc as described by Tan and Chater (1993), then incubating at 30° C. for the times indicated in FIG. 4a, upper panel, before scraping off the mycelial growth. For catechol 2,3 dioxygenase assays, the mycelium from one cellophane disk was suspended in 0.5 ml extraction buffer, and cell-free extracts were prepared by sonication and clarified by centrifugation as in Ingram et al. (1989). Catechol 2.3 dioxygenase specific activities were determined by spectrophotometry, as above. The results are shown in FIG. 4a, upper panel. The specific activities in samples harvested before 30 h were not significantly above the lowest reliably measurable levels, but between 30 and 40 h, as the growth on the cellophane became dense and morphological differentiation began, there was a very rapid increase in activity up to 30 mU mg$^{-1}$ protein.

In an earlier experiment in which xylE was fused to the redX gene, which is involved in the synthesis of another antibiotic in *S. coelicolor*, Guthrie and Chater (1990) reported peak values of 2 mU mg$^{-1}$ protein. The mmy-driven transcription of xylE in J1507::KC135 was therefore very strong.

Figure 9:
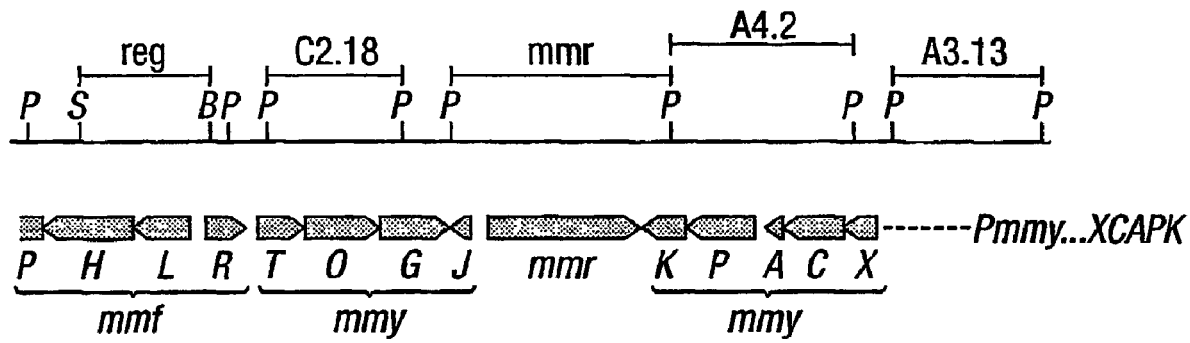

Further experiments (FIG. 4b) showed a similar pattern and level of xylE expression when suitable fusions were made at other points in the mmy cluster. The positions of these fusions are shown in FIG. 9. These results show that a foreign gene (in this example, xylE) can be expressed to quite high levels specifically late in growth when inserted at the illustrated locations in the mmy cluster, without the addition of any inducing agent.

EXAMPLE 2

A Diffusible Substance, Capable of Eliciting Methylenomycin Production from Certain Methylenomycin Non-producing Mutants, is Produced by a Mutant Containing the Leftmost 6.5 kb of the Methylenomycin Biosynthetic Gene Cluster, but Little if Any Other mmy DNA (a) In previous work (Kirby et al., 1975; Kirby and Hopwood, 1977) it was shown that mutants unable to make methylenomycin could be isolated after different procedures. The ability of these mutants to produce and/or respond to extracellular substances relevant to methylenomycin production was tested by growing strains close together on the surface of CM agar (Kirby and Hopwood, 1977). R333 was one of ten mutants that produced an extracellular substance that elicited methylenomycin production by another methylenomycin non-producing mutant, R39. In the work of Kirby and Hopwood (1977), it was considered likely that the substance produced by R333 was converted into methylenomycin.

Figure 5:
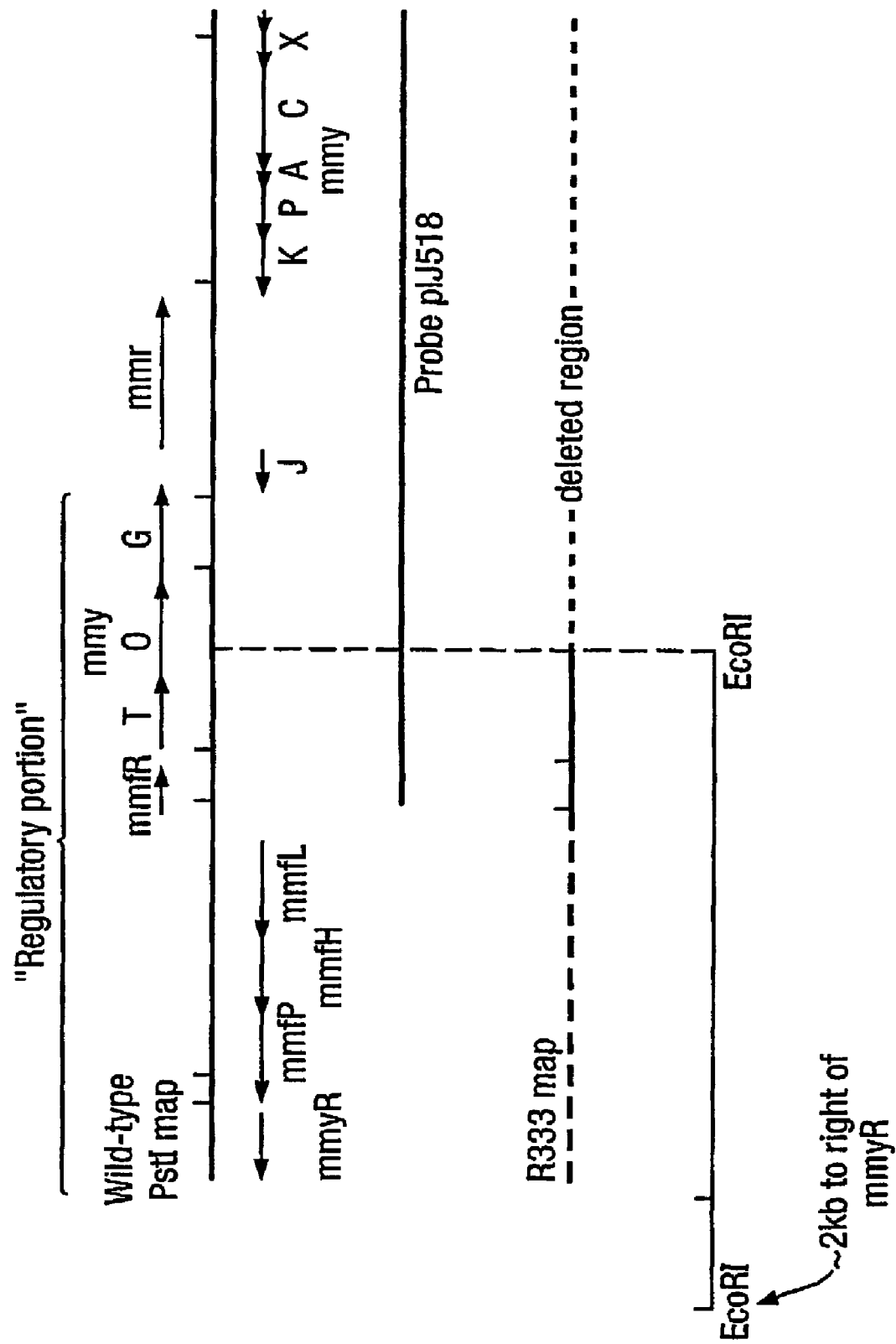

In the present example, DNA was isolated from R333 and digested with the restriction enzymes PstI and PvuII. The digested DNA was subjected to agarose gel electropheresis and blotted onto a nitrocellulose membrane (Southern, 1975). The membrane was then hybridised with a $^{32}$P-labelled probe derived by nick translation of pIJ518, a plasmid containing much of the mmy cluster (Chater and Bruton, 1985; FIG. 5). R333 contained a deletion extending rightwards from a position about 6.5 kb inside the left end of the mmy cluster, and ending beyond the righthand end of the KC518 insert. Thus, R333 contains about 6.5 kb of DNA from the left end of the mmy region, and little (perhaps no) other methylenomycin-related DNA (FIG. 5).

Having discovered the magnitude of the deletion of biosynthetic genes in R333, the present inventors suggest that this 6.5 kb region confers biosynthesis of an extracellular signalling molecule and that this, not an intermediate of methylenomycin biosynthesis, is the substance which is secreted by R333 and which is capable of stimulating R39 to produce methylenomycin.

This is consistent with the observation that only one of 16 mmy mutants studied by Kirby and Hopwood (1977) could be induced to produce methylenomycin when grown near other mmy mutants.

The present inventors further suggest that biosynthetic intermediates accumulating in blocked mutants are generally not freely released and exchangeable between strains, but observe that an immediate precursor (desepoxymethylenomycin) is produced by the wild-type and is convertible by SCP1$^+$ strains into methylenomycin (Hornemann and Hopwood, 1978). They further suggest that nearly the whole of the biosynthetic pathway has to be completed before a precursor capable of functioning in cosynthesis is produced—a requirement that would probably necessitate much more than ca. 6.5 kb of biosynthetic genes.

These suggestions, and other results indicating a regulatory role for some of this DNA (see above), are consistent with the deduced function of genes discovered by sequencing this region of the mmy cluster. The results of this sequence analysis are given in Example 3.

(b) In further confirmation of these predictions, an 8.3 kb EcoRI fragment of SCP1 containing the genes from mmyR to mmyT, with part of mmyO (FIG. 5), was sub-cloned from cosmid 73 of Redinbach et al (1998) into pSET152 (Bierman et al. 1992) and the resulting plasmid was introduced into the φC31 attB site of the SCP1⁻ *Streptomyces coelicclor* strain J1501 (Kieser et al 2000). The resulting strain, when used in "co-synthesis" tests with R39 (Kirby and Hopwood 1977), elicited methylenomycin production in the R39 strain (as judged by inhibition of the SCP⁻ indicator strain J1501).

EXAMPLE 3

DNA Sequence of the Left End of the Methylenomycin Biosynthetic Gene Cluster

The DNA sequence of the region from the left end of the mmy region to the previously sequenced (Neal and Chater, 1987) 2.55 kb PstI fragment containing mmr (see FIG. 5) was determined in three sections. The leftmost XhoI fragment (ca. 3.2 kb) was sequenced by dideoxy-sequencing using the method of Sanger et al. (1977), adapted as described in Bruton and Chater (1987). Random sonicated fragments were cloned into M13mp19 to provide the templates for sequencing, using M13 forward primer (Norrander et al., 1983). The overlapping SstI/PstI (ca. 5 kb) and PvuII (ca. 2.2 kb) fragments were sequenced by automated fluorescence sequencing on an ABI automated sequencer, using templates cloned into pbluescript vectors. For one orientation, templates were generated by the exonuclease III procedure of Henikoff (1984), and in the other, oligonucleotides were designed for "primer walking". All sequences were determined on both strands, and each base position was read through in at least two sequencing reactions. The sequence is given in FIG. 7.

Use of the FRAME programme (Bibb et al., 1984) led to the recognition that there are nine methylenomycin-related genes to the left of the resistance gene mmr (FIGS. 1 and 5). Only one of these, mmyJ, had previously been sequenced (Neal and Chater, 1987).

Predicted Functions of Genes Identified by Sequencing

Using the BLAST (Altschul et al., 1990; 1996) and TFASTA (Pearson and Lipmann, 1988) programs to search the major protein and DNA databases, similarities of the deduced products of the eight newly sequenced genes to proteins of known function were discovered. Three of the eight—mmfL, mmfR and mmyR—were of particular interest, because they gave crucial clues about the nature of the regulation of the mmy genes and the putative extracellular signalling molecule, relevant to the design and use of the expression system that is the subject of this patent application. In this section we give details of these similarities. The products of the other five genes all showed some degree of resemblance to various enzymes, and are likely to be directly involved in enzymatic reactions leading to the biosynthesis or metabolism of methylenomycin or the GBL factor involved in regulating methylenomycin biosynthesis.

mmfL

Figure 3:
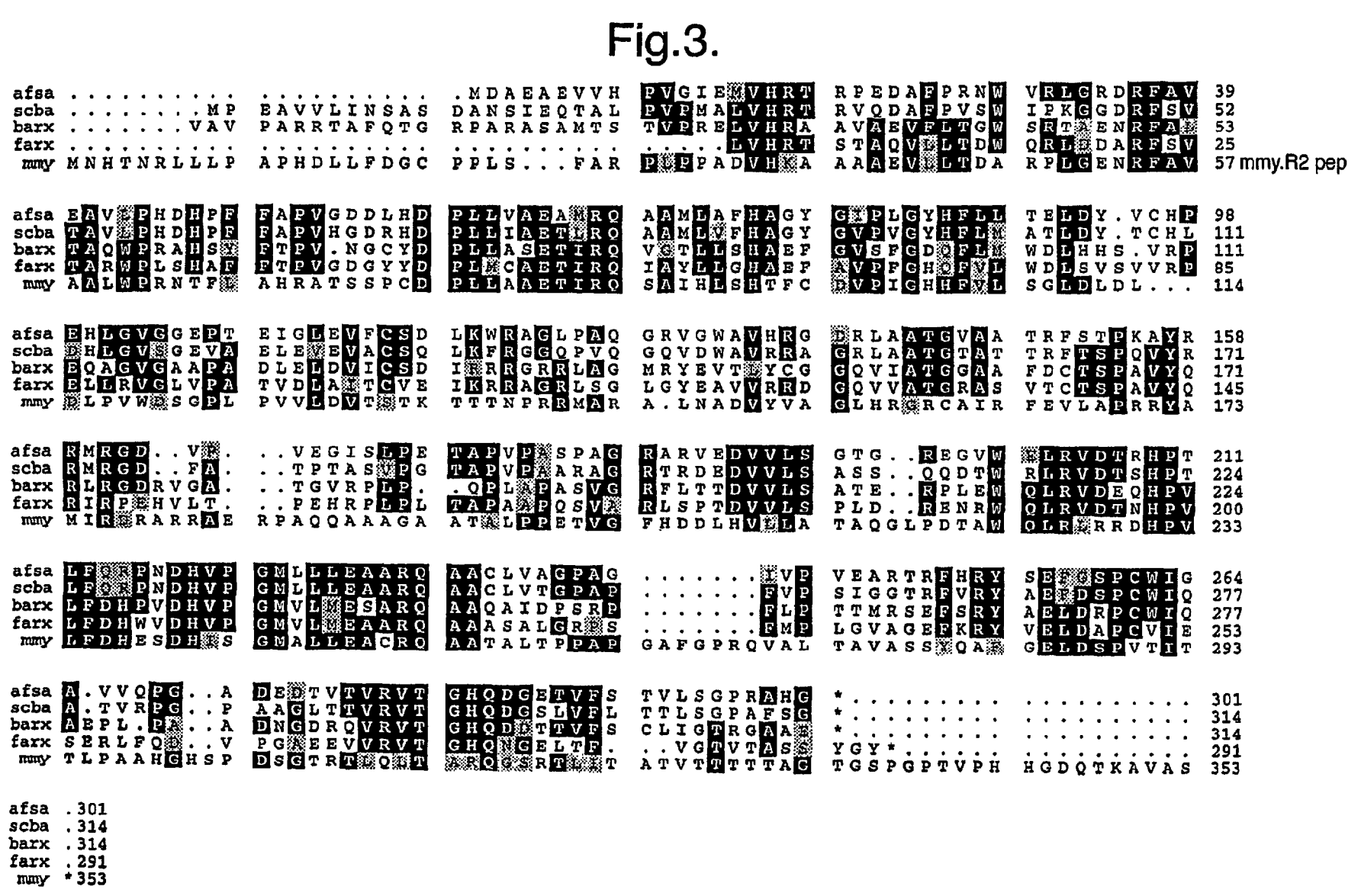

The predicted product of mmfL (MmfL) showed significant similarity to only four proteins: AfsA, ScbA, BarX and FarX. These proteins are all from other Streptomyces spp., and they are all intimately associated with the production of GBL signalling molecules involved in the regulation of antibiotic production (they are generally believed to be the enzymes responsible for GBL synthesis: Horinouchi et al., 1985, 1989; E. Takano, personal communication). The similarity of MmfL to these proteins is essentially end-to-end, and is very highly significant (FIG. 3). The discovery of such a gene in a small region of DNA that encodes production of an extracellular substance that stimulates methylenomycin production (See Example 2) makes it highly likely that the signal is a GBL, and that MmfL protein encodes a critical step in its biosynthesis.

mmfR and mmyR

The MmfR and MmyR proteins show significant alignment with a large family of bacterial regulatory proteins (the TetR "superfamily"), principally in a substantial region near the N-terminus of the proteins. This region has been shown in a few of these proteins (Hillen and Berens, 1994) to assume an α-helix-turn-α-helix organisation that permits it to bind to specific sequences in double-stranded DNA.

Figure 2:
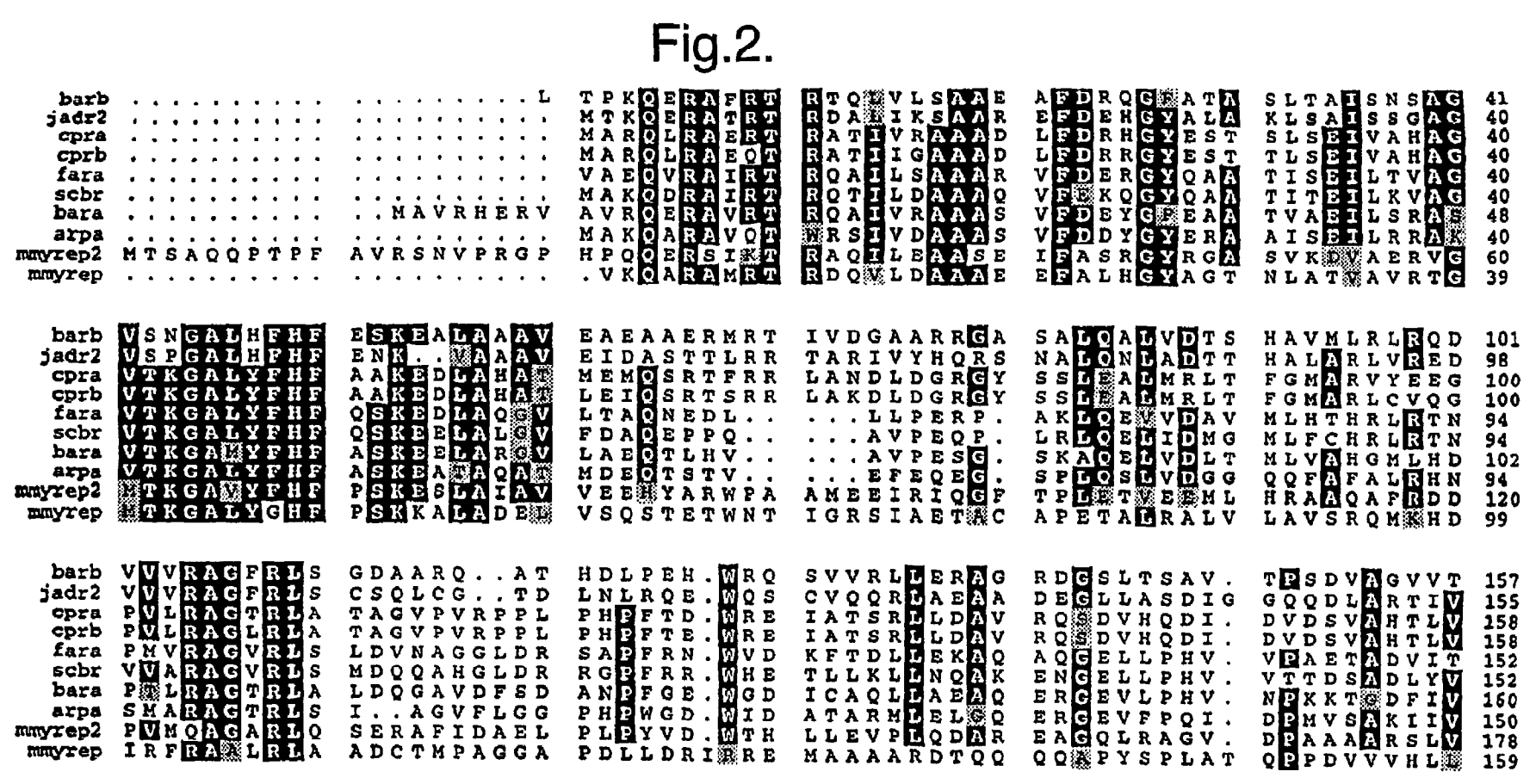
Figure 2:
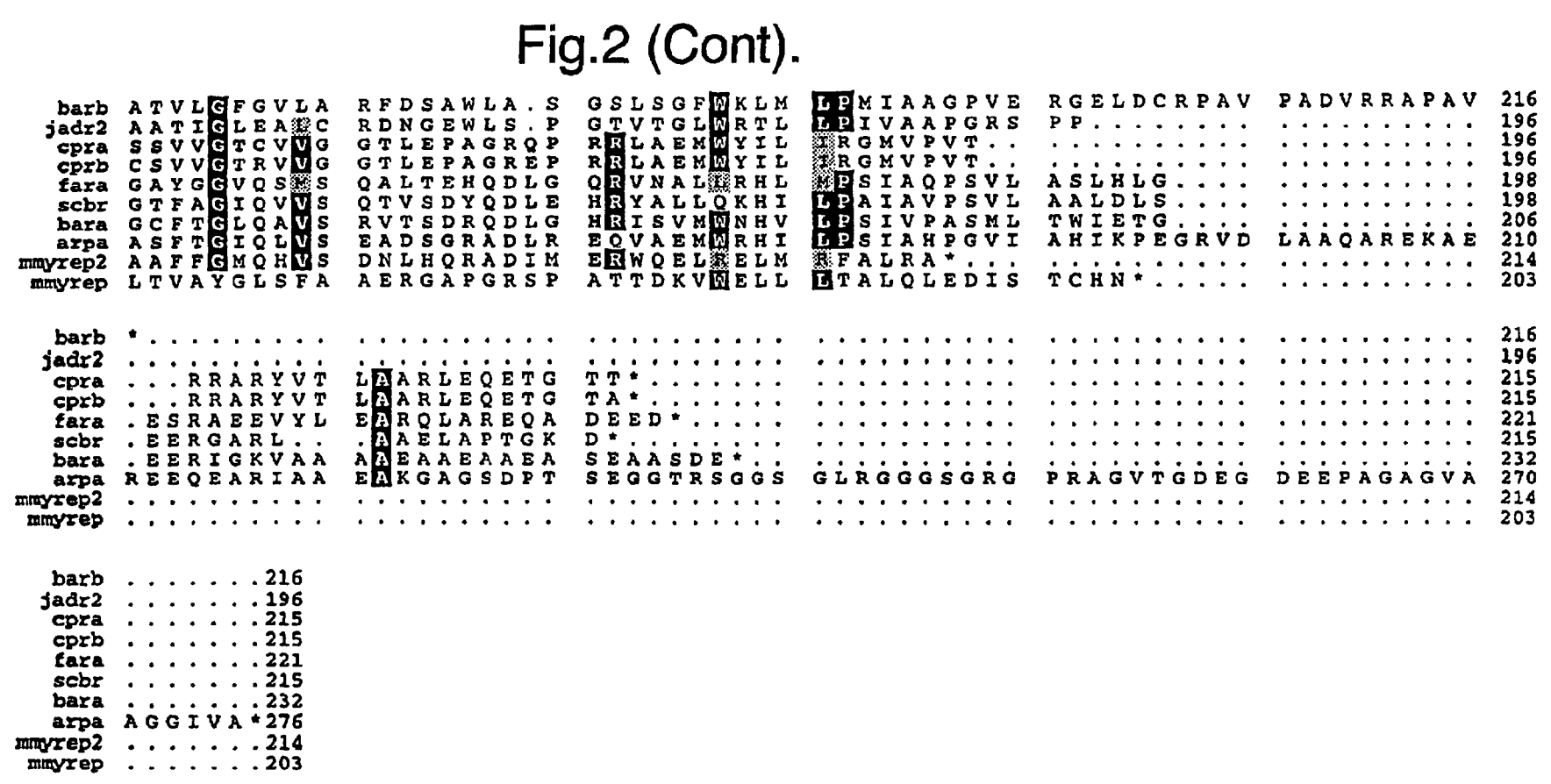

The most similar proteins to MmfR and MmyR form a particular sub-group (or "family"). All are from *Streptomyces* spp., and where sufficiently studied, all are associated with the regulation of antibiotic production and/or morphological differentiation (Onaka and Horinouchi, 1997; Onaka et al., 1997, 1998; Sugiyama et al., 1998; Nakano et al., 1998). The alignments are shown in FIG. 2.

The greatest similarity is in the region of the DNA-binding domain expected to make sequence-specific contacts with target DNA sequences, leading to the expectation that MmfR and MmyR bind sequences similar to those recognised by the other members of the family (see below). Although the central and C-terminal regions of these proteins are less well conserved, nevertheless there is evidence of similarity throughout these regions, whereas other members of the TetR superfamily do not show similarity to MmfR beyond the N-terminal region. The aligned proteins have a very significant further feature in common—the ones studied to-date all act as specific receptors for different GBL signalling molecules.

The present inventors have newly discovered that mmfR and the putative GBL biosynthesis gene mmfL are arranged in a similar way, and close inspection of the sequence between them reveals a palindromic sequence (half-site 5'-GGAAGGTATTA-3'; SEQ ID NO: 2) that resembles the consensus sequence (half-site 5'-GG(T/C)CGGT(A/T)(T/C)G(T/G)-3'; SEQ ID NO: 1) defined for binding of DNA by the ArpA protein that is the archetype of these factor-binding proteins (Onaka and Horinouchi, 1997).

The present inventors therefore suggest that the chemically undefined extracellular factor secreted by R333 (see Example 2) is a GBL whose extracellular concentration builds up slowly as hyphal density in the cell culture increases, to some critical threshold at which it is effectively perceived by the binding protein encoded by mmfR. This interaction releases MmfR from its location in the bidirectional promoter region, leading to derepression of mmfL and hence of factor biosynthesis. This in turn, it is -proposed, causes an acceleration in the rate of factor production, sufficient to interact with, and inactivate, repressor(s) bound either to the mmyTOG and mmy . . . XCAPK promoters or to the promoter of another regulatory gene (e.g. mmyB) needed to activate the mmyTOG and mmy . . . XCAPK promoters, permitting the mmyTOG and mmy . . . XCAPK genes to be expressed. A convenient hypothesis would be that the mmyR gene product (MmyR, see below) is this repressor and that MmyR requires a higher GBL concentration for its repressor function to be inactivated than does MmfR.

EXAPLE 4

Prevention of Translation of mmfL mRNA is Associated with Failure to Transcribe mmy DNA (a) In the DNA sequencing in Example 3 mmfL is the only gene to contain a TTA (leucine) codon. Such codons are unexpressed in severe bldA mutants, because bldA encodes the only tRNA capable of translating UUA codons (Leskiw et al., 1991). A prediction of the model for regulation of methylenomycin production is that mmfL mRNA would be untranslatable in a bldA mutant, leading to inability to make the GBL factor and hence to inability to transcribe the genes for methylenomycin production. To test this, xylE fusions into various parts of the mmy cluster of a bldA mutant were constructed using the C31KC861 derivatives described in Example 1. The ability of the resulting strains to express xylE was then tested by the qualitative plate method. Catechol oxygenase activity is not detected, confirming the prediction, and indicating that a TTA-containing gene is involved in regulating mmy gene expression.

(b) In verification of this, the TTA codon of mmfL was changed to CTC in the 0.9 kb SunI internal fragment of mmfL (which was sub-cloned into pFA6a (Wach et al. 1994, replacing the KanMX module), using the "Quick Change" system of Stratagene, followed by reinsertion of the SunI fragment into the 1.7 kb XhoI-BglII fragment containing mmfL (in pIJ2925, Kieser et al. 2000) to give mmfL$_{CTC}$. This fragment was sub-cloned into pSET151 (Bierman et al. 1992) and introduced into J1703 (bldA$^-$, SCP1$^{NF}$:Lawlor 1997). Most of the resulting strains acquired the ability to stimulate R39 to produce methylenomycin in co-synthesis, proving that non-translation of the TTA codon of mmfL is responsible for factor non-production in the bldA mutant. However, none of the strains produced methylenomycin, indicating that an additional bldA-dependent step intervenes between factor production and methylenomycin production. This was further verified, since J1703 was not stimulated to produce methylenomyin by growth adjacent to the GBL factor-producing strain R333. The likely intervening step is a gene (mmyB) located about 9 kb to the right of the sequence given in FIG. 7. This gene is predicted to encode a DNA-binding protein and contains a TTA codon.

EXAMPLE 5

Construction of a Vector (φG-UP) Permitting the Easy Insertion of Small Transcription Units Into the Expression Region of the Methylenomycin Gene Cluster In order to facilitate expression of foreign genes, the vector φG-UP is first constructed. Using the procedures in Hopwood et al. (1985) and Kieser et al. (2000), DNA is extracted from large-scale preparations of φC31 KC889 (FIG. 11). 5 µg of this DNA is digested by EcoRI and—separately—5 µg is digested by XboI plus SstI. Completeness of digestion is checked by agarose gel electrophoresis (1% agarose) of 0.5 kg of each digested DNA, immediately after heating it to 70° C. for 10 min and cooling it on ice (to separate cohesive ends of the phage DNA).

After phenol extraction, the two digests are mixed and co-precipitated with ethanol, washed once with 70% ethanol, then dissolved in 100 µl Klenow buffer. The solution is heated at 70° C. for 10 min in a waterbath, which is then turned off and allowed to cool down overnight (this permits φC31 cos ends to join together). The dissolved DNA is then subjected to filling in of the 5' ends generated by XhoI and EcoRI, using Klenow enzyme, before phenol extraction, ethanol precipitation, washing with 70° ethanol, and redissolving in 200 µl ligation buffer, prior to ligation overnight using conditions suitable for blunt end ligation (low ATP, high T4 DNA ligase). After ligation, the DNA is precipitated with ethanol, washed in 70% ethanol, and dissolved in 100 µl TE buffer, prior to being used for transfection of *Streptomyces lividans* 1326 essentially as described by Hopwood et al. (1985) and Kieser et al. (2000).

Most plaques are expected to have phages with the desired DNA structure (deletion of the XhoI-EcoRI fragment that contains vph), so screening is done by restriction analysis of DNA isolated from the progeny of 12 of the transfectant plaques. The use of PstI, BglII and/or BamHI provides diagnostic digestion patterns.

Figure 11:
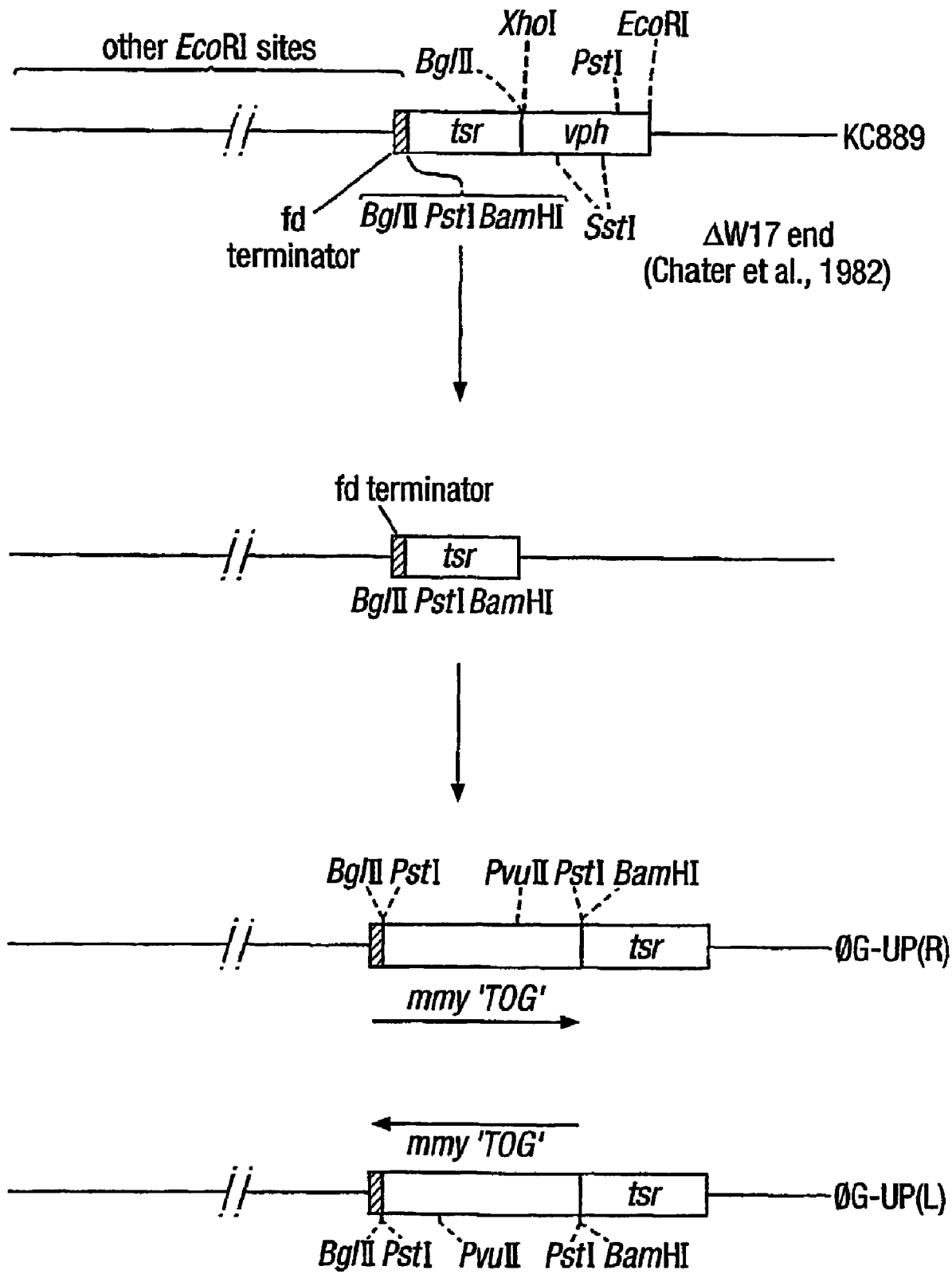
FIG. 11 shows the construction of ϕG-UP vectors.

A phage with the correct organisation is identified. A large-scale DNA preparation from this phage is digested with PstI, ethanol precipitated, washed with 70% ethanol and redissolved in TE buffer, before being ligated (at 100-200 µg ml$^{-1}$ DNA) with an equimolar amount of the 2.05 kb PstI fragment C2.18 (Bruton and Chater, 1983), obtained from pIJ518 by PstI digestion followed by separation by agarose gel electrophoresis and isolation from the gel. After ligation, the DNA is ethanol precipitated, washed and redissolved in 20 µl TE buffer. This solution is used to transfect *S. lividans*, and the resulting plaques are arrayed on master plates prior to analysis by filter hybridisation (Benton and Davis, 1978) to identify candidates with the desired insertion. The probe for this analysis is the C2.18 PstI fragment, labelled non-radioactively with the digoxigenin system. Twelve candidate plaques are used to propagate phage for small-scale DNA preparation. The DNA is analysed by restriction analysis, using two enzyme combinations: BamHI plus PvuII, and BglII plus PvuII. A phage with each orientation of the insert is retained. Of these, the phage in which the BglII plus PvuII digest gives a 1.2 kb fragment and the BamHI plus PvuII digest gives a 0.8 kb fragment, is termed φG-UP (R) and that in which the BamHI plus PvuII digest gives a 1.2 kb fragment and the BglII plus PvuII digest gives a 0.8 kb fragment is termed φG-UP (L) (FIG. 11).

EXAMPLE 6

Production of the SalI Restriction Enzyme by Placing the salIR Gene Under the Control of the Expression Cassette in a φG-UP Vector SalI is a restriction enzyme with substantial use for molecular biology, and therefore with substantial sales. The genes for SalI and the SalI methylase were cloned by Rodicio and Chater (1988) from the producing organism, *Streptomyces albus* G, and sequenced by Rodicio et al. (1994). They are arranged in tandem, and are expressed as a bicistronic operon (salIR preceding salIM) (Rodicio et al., 1994; Alvarez et al., 1993). In addition, salIM is expressed from its own promoter (Alvarez et al., 1993). Expression of these genes is usually at a very low level, a very high specific activity of SalI being generated by a small amount of protein (of the order of 10$^6$ units µg$^{-1}$ protein). Here we show how the expression cassette in φG-UP can be used to overproduce SalI.

Figure 12:
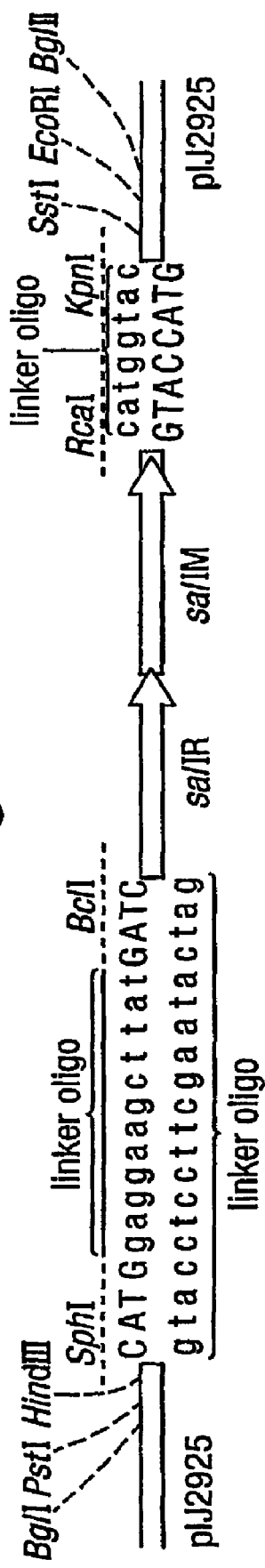
FIG. 12 shows the restriction sites and oligonucleotides (top: SEQ ID NO: 27; bottom: SEQ ID NO: 28) used to provide the sallR gene as a BglII fragment suitable for expression in a ϕG-UP vector.

The sa1IRM genes are present in pIJ4430 (Rodicio and Chater, 1988). To introduce the gene pair into φG-UP, pIJ4430 is first cleaved with BclI and then with RcaI to generate a fragment with protruding 5' GATC and 5' CATG single-stranded ends. This fragment is inserted into the intermediate vector pIJ2925 (Janssen and Bibb, 1993), using the oligonucleotide adaptors shown in FIG. 12. The fragment is then excised from the intermediate vector by digestion with BglII, and ligated with φG-UP (L) cleaved with BglII. The ligation mixture is used to transfect *S. lividans*, and the resulting plaques are screened by plaque hybridisation, using the digoxigenin-labelled salIRM BclI-RcaI fragment as a probe. Phages from twelve hybridizing plaques are used for small-scale DNA preparations, and the resulting DNA samples are analysed by digestion with BglII to demonstrate the presence of the full-length 2.9 kb insert, and PstI to determine the orientation of the insert. An additional 2.9 kb PstI fragment would indicate the incorrect orientation, and the absence of such a fragment would indicate the correct orientation.

Once identified, the desired phage is used to prepare a high titre stock, spots of which are placed on an R2YE plate spread with J1507 spores. After 4-6 days at 30° C., when sporulation has taken place, the plate is replicated to MM (supplemented as necessary for the growth of the auxotrophic J1507) containing thiostrepton (50 µg ml$^{-1}$), and colonies present after 4 days are purified by single colony isolation then used to prepare confluent plates for the harvesting of dense spore suspensions.

In order to obtain the desired SalI enzyme, initially on a demonstration scale, the spores are used to inoculate 50 ml CM in a baffled 500 ml flask and the culture is incubated with shaking at 30° C. until stationary phase. At this time, the expression cassette is auto-activated, and the SalI RM genes expressed. The cloned salIM gene will achieve two purposes: the use of its own promoter during early growth will have permitted modification of the host DNA, so rendering it immune to cleavage when SalI is eventually produced; and the expression of SalIM during the main expression period will ensure the optimal production of salIR. Further extraction and purification of SalI follows standard procedures for restriction enzymes.

EXAMPLE 7

Figure 6:
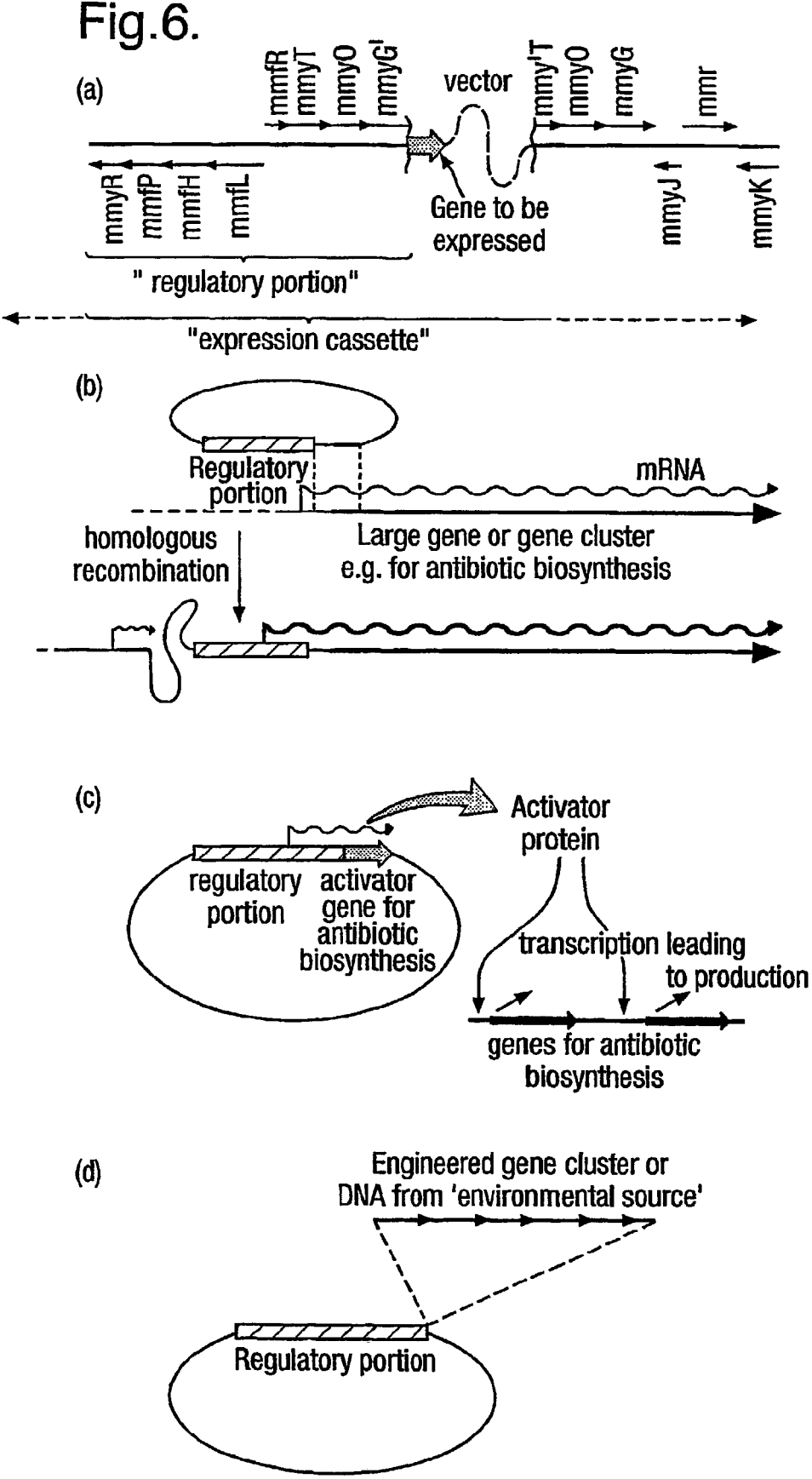

(a) Construction of pG-UP, an integrative plasmid vector for the activation of cryptic gene clusters As shown in FIG. 6(*b*), it is possible to cause the expression cassette to integrate into desired positions in a *Streptomyces* genome, and thereby to elicit stationary phase expression of adjacent genes. In Example 8, this is put to use in the expression of cryptic genes potentially encoding a new secondary metabolite. Here we describe the construction of pG-UP, an *E. coli* plasmid containing the expression cassette and capable of transfer into Streptomyces. Insertion of appropriate *Streptomyces* DNA into pG-UP will permit the use of the construct for gene expression of this kind. The vector is based on pSET151 (Bierman et al., 1992), though any *E. coli* replicon with a marker permitting selection in *Streptomyces* and lacking Streptomyces replication or chromosomal integration machinery could be used.

To construct pG-UP, the 6.2 kb BamHI and BstZ17I fragment of pIJ519 (Chater and Bruton, 1985; and FIG. 7) is isolated from an agarose gel and its ends are blunted by filling in with Klenow enzyme. It is ligated with pSET151 (precleaved with EcoRI and blunted by filling in with Klenow enzyme). After transformation of *E. coli* strain JM101 transformants are analysed by colony hybridisation using the BamHI and BstZ17I 6.2 kb fragment of pIJ519 as probe to detect the desired insert, and plasmid DNA is extracted from 12 positive colonies. The DNA is digested with BamHI plus BglII to determine the orientation of the insert. An example with a 2.3 kb fragment (rather than a 4 kb fragment) is chosen as pG-UP (FIG. 13*a*).

Figure 13A:
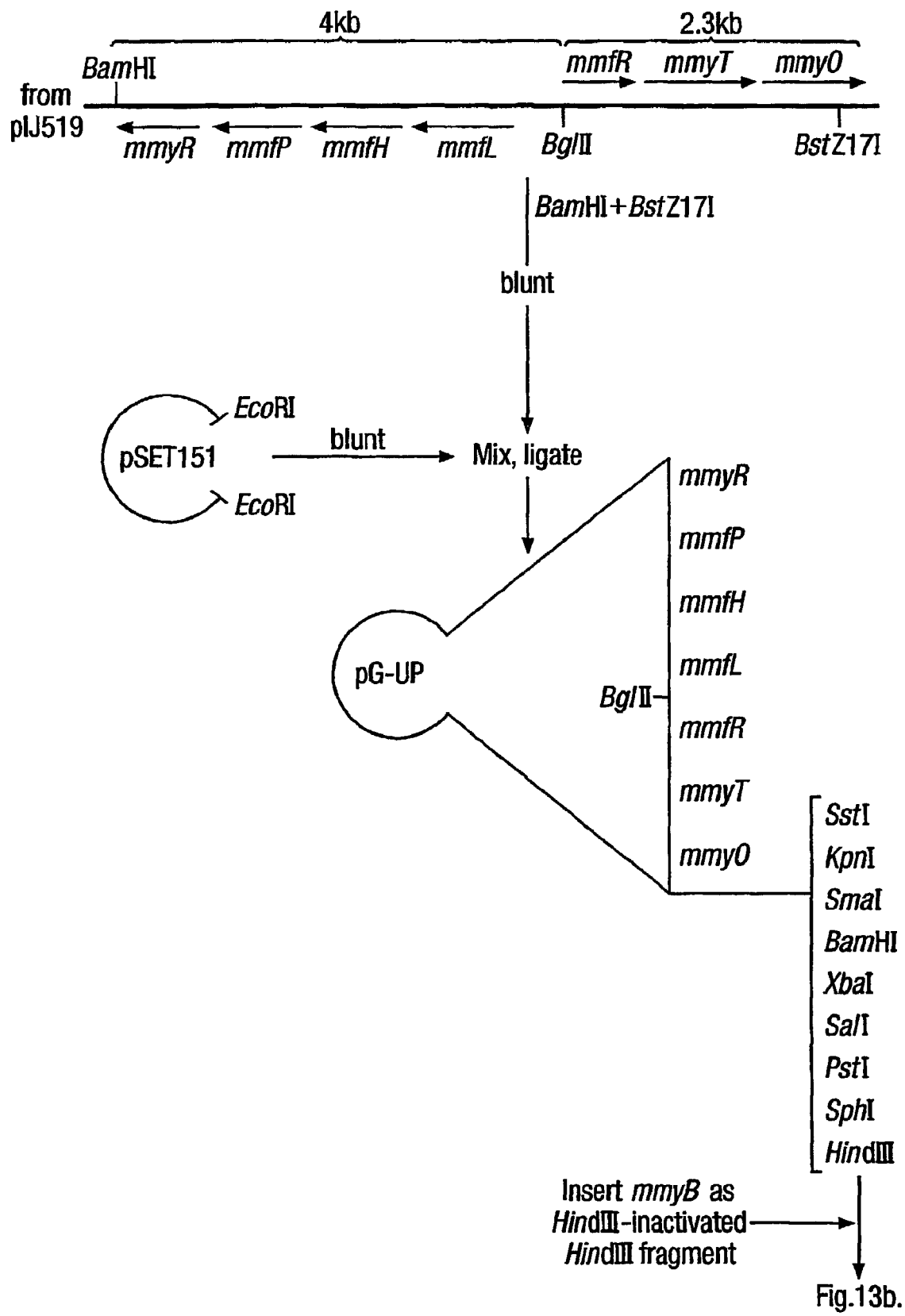

In the form shown in FIG. 13*a*, the effective use of pG-UP would be guaranteed I na host containing SCP1, to supply the additional genetic component (mmyB) revealed by experiments outlined in Example 4. The use of pG-UP in SCP1⁻ strains will benefit from the further incorporation of mmyB into pG-UP or into the host genome (see Example 7b).

(b) Incorporation of mmyB Into pG-UP to Give pG-UP*

In order to make the effective use of pG-UP independently of a separately provided mmyB gene, mmyB is obtained from the SCP1 plasmid by PCR amplification using the following primers, with cosmid 73 (Redinbach et al 1998) as template:

```
5' TATAAGCTTGGTGAACTCCTTCGGCGAGTGGTTCGGA 3'
(SEQ ID NO: 29)

5' TATGGTACCGGGGAGAACTCCTTGGGATACTTCCTG 3'
(SEQ ID NO: 30)
```

After amplification and conventional preparation for digestion, the PCR product is digested with KpnI, then purified before ligation with the unphosphorylated oligonucleotide 5' AGCTGTAC 3'. After gel purification, the linear DNA is cleaved with HindIII, repurified, and ligated with HindIII-cleaved pG-UP. After transformation of *E. coli* strain DH5 alpha, transformants are screened by colony hybridisation with a mmyB-specific probe, and plasmid is isolated from suitable colonies for verification by restriction analysis for constructs corresponding to FIG. 13*b*.

EXAMPLE 8

Use of the Expression Cassette in pG-UP in Forced Expression of Genes Apparently Encoding an Unknown Polyketide Molecule The project to sequence the genome of *Streptomyces coelicolor* A3(2) (www.sanger.ac.uk/Projects/S_coelicolor) has revealed several genes and gene clusters that encode proteins related to some known to be involved in the production of valuable antibiotics. One example is found in cosmid J21, which contains (inter alia) a series of six or seven genes (here termed "the J21 gene set") that appear to form a single transcription unit of perhaps 18 kb, among which two encode probably multidomain β-ketoacyl synthases of the type involved in the biosynthesis of erythromycin, rapamycin, tylosin, avermectin and other macrocyclic polyketides (Hopwood, 1997). No such compound is known to be made by *S. coelicolor* A3(2). In order to force expression of the J21 gene set, so that culture fluids can be screened for novel compounds, the J21 gene set is placed under the control of the new expression cassette. For this purpose, a PCR-amplified fragment of J21 DNA is cloned into the pG-UP vector as indicated in FIG. 14. In outline, the fragment is amplified from J21 DNA with the use of an oligonucleotide permitting the start codon of the first gene to be maximally accessible to ribosomes translating mmyG from the expression cassette, and a reverse primer oligonucleotide permitting amplification of a c. 1 kb fragment. Primers include features permitting ready subcloning into G-UP. After transformation of E. coli JM101 and arraying of colonies as patches on a masterplate, colony hybridisation is used to identify colonies containing the J21 insert (with, as probe, the amplified PCR fragment labelled non-radioactively). Plasmid DNA is prepared from candidate colonies by the standard alkaline lysis procedure, and checked by restriction analysis with the enzymes BamHI and HindIII. An example of such a plasmid, in which the orientation of the insert permits its "sense" transcription from the expression cassette, is introduced by transformation into the non-methylating E. coli strain ET12567 (MacNeil et al., 1992) containing the mobilising plasmid, UZ8002 (Flett et al., 1997); and transformants are used in conjugal mating with S. coelicolor M145, selecting thiostrepton-resistant, nalidixic acid-resistant exconjugants (Bierman et al., 1992). Most transformants are expected to contain pG-UP integrated, by homologous recombination, at the start of the J21 gene set. After culture of five representative transformants on R2YE (Hopwood et al., 1985) containing thiostrepton (5 µg/ml), spores are harvested and used to inoculate both liquid and surface CM cultures, which are then incubated for 3 days before extraction with ethyl acetate prior to conventional HPLC and mass spectrometry to determine the structures of any new compounds (e.g. McDaniel et al., 1993).

Figure 13B:
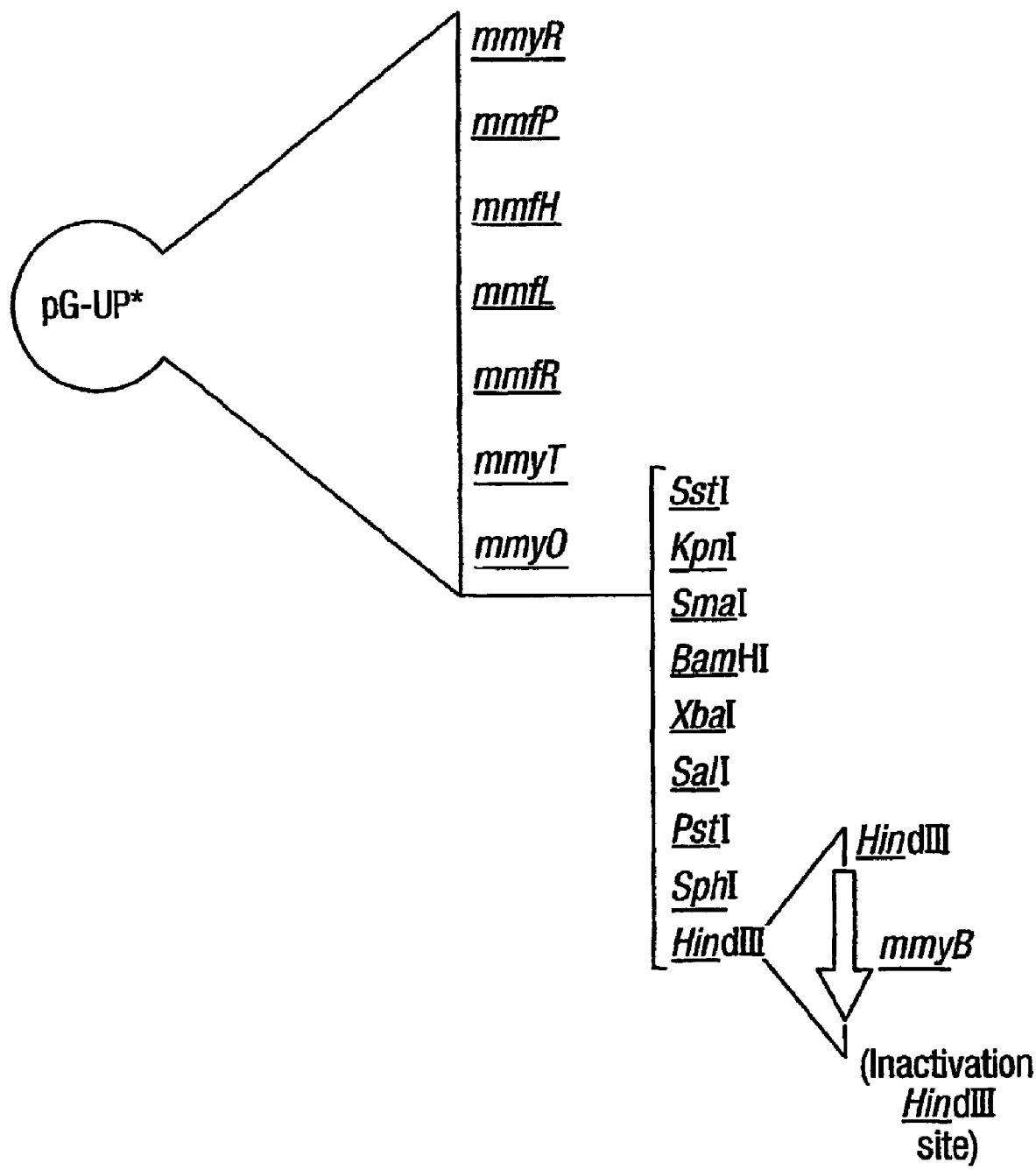

In an improved version of this strategy, mmyB is inserted into the polylinker HindIII site of pG-UP, preferably in a form regenerating a HindIII site only between the regulatory cassette and the mmyB gene (see Example 7b and FIG. 13b).

EXAMPLE 9

Fusing Genes to the Cassette in Vectors that can be Maintained in *Streptomyces* Hosts Many antibiotic pathways are highly dependent for expression on pathway-specific transcriptional activators. Additional copies of these genes often stimulate substantial overproduction of the cognate antibiotic (e.g. Chater, 1990). The use of the expression cassette to express such genes would permit over-expression to be confined to dense cultures, thereby minimising antibiotic production during earlier stages of growth: premature production would diminish overall yield and might be lethal if the antibiotic were a novel compound made by a genetically engineered hybrid pathway for which no self-resistance mechanism had evolved. The ability to express such hybrid gene sets in a standard host-vector system would permit the ready screening of large combinational libraries. Examples might include recombinant libraries of type I polyketide synthase genes. In another use of this kind of vector, DNA isolated directly from the environment (e.g. soil) can be expressed from the expression cassette, permitting screening for novel compounds (FIG. 6d). To facilitate this approach, the cassette, prepared as above, can be combined with different vectors capable of stable maintenance in *Streptomyces* hosts. Examples of such vectors include: those that are maintained as autonomous plasmids, at low copy or medium copy number (usually based on SCP2), or at high copy number (often based on pIJ101); and those that integrate efficiently into the chromosome by site-specific recombination involving the att sites of prophages (such as C31: see FIG. 6d for an example), integrative plasmids (such as pSAM2) or site-specific transposons (such as IS117).

EXAMPLE 10

Providing a Clean Background.

The bldA gene, which can be inactivated without interfering with growth, encodes the tRNA for the rare codon UUA (TTA in the DNA). TTA codons are present in most antibiotic gene clusters, but not in genes for growth. For this reason, bldA mutants make no antibiotics. The expression cassette contains a TTA codon, but a TTA codon-free version has been engineered to permit expression of mmfL in a bldA mutant (see Example 4).

To allow the effects of this to be full manifested, the TTA codon of mmyB is similarly engineered to an alternative leucine codon, using the Stratagene "Quick Change™" system, and the altered gene is introduced by standard procedures into the bldA host strain, along with the expression cassette coupled to the genes to be expressed. In one preferred case, the TTA-free mmyB gene is introduced into a pG-UP vector as indicated in FIG. 13b. However, it can be introduced separately from the expression cassette, e.g. as part of plasmid SCP1.

Because nearly all the TTA codons in antibiotic clusters are in regulatory genes, newly discovered sets of genes for biosynthetic enzymes are usually TTA-free. Therefore, expression of such genes from the TTA-free expression cassette will usually be effective in a bldA host. Any new metabolite will be made in the absence of other antibiotics, making it easier to study a range of biological and chemical aspects of the new metabolite without the need to separate it from other bioactive metabolites. Accordingly, the vectors described in examples 5, 7 and 9 would also be constructed with the TTA-free version of the cassette, to permit their use in bldA mutants hosts such as J1703, which contains an integrated copy of SCP1 [for the kind of vector described in example 5], or J1700, which does not contain any DNA from the methylenomycin cluster [for the kinds of vector described in examples 7 and 9].

EXAMPLE 11

Evaluation of the Methylenomycin Promoter.

SUMMARY

The methylenomycin cluster is borne on the large linear plasmid, SCP1, of *Streptomyces coelicolor*. Previous work has indicated that the promoters within this cluster are strong and could be used commercially.

This example describes a series of experiments to evaluate the strength of the methylenomycin promoter $P_{mmyTOG}$ in S. coelicolor and heterologous hosts such as S. lividans and S. erythraea.

In order to evaluate the promoter, a number of test vectors were engineered in which a reporter gene is placed under the control of the methylenomycin promoter. This fragment was then placed into a suitable vector for introduction into an appropriate host. The reporter gene used was the DEBS1-TE encoding gene. The strength of the promoter can be assessed on the basis of yield of triketide lactone. The actinorhodin promoter $P_{actI}$ was used as a positive control.

A gene cassette containing 5 genes, mmyR, mmfP, mmfH, mmfL and mmfR, and the promoter for mmyT, was constructed and is called the promoter cassette. In addition, a separate gene has been identified, mmyB, which contains a rare TTA codon, and is also thought to be involved in the regulation of this promoter. Only trace amounts of triketide lactone are observed when the promoter cassette is used alone in *S. coelicolor*. Yields increase by 40-100-fold when the plasmid SCP1 is present in the cells. SCP1 harbours the methylenomycin cluster, which contains mmyB. We therefore suggest that the observed increase is due to the presence of the mmyB gene product.

The experiments carried out in the evaluation of the methylenomycin promoter are described in detail below.

(a) Isolation of the Promoter Cassette

The final expression vector contains the promoter cassette as a SpeI/NdeI fragment with the NdeI site located such that the ATG start codon of the gene of interest is optimally spaced from the ribosomal binding site of the promoter. This was achieved by amplifying each end of the cassette by PCR using oligonucleotide primers designed to incorporate the sequence for the appropriate restriction enzyme, and cloning in the central region using existing sites (FIG. 1).

The promoter cassette was isolated from cos73 (Redenbach et al 1998) as follows (see FIG. 15):

The 8366 bp EcoRI fragment of cos73 was cloned into the unique EcoRI site of pUC18 to give plasmid pCJR332.

The same EcoRI fragment was used as a template for PCR amplification of the ends of the promoter cassette. Oligonucleotide primer CR343 was designed to introduce the SpeI site at 2401-2406 bp (numbering from the beginning of the EcoRI fragment), this is 200 bp after the end of mmyR. Oligonucleotide primer CR344 is fully complementary to the wild-type sequence and binds at a SanDI site (3429-3435 bp—numbering from the beginning of the EcoRI fragment).

```
ATTACTAGTTCGCCGAGCGGCTGCGCTCGCTCCGTC    CR343

CCGCCGACGCGGGACCCCGCTGTGCAT             CR344
```

The 1050 bp PCR product was phosphorylated by treatment with T4 polynucleotide kinase and cloned into pUC18 previously digested with SmaI and dephosphorylated. The orientation was determined by restriction enzyme digestion and inserts from a number of clones of the desired orientation were sequenced to check for errors incorporated during in vitro polymerisation. None of the clones were error-free, all errors are substitutions and are within the primer binding region and after the stop codon of mmyR. It was considered that these would not affect the promoter cassette, but as a precaution two of these were selected to carry forward with the experiments and designated pCJR331A and pCJR331B, the errors are described below:

pCJR331A contains a G at 2415 bp where the wild-type sequence has a C pCJR331B contains a G at 2418 bp where the wild-type sequence has a C and a G at 2425 bp where the wild-type sequence has a C The 4750 bp SanDI fragment (3431-8180 bp numbering from start of 8366 bp EcoRI fragment) from pCJR332 was cloned into the unique SanDI site in each of pCJR331A and pCJR331B to give plasmids pCJR334A and pCJR334B which were confirmed by restriction analysis.

A second PCR was used to introduce the NdeI site for cloning of genes under the P$_{mmyTOG}$. Oligonucleotide primer CR346 was designed to introduce the NdeI site at 7481-7486 bp (numbering from the beginning of the EcoRI fragment). Oligonucleotide primer CR345 is fully complementary to the wild-type sequence and binds at an XcmI site 6844-6855 bp (numbering) from the beginning of the EcoRI fragment).

```
AATCACTGGCCATCGCCGTGGTGGAGGAGCACT       CR345

TTTCATATGCGCCCGCGCTCCCAGTCTCTTCTGCCA    CR346
```

The 657 bp PCR product was phosphorylated by treatment with T4 polynucleotide kinase and cloned into pUC18 previously digested with SmaI and dephosphorylated. The orientation was determined by restriction enzyme digestion and inserts from a number of clones of the desired orientation were sequenced to check for errors incorporated during in vitro polymerisation. One correct clone was selected and designated pCJR328.

The plasmids pCJR334A and pCJR334B were digested with HindIII and XcmI and the 4491 bp inserts isolated. These were used to ligate into pCJR328 digested with HindIII and XcmI. Correct clones were identified using restriction analysis and designated pCJR335A and pCJR335B.

These two plasmids, pCJR335A and pCJR335B contain the promoter cassette as defined previously on a SpeI/NdeI fragment. In order to test the utility of this promoter cassette it was introduced into different backbone vectors, which could be used in a number of different hosts, see (b) and (c).

(b) Construction of Plasmids pCMS100 and pCMS101

The backbone for the first expression vector is pCJR30 (Rowe et al 1998), which has been used previously for the production of the DEBS1-TE triketide lactone, from the actinorhodin promoter P$_{actI}$, in *Streptomyces coelicolor*. The plasmid pCJR30 is therefore the positive control for these experiments and will also provide the backbone for the expression vectors with the methylenomycin promoter.

pCJR30 was digested with NdeI and SpeI and the promoter cassettes from pCJR335A and pCJR335B isolated as SpeI/NdeI fragments. The promoter cassettes were ligated to the backbones, correct clones identified by restriction analysis, and a single clone from each ligation designated pCMS100A and pCMS100B as appropriate.

pCMS100A and pCMS100B are final constructs for testing the strength of the methylenomycin promoter P$_{mmyTOG}$. These plasmids can be used to assess levels of DEBS1-TE triketide lactone production in actinomycete hosts which can maintain the SCP2* origin of replication.

The backbone for the second expression vector is pCJR65 (pCJR65 is pCJR24 (Rowe et al 1998) containing DEBS1-TE as an NdeI/XbaI fragment), which has been used previously for the production of the DEBS1-TE triketide lactone, from the actinorhodin promoter P$_{actI}$, in *Saccharopolyspora erythraea*. The plasmid pCJR65 contains no origin of replication for actinomycetes and relies on the presence of the DEBS1-TE encoding gene as homologous DNA to allow integration into the chromosome.

pCJR65 was digested with NdeI and SpeI and the promoter cassettes from pCJR335A and pCJR335B isolated as SpeI/NdeI fragments. The promoter cassettes were ligated to the backbones, correct clones identified by restriction analysis and a single clone from each ligation designated pCMS101A and pCMS101B as appropriate.

pCMS101A and pCMS101B are final constructs for testing the strength of the methylenomycin promoter P$_{mmyTOG}$. These plasmids are used to assess levels of DEBS1-TE triketide lactone production in *S. erythraea* JC2 (Rowe et al 1998), or the level of erythromycin production in *S. erythraea* wild-type.

(c) Construction of Plasmids pCMS104 and pCMS105

Incorporation of the mmyB gene into pCMS100 and pCMS101 was engineered as follows;
The mmyB gene was amplified from cos73 with primers CR349 and CR350, which have the following sequences;

```
TATAAGCTTGGTGAACTCCTTCGGCGAGTGGTTCGGA    CR349
(SEQ ID NO: 29)

TATAAGCTTGGGGAGAACTCCTTGGGATACTTCCTG     CR350
(SEQ ID NO: 35)
```

Each of the oligonucleotide primers has a HindIII site (AAGCTT) incorporated at the 5 prime ends.
In the published database sequence AJ276673, the mmyB gene is located on the complementary strand between 18032 bp and 18892 bp—the oligonucleotide primers bind in the following positions;
17854-17890 binding region of CR350
19095-19122 binding region of CR349
The total fragment then covers the region 17854-19122 bp with HindIII sites directly flanking this. The entire non-coding DNA from either end of the gene is included in this fragment. It is anticipated that upstream of this gene there will be a promoter and this strategy should ensure that any promoter sequences are incorporated and if any terminator sequences are present these should also be included within the fragment. The PCR fragment was cloned into pUC18 previously digested with SmaI and dephosphorylated, and insert containing clones identified by restriction analysis. The insert was sequenced to confirm that no errors had been incorporated during PCR amplification and the resulting plasmid was called pMMYBH.
The mmyB gene was then isolated on a HindIII fragment and cloned into HindIII digested, dephosphorylated pCMS100A, pCMS100B, pCMS101A and pCMS101B to give pCMS104A, pCMS104B, pCMS105A and pCMS105B.

(d) Production of the DEBS1-TE Triketide Lactone from the $P_{mmyTOG}$ Promoter in *Streptomyces coelicolor*

The following *S. coelicolor* strains were transformed with pCMS100A and pCMS100B
*S. coelicolor* J1501 (SCP1-, SCP2-)
*S. coelicolor* J1506 (SCP1+, SCP2-)
*S. coelicolor* J1508 (SCP1NF, SCP2-)
Transformants were selected by resistance to thiostrepton and the presence of the plasmid confirmed by re-isolating the plasmid and analysing by restriction digestion.
Production and analysis experiments were carried out as follows:
6 ml of YEME + additives (Glycine, MgCl$_2$, uracil and histidine, as recommended) + thiostrepton at a final concentration of 5 µg/litre was inoculated with cells from a plate and grown for 48 hours at 30° C. (in flasks with springs, 250 rpm, 2 inch throw). 300 µl was used as a 5% inoculum into 6 ml of each of YEME and modified Complete Media (as described in Kieser et al 2000 but without the yeast nucleic acid hydrolysate). Cultures were incubated for 88 hours at 30° C. 3 ml of each culture was acidified with formic acid to pH 3 and extracted twice with an equal volume of ethyl acetate, and the organic phase evaporated to dryness using a Büchi rotor evaporator. This crude material was resuspended in 100 µl methanol and 1 µl applied to a Gas Chromatography instrument with a Mass Spectrometry detector. Yields are calculated by comparison to a synthetic standard and the numbers given represent the quantity of triketide lactone in the 3 ml samples removed from the culture.

Results for production in complete medium:

| Plasmid | Colony isolate | *S. coelicolor* J1501 | *S. coelicolor* J1506 |
|---|---|---|---|
| pCMS100A | 2 | No product | |
|  | 3 | Trace amount | |
| pCMS100B | 4 | Trace amount | |
| pCMS100A | 6 | | 17 mg/litre |
|  | 7 | | 2.3 mg/litre |
| pCMS100B | 8 | | 0.5 mg/litre |

These results indicate that there is considerable colony to colony variability in production level, this is to be expected following protoplast transformation. In the absence of SCP1, very little product is observed, a trace amount indicates less than 0.1 mg/litre. We are confident that the trace amounts we see are the triketide lactone as the behaviour of the triketide lactone on GC-MS is predictable and the mass-spectroscopy fragmentation is characteristic. The production levels when cultures were grown in complete medium are comparable to when the same colonies are grown in YEME (full data not yet available). For example, *S. coelicolor* J1506 [pCMS100A] colonies 6 and 7 yielded 20 and 4 mg/litre respectively when cultured in YEME.

Further experiments were carried out as follows. Cultures were grown in 6 ml of an appropriate medium and this was used as a 5% inoculum for production cultures. In this way the production cultures for a single isolate should be comparable, and comparison of production levels between isolates should be relatively robust. In all cases yields are based on 3 or 4 ml of culture withdrawn from the flasks, this does not in any of the cases take into account evaporative loss of liquid during fermentation. This means that the yields quoted are yields in the final cultures rather than production levels. Yields are calculated using mass spectrometry, which has an associated error, but such errors should be similar for all samples, with the largest errors being in calculation of the lowest yields due to ill-defined small peaks.

It should also be noted that the results are always given for the propionate starter triketide lactone [1]. There is a second product from the DEBS1-TE system and this is the equivalent acetate starter triketide lactone [2] which is mainly seen in high producers, or when propionate is limiting in the system. In general, in these experiments this represents less than 5% of the overall product. However, from plates and from some of the complex media there is a significant percentage of is product and in these cases a yield has been calculated based on the propionate starter standard.

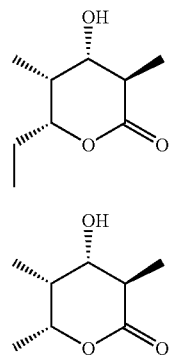

[1]

[2]

(e) Production of the DEBS1-TE Triketide Lactone from the P$_{mmyTOG}$ Promoter in *Streptomyces coelicolor* in Different Media

| | Culture | Yeme | Complete | Hobbs | SSDM |
|---|---|---|---|---|---|
| 1 | J1501 [pCJR30]_12 | No | trace (0.7) | 0.7 | no |
| 2 | J1501 [pCMS100A]_11 | 1 | trace | 1.1 | no |
| 3 | J1501 [pCMS100A]_12 | trace | trace | 1.4 | no |
| 4 | J1501 [pCMS100B]_7 | trace | trace | no | no |
| 5 | J1506 [pCJR30]_10 | No | trace (0.07) | trace | no |
| 6 | J1506 [pCMS100A]_3 | 20 | 17 | 0.02 | 0.5 |
| 7 | J1506 [pCMS100A]_9 | 4 | 2.3 | 0.03 | 0.6 |
| 8 | J1506 [pCMS100B]_7 | trace | 0.5 | trace | no |

Yeme = Yeme + appropriate additives: glycine, MgCl$_2$, uracil and histidine, as recommended.
Complete = As described in Kieser et al (2000) but without the yeast nucleic acid hydrolysate.
Hobbs = As described in Hobbs et al (1992)
SSDM = As described in Caffery et al (1992)

In all cases yield of triketide lactone are given as mg/litre on the basis of comparison to a known quantity of a synthetic by mass spectrometry. Quantitation by mass spectrometry is subject to a certain amount of error in that the concentration of a molecule in a mixture and the composition of the mixture will effect the ionisation of the subject compound. No indicates that no product was observed by mass spec, and trace indicates that a small peak is observed, but it is not well enough defined to accurately integrate.

The variability of production levels from one medium to another is significant; and it is proposed that maximal production levels may not have been attained. This can be achieved by statistical analysis production levels as different components of the media are used, and at different concentrations.

In Hobb's medium, which is adapted for methylenomycin production (i.e. 10 g/litre glucose is added instead of 2), there appears to be higher production in the absence of SCP1.

The increase in production with SCP1 present appears to be a real effect, despite the small sample size. It is suggested that by providing the mmyB gene in isolation the absolute yield may increase.

(f) Production of the DEBS1-TE Triketide Lactone from the P$_{mmyTOG}$ Promoter in *Saccharopolyspora erythraea* in Different Media

*Saccharopolyspora erythraea* NRRL2338 JC2 (Rowe et al 1998) was transformed with pCMS100A, pCMS100B, pCMS105A and pCMS105B. Transformants were selected using thiostrepton (final concentration 50 µg/litre) and a secondary round of selection, involving isolating spores and filtering onto fresh selection plates was performed to insure that the isolates contained the resistance from the plasmid.

Three isolates from each of *S. erythraea* JC2/pCMS100A and *S. erythraea* JC2/pCMS100B were used to inoculate 6 ml of TSB + tsr (final concentration 5 µg/litre). These precultures were used to inoculate 6 ml of each of two different production media which have previously been shown to yield good levels of erythromycin, SSDM is a defined minimal medium, and SM3 (Ranganathan et al 1999) is more complex. Production cultures were grown for 7 days and 4 ml of each taken and extracted. Analysis by GC-MS gave the following results.

| | SSDM | SM3 | |
|---|---|---|---|
| Culture | [1] | [1] | [2] |
| S. ery JC2 [pCMS100A]_1 | 0.5 | 8.4 | 3.0 |
| S. ery JC2 [pCMS100A]_2 | 0.3 | 8.2 | 0.2 |
| S. ery JC2 [pCMS100A]_3 | 0.6 | 4.0 | 0.2 |
| S. ery JC2 [pCMS100B]_1 | 0.8 | 7.3 | 0.2 |
| S. ery JC2 [pCMS100B]_2 | 0.9 | 5.5 | 0.2 |
| S. ery JC2 [pCMS100B]_3 | 0.5 | 5.0 | 0.2 |

[1] and [2] refer to the two triketide starter lactones, as described above.

This experiment demonstrates that the expression cassette can be used to drive expression of a nucleic acid of interest in host cells other than *S. coelicolor*. Some expression has also been demonstrated in *S. lividans*.

Again it is observed that the composition of the media has a significant effect on production level and it is expected that higher yields may be obtained upon optimisation and/or in the presence of mmyB.

(g) A Quick Look at Comparative Yields of Triketide Lactone from Patches on Plates To try to get a quick indication of whether or not the mmyB gene would affect production levels, plugs were taken from patches on R2YE plates and extracted to look for triketide lactone product.

Using strain J1501, which lacks the SCP1 plasmid (and hence a native mmyB gene), a dramatic (up to orders of magnitude) increase in yield was shown between pCMS100A (which lacks mmyB) and pCMS104 (the equivalent plasmid also possessing mmyB).

Using strain J1506 (which possesses native SCP1 and mmyB), more expression was shown with pCMS100A than was shown using this plasmid in J1501, but less expression was shown with pCMS104 in J1506 than in J1501. Expression in J1506 was similar with both plasmids.

This is consistent with the mmyB gene product being advantageous for expression, but also with such product being sequestered by (e.g. promoters of) the native SCP1 plasmid when present, rather than acting to increase expression from the expression cassette.

Yields represent the total product obtained from the whole agar plug (µg).

| R2YE | Culture | Yield (µg) | |
|---|---|---|---|
| | | [1] | [2] |
| 26 | J1501 [pCMS100A]_6 | trace | none |
| 27 | J1506 [pCMS100A]_8 | 1.0 | 0.4 |
| 31 | J1501 [pCMS104]_2 | 12 | 20 |
| 32 | J1501 [pCMS104]_6 | 1.5 | 2.5 |
| 33 | J1506 [pCMS104]_1 | 2.3 | 2.6 |
| 34 | J1506 [pCMS104]_7 | 1 | 1.0 |

In some cases the second product was the predominant product, probably reflecting substrate availability, which may therefore be a limiting factor.

REFERENCES

Aguilar, A. and D. A. Hopwood. 1982, Determination of methylenomycin A synthesis by the pSV1 plasmid from *Streptomyces violaceus-ruber* SANK95570. J. Gen. Microbiol. 128:1893-1901.

Altschul, S. F., W. Gish, W. Miller, E. W. Meyers and D. J. Lipman. 1990. Basic local alignment search tool. J. Mol. Biol. 215:403-410.

Altschul et al. 1996. Methods in Enzymology, 266:460-480.

Alvarez, M. A., K. F. Chater and M. R. Rodicio. 1993. Complex transcription of an operon encoding the SalI restriction-modification system of *Streptomyces albus* G. Mol. Microbiol. 8:243-252.

Ausubel, F. et al. 1992. Short Protocols in Molecular Biology, Second Edition. Eds, John Wiley & Sons.

Benton, W. D. and R. W. Davis. 1977. Screening lambda gt recombinant clones by hybridization to single plaques in situ. Science 196:180-182.

Bibb, M. J., P. R. Findlay and M. W. Johnson. 1984. The relationship between base composition and codon usage in bacterial genes and its use for the simple and reliable identification of protein-coding sequences. Gene 30:157-166.

Bibb, M. J., J. L. Schottel and S. N. Cohen. 1980. A DNA cloning system for interspecies gene transfer in antibiotic-producing *Streptomyces*. Nature 284:526-531.

Bierman, M., R. Logan, K. O'Brien, E. T. Seno, R. N. Rao and B. E. Schoner. 1992. Plasmid cloning vectors for the conjugal transfer of DNA from *Escherichia coli* to *Streptomyces* spp. Gene 116:43-49.

Bruton, C. J., E. P. Guthrie and K. F. Chater. 1991. Phage vectors that allow monitoring of secondary metabolism genes in *Streptomyces*. Bio/Technology 9:652-656.

Bruton, C. J. and K. F. Chater. 1987. Nucleotide sequence of IS110, an insertion sequence of *Streptomyces coelicolor* A3(2). Nucl. Acids Res. 15:7053-7065.

Caffery, P., Bevitt, D. J., Staunton, J., Leadlay, P, F. 1992. Identification of DEB1, DEBS2 and DEBS3, the multi-enzyme polypeptides of the erythromycin-producing polyketide synthase from *Saccharopolyspora erythraea*. FEBS Let. 304, 225-228.

Chater, K. F. C. J. Bruton, A. A. King and J. E. Saurez. 1982. The expression of *Streptomyces* and *Escherichia coli* drug resistance determinants cloned into the *Streptomyces* phage C31. Gene 19:21-23.

Chater, K. F. and C. J. Bruton. 1983. Mutational cloning in *Streptomyces* and the isolation of antibiotic production genes. Gene 26:67-78.

Chater, K. F. and C. J. Bruton. 1985. Resistance, regulatory and production genes for the antibiotic methylenomycin are clustered. EMBO J. 4:1893-1897.

Chater, K. F. 1990. The improving prospects for yield increase by genetic engineering in antibiotic-producing streptomycetes. Bio/Technology 8:115-121.

Fernandez-Moreno, M. A. 1991. The act cluster contains regulatory and antibiotic export genes, direct targets for control by the bldA tRNA gene of *Streptomyces*. Cell 66:769-780.

Fisher, S. H., C. J. Bruton and K. F. Chater. 1987. The glucose kinase gene of *Streptomyces coelicolor* and its use in selecting deletions from defined end-points. Mol. Gen. Genet. 206:35-44.

Flett, F., Mersinias, V. and C. P. Smith (1997) High efficiency intergeneric transfer of plasmid DNA from *Escherichia coli* to methyl DNA-restricting *Streptomyces*. FEMS Microbiol. Lett. 155:223-229.

Guthrie, E. P. and K. F. Chater. 1990. The level of a transcript required for production of a *Streptomyces coelicolor* antibiotic is conditionally dependent on a tRNA gene. J. Bacteriol. 172:6189-6193.

Henikoff, S. 1984. Unidirectional digestion with exonuclease III creates targeted breakpoints for DNA sequencing. Gene 28:351-359.

Hillen, W. and C. Berens. 1994. Mechanisms underlying expression of Tn10 encoded tetracycline resistance. Annu. Rev. Microbiol. 48:345-369.

Hobbs, G. A. I. C. Obanye, J. Petty, J. C. Mason, E. Barratt, D. C. J. Gardner, F. Flett, C. P. Smith, P. Broda and S. G. Oliver. 1992. An integrated approach to studying regulation of production of the antibiotic methylenomycin by *Streptomyces coelicolor* A3(2). J. Bacteriol. 174:1487-1494.

Hopwood, D. A. 1997. Genetic contributions to understanding polyketide synthases. Chem. Rev. 97:2465-2497.

Hopwood, D. A., M. J. Bibb, K. F. Chater, T. Kieser, C. J. Bruton, H. M. Kieser, D. J. Lydiate, C. P. Smith, J. M. Ward and H. Schrempf. 1985. Genetic manipulation of *Streptomyces*. A laboratory manual (Norwich: John Innes Foundation).

Horinouchi, S., H. Suzuki, M. Nishiyama and T. Beppu. 1989. Nucleotide sequence and transcriptional analysis of the *Streptomyces griseus* gene (afsA) responsible for A-factor biosynthesis. J. Bacteriol. 171:1206-1210.

Horinouchi, S., Y. Kumada and T. Beppu. 1984. Unstable genetic determinant of A-factor biosynthesis in streptomycin-producing organisms: cloning and characterization. J. Bacteriol. 158:481-487.

Hornemann, U. and D. A. Hopwood. 1978. Isolation and characterization of desepoxy-4-5-didehydro-methylenomycin A, a precursor of the antibiotic methylenomycin A in SCP1[+] strains of *Streptomyces coelicolor* A3(2). Tetrahed. Lett. 33:2977-2978.

Ingram, C., M. Brawner, P. Youngman and J. Westpheling. 1989. xylE functions as an efficient reporter gene in *Streptomyces* spp: use for the study of galP1, a catabolite-controlled promoter. J. Bacteriol. 171:6617-6624.

Janssen, G. R. and M. J. Bibb. 1993. Derivatives of pUC18 that have BglII sites flanking a modified multiple cloning site and that retain the ability to identify recombinant clones by visual screening of *Escherichia coli* colonies. Gene 124:133-134.

Kieser, T. et al. 2000. Practical *Streptomyces* genetics. John Innes Foundation. Norwich, UK.

Kirby, R. and D. A. Hopwood. 1977. Genetic determination of methylenomycin synthesis by the SCP1 plasmid of *Streptomyces coelicolor* A3 (2). J. Gen. Microbiol. 98:239-252.

Kirby, R., L. F. Wright and D. A. Hopwood. 1975. Plasmid-determined antibiotic synthesis and resistance in *Streptomyces coelicolor*. Nature 254:265-267.

Lawlor, E. J. 1987. Molecular genetics of BldA, a developmental gene of *Streptomyces coelicolor*. PhD thesis. University of East Anglia.

Leskiw, B. K., E. J. Lawlor, J. M. Fernandez-Abalos and K. F. Chater. 1991. TTA codons in some genes prevent their expression in a class of developmental, antibiotic-negative *Streptomyces* mutants. Proc. Natl. Acad. Sci., USA 88:2461-2465.

MacNeil, D. J. K. M. Gewain, C. L. Ruby, G. Dezeny, P. H. Gibbons and T. MacNeil. 1992. Analysis of *Streptomyces avermitilis* genes required for avermectin biosynthesis utilizing a novel integration vector. Gene 111:61-68.

McDaniel, R., S. Ebert-Khosla, D. A. Hopwood and C. Khosla. 1993. J. Am. Chem. Soc. 115:11671-11675.

Nakano, H., E. Takehara, T. Nihira and Y. Yamada. 1998. Gene replacement analysis of the *Streptomyces virginiae* barA gene encoding the butyrolactone autoregulator receptor reveals that BarA acts as a repressor in virginiamycin biosynthesis. J. Bacteriol. 180:3317-3322.

Neal, R. J. and K. F. Chater. 1987. Nucleotide sequence analysis reveals similarities between proteins determining methylenomycin A resistance in Streptomyces and tetracycline resistance in eubacteria. Gene 58:229-241.

Norrander, J., T. Kempe and J. Messing. 1983. Construction of improved M13 vector using oligonucleotide-directed mutagenesis. Gene 26:101-106.

Onaka, B. and S. Horinouchi. 1997. DNA-binding activity of the A-factor receptor protein and its recognition DNA sequences. Mol. Microbiol. 24:991-1000.

Onaka, H., M. Sugiyama and S. Horinouchi. 1997. A mutation at proline-115 in the a-factor receptor protein of *Streptomyces griseus* abolishes DNA-binding ability but not ligand-binding ability. J. Bacteriol. 179:2748-2752.

Onaka, H., T. Nakagawa and S. Horinouchi. 1998. Involvement of two A-factor receptor homologues in *Streptomyces coelicolor* A3(2) in the regulation of secondary metabolism and morphogenesis. Mol. Microbiol. 28:743-753.

Onaka, H., N. Ando, T. Nihira, Y. Yamada, T. Beppu and S. Horinouchi. 1995. Cloning and characterization of the A-factor receptor gene from *Streptomyces griseus*. J. Bacterial. 177:6083-6092.

Pearson, W. R. and D. J. Lipman. 1988. Improved tools for biological sequence comparison. Proc. Natl. Acad. Sci. USA 85:2444-2448.

Ranganathan, A., Timoney, M., Bycroft, M., Cortés, J., Thomas, I. P., Wilkinson, B., Kellenberger, L., Hanefeld, U., Galloway, I. S., Staunton, J. and Leadlay, P. F. 1999. Knowledge-based design of bimodular and trimodular polyketide synthases based on domain and module swaps: A route to simple statin analogues. Chem & Biol. 6, 731-741.

Redenbach, M., K. Ikeda, M. Yamasaki and H. Kinashi. 1998. Cloning and physical mapping of the EcoRI fragments of the giant linear plasmid SCP1. J. Bacteriol. 180:2796-2799.

Rodicio, M. R., T. Quinton-Jager, L. S. Moran, B. E. Slatko and G. G. Wilson. 1994. Organization and sequence of the SalI restriction-modification system. Gene 151:167-172.

Rowe, C. J., Cortés, J., Gaisser, S., Staunton, J., Leadlay, P. F. (1998) Construction of new vectors for high-level expression in actinomycetes. Gene, 216, 215-223.

Rodicio, M. R. and K. F. Chater. 1988. Cloning and expression of the SalI restriction-modification genes of *Streptomyces albus* G. Nol. Gen. Genet. 213:346-353.

Sanger, F., S. Nicklen and A. R. Coulson. 1977. DNA sequencing with chain-terminating. inhibitors. Proc. Natl. Acad. Sci. USA 74:5463-5467.

Southern, E. M. 1975. Detection of specific sequences among DNA fragments separated by gel electrophoresis. J. Mol. Biol. 98:503-517.

Sugiyama, M., H. Onaka, T. Nakagawa and S. Horinouchi. 1998. Site-directed mutagenesis of the A-factor receptor protein: Val-41 important for DNA-binding and Trp-119 important for ligand-binding. Gene 222:133-144.

Tan, H. and K. F. Chater. 1993. Two developmentally controlled promoters of *Streptomyces coelicolor* A3(2) that resemble the major class of motility-related promoters in other bacteria. J. Bacteriol. 175:933-940.

Wach, A. et al. 1984. New heterologous modules for classical or PCR based gene disruptions in *Saccharomyces cerevisiae*. Yeast 10:1793-1808.

White, J. and Bibb, M. 1997. BldA dependence of undecylprodigiosin production in *Streptomyces coelicolor* A3(2) involves a pathway-specific regulatory cascade. J. Bacteriiol. 179:627-633

Zukowski, M. M., D. F. Gaffney, D. Speck, M. Kauffmann, A. Findeli, A. Wisecup and J. P. Lecocq. 1983. Chromogenic identification of genetic regulatory signals in *Bacillus subtilis* based on expression of a cloned Pseudomonas gene. Proc. Natl. Acad. Sci USA 80:1101-1105.

The invention claimed is:

1. An expression cassette for the expression of a nucleic acid of interest, the expression cassette including:
   a. at least one regulatory portion including:
      i. a first regulatory element which includes a nucleic acid sequences mmyR encoding an MmyR polypeptide and/or a nucleic acid sequence mmfR encoding an MmfR polypeptide;
      ii. a second regulatory element which includes the nucleic acid sequence mmfL encoding an MmfL polypeptide; and
      iii. a repressible promoter, the function of which is repressed by the expression product of the first regulatory element, that repression being alleviated or removed by a product, the production of the last-mentioned product being conferred by the MmfL polypeptide; and
   b. a heterologous nucleic acid of interest, in operative association with said promoter; wherein:
      said MmyR polypeptide shows at least 90% amino acid sequence identity with the sequence of SEQ ID NO: 12, optionally excluding the first 6 listed amino acids;
      said MmfR polypeptide shows at least 90% amino acid sequence identity with the sequence of SEQ ID NO: 11 said MmyR polypeptide and/or said MmfR polypeptide being effective to repress the function of said repressible promoter; and
      said MmfL polypeptide shows at least 80% 90% amino acid sequence identity with the sequence of SEQ ID NO: 17 said MmfL polypeptide being effective to produce said product which alleviates or removes repression of said repressible promoter by said MmyR polypeptide and/or said MmfR polypeptide.

2. A set of nucleic acids for the expression of a nucleic acid of interest, the set of nucleic acids together including:
   a. at least one regulatory portion including:
      i. a first regulatory element which includes a nucleic acid sequence mmyR encoding an MmyR polypeptide, and/or a nucleic acid sequence mmfR encoding an MmfR polypeptide;
      ii. a second regulatory element which includes the nucleic acid sequence mmfL encoding an MmfL polypeptide;
      iii. a repressible promoter, the function of which is repressed by the expression product of the first regulatory element, that repression being alleviated or removed by a product, the production of the last-mentioned product being conferred by the MmfL polypeptide; and
   b. a heterologous nucleic acid of interest, in operative association with said promoter; wherein:
      said MmyR polypeptide shows at least 90% amino acid sequence identity with the sequence of SEQ ID NO: 12, optionally excluding the first 6 listed amino acids;
      said MmfR polypeptide shows at least 90% amino acid sequence identity with the sequence of SEQ ID NO: 11 said MmyR polypeptide and/or said MmfR polypeptide being effective to repress the function of said repressible promoter; and
      said MmfL polypeptide shows at least 90% amino acid sequence identity with the sequence of SEQ ID NO: 17 said MmfL polypeptide being effective to produce said product which alleviates or removes repression of said repressible promoter by said MmyR polypeptide and/or said MmfR polypeptide.

3. The expression cassette according to claim 1, wherein the regulatory portion(s) comprises both an mmyR nucleic acid sequence and an m13mfR nucleic acid sequence as defined in claim 1.

4. The expression cassette according to claim 1 further including a third regulatory element, which includes a nucleic acid sequence mmyB encoding an MmyB polypeptide, wherein said MmyB polypeptide shows at least 90% amino acid sequence identity with the MmyB amino acid sequence set out in EMBL AJ276673 said MmyB polypeptide being effective to bind DNA.

5. The expression cassette according to claim 1, wherein the regulatory portion(s) comprise(s) at least a portion of SEQ ID NO: 18 or SEQ ID NO: 19, or a variant thereof having at least 90% nucleic acid sequence identity to the nucleic acid sequence of SEQ ID NO: 18 or SEQ ID NO: 19.

6. The expression cassette according to claim 1, wherein the repressible promoter is a promoter of a methylenomycin biosynthetic gene or a promoter of a methylenomycin regulatory gene.

7. The expression cassette according to claim 1, wherein the repressible promoter comprises an mmyTOG promoter or an mmy . . . XCAPK promoter or an mmfLHP promoter or an mmyYF promoter or an mmyBQE promoter, wherein:
  a. the mmyTOG promoter comprises a sequence having at least 60% nucleic acid identity with a fragment of at least 30 residues of residues 5452 to 5675 of SEQ ID NO: 18;
  b. the mmfLHP promoter comprises a sequence having at least 60% nucleic acid identity with a fragment of at least 30 residues of residues 4716 to 4909 of SEQ ID NO: 19;
  c. the mmy . . . XCAPK promoter comprises a sequence having at least 60% nucleic acid identity with a fragment of at least 30 residues of the complement of residues 18892 to 19123 or 15404 to 15977 of EMBL AJ276673;
  d. the mmyYF promoter comprises a fragment of at least 30 residues of residues 18892 to 19123 of EMBL AJ276673; and
  e. the mmyBQE promoter comprises a fragment of at least 30 residues of the complement of residues 18892 to 19123 of EMBL AJ276673.

8. The expression cassette according to claim 7 wherein:
  a. at least part of at least one of the nucleic acid sequences mmyT, mmyO and mmyG is present in the regulatory portion(s), in operative association with the mmyTOG promoter;
  b. at least part of at least one of the nucleic acid sequences mmyD, mmyX, mmyC, mmyA, mmyP and mmyK, and optionally at least part of at least one of the nucleic acid sequences mmyB, mmyQ, and mmyE, is present in the regulatory portion(s) in operative association with the mmy . . . XCAPK promoter;
  c. at least part of at least one of the nucleic acid sequences mmfP and mmfH is present in the regulatory portion(s), in operative association with the mmfLHP promoter;
  d. at least part of at least one of the nucleic acid sequences mmyY and mmyF is present in the regulatory portion(s), in operative association with the mmyYF promoter; and
  e. at least part of at least one of the nucleic acid sequences mmyB, mmyQ and mmyE is present in the regulatory portion(s) in operative association with the mmyBQE promoter;
and wherein:
  said mmyT nucleic acid sequence encodes a polypeptide which shows at least 90% amino acid sequence identity with the sequence of SEQ ID NO: 22 and retains mmy polypeptide function;
  said mmyO nucleic acid sequence encodes a polypeptide which shows at least 90% amino acid sequence identity with the sequence of SEQ ID NO: 23 and retains mmy polypeptide function;
  said mmyG nucleic acid sequence encodes a polypeptide which shows at least 90% amino acid sequence identity with the sequence of SEQ ID NO: 24 and retains mmy polypeptide function;
  said mmfP nucleic acid sequence encodes a polypeptide which shows at least 90% amino acid sequence identity with the sequence of SEQ ID NO: 20 and retains mmf polypeptide function;
  said mmfH nucleic acid sequence encodes a polypeptide which shows at least 90% amino acid sequence identity with the sequence of SEQ ID NO: 21 and retains mmf polypeptide function;
  said mmyD, mmyX, mmyC, mmyA, mmyP, mmyK, mmyB, mmyQ, mmyE, mmyY and mmyF nucleic acid sequences each encode a polypeptide which show at least 90% amino acid sequence identity with the corresponding amino acid sequences set out in EMBL AJ276673 and retains mmy polypeptide function.

9. The expression cassette according to claim 8, further including a third regulatory element which includes a nucleic acid sequence mmyB encoding an MmyB polypeptide, wherein:
  (a) the mmfL nucleic acid sequence of the second regulatory element is also in operative association with the mmfLHP repressible promoter; or
  (b) the mmyB nucleic acid sequence of the third regulatory element is in operative association with the same mmyBQE repressible promoter; or
  (c) the mmfL nucleic acid sequence of the second regulatory element is also in operative association with the mmfLHP repressible promoter and the mmyB nucleic acid sequence of the third regulatory element is in operative association with the same mmyBQE repressible promoter; and wherein:
  the MmyB polypeptide shows at least 90% amino acid sequence identity with the MmyB amino acid sequence set out in EMBL AJ276673 said MmyB polypeptide being effective to bind DNA;
  the mmfLHP repressible promoter comprises a sequence having at least 60% nucleic acid identity with a fragment of at least 30 residues of residues 4716 to 4909 of SEQ ID NO: 19; and
  the mmyBQE repressible promoter comprises a fragment of at least 30 residues of the complement of residues 18892 to 19123 of EMBL AJ276673.

10. The expression cassette according to claim 1, wherein the regulatory portion(s) include(s) at least one of the nucleic acid sequences mmfP and mmfH, and wherein:
  said mmfP nucleic acid sequence encodes a polypeptide which shows at least 90% amino acid sequence identity with SEQ ID NO: 20 and is effective to regulate methylenomycin production; and
  said mmfH nucleic acid sequence encodes a polypeptide which shows at least 90% amino acid sequence identity with SEQ ID NO: 21 and is effective to regulate methylenomycin production.

11. The expression cassette according to claim 1, wherein the first regulatory element also includes a promoter operatively linked to at least one of the mmyR nucleic acid sequence and the mmfR nucleic acid sequence.

12. The expression cassette according to claim 11 wherein (i) the mmyR nucleic acid sequence is operatively linked to an mmyR promoter; or (ii) the mmfR nucleic acid sequence is operatively linked to an mmfR promoter; or (iii) both the mmyR nucleic acid sequence is operatively linked to an mmyR promoter and the mmfR nucleic acid sequence is operatively linked to an mmfR promoter, wherein:
  a. the mmyR promoter comprises a sequence having at least 60% nucleic acid identity with a fragment of at least 30 residues of residues 7965 to 8132 of SEQ ID NO: 19, optionally excluding residues 8113 to 8132; and
  b. the mmfR promoter comprises a sequence having at least 60% nucleic acid identity with a fragment of at least 30 residues of residues 4613 to 4806 of SEQ ID NO: 18.

13. The expression cassette according to claim 1, wherein the second regulatory element includes a promoter operatively linked to the mmfL nucleic acid sequence.

14. The expression cassette according to claim 13, wherein the promoter is an mmfL promoter, wherein the mmfL promoter comprises a sequence having at least 60% nucleic acid identity with a fragment of at least 30 residues of residues 4716 to 4909 of SEQ ID NO: 19.

15. The expression cassette according to claim 1 comprising at least one of an mmfL promoter and an mmfR promoter, the mmfL and/or the mmfR promoter comprising a palindromic sequence having the half-site 5'-GG(T/C)CGGT(A/T)(T/C)G(T/G)-3' (SEQ ID NO: 1), or a variant thereof having sequence identity at seven or more corresponding positions within the half-site, wherein:
  said mmfL promoter comprises a sequence having at least 60% nucleic acid identity with a fragment of at least 30 residues of residues 4716 to 4909 of SEQ ID NO: 19; and
  said mmfR promoter comprises a sequence having at least 60% nucleic acid identity with a fragment of at least 30 residues of residues 4613 to 4806 of SEQ ID NO: 18.

16. The expression cassette according to claim 15, wherein the palindromic sequence has the half-site 5'GGAAGGTATTA-3' (SEQ ID NO: 2).

17. The expression cassette according to claim 1 having a bi-directional mmfL/mmfR promoter, in operative association with the nucleic acid sequences mmfL and mmfR, wherein:
  said mmfL promoter comprises a sequence having at least 60% nucleic acid identity with a fragment of at least 30 residues of residues 4716 to 4909 of SEQ ID NO: 19; and
  said mmfR promoter comprises a sequence having at least 60% nucleic acid identity with a fragment of at least 30 residues of residues 4613 to 4806 of SEQ ID NO: 18.

18. The expression cassette according to claim 5 comprising a sequence having at least 90% nucleic acid identity with a fragment of at least 30 residues of residues 3551 to 5451 of SEQ ID NO: 18.

19. The expression cassette according to claim 1, wherein the nucleic acid of interest is inserted into the regulatory portion.

20. The expression cassette according to claim 19, wherein the insertion is by means of homologous recombination.

21. The expression cassette according to claim 1, wherein, apart from the repressible promoter, the nucleic acid of interest is not additionally in operative association with any promoter not derived from, or a variant of, a promoter of the methlenomycin gene cluster.

22. The expression cassette according to claim 1, wherein the regulatory portion(s) include(s) nucleic acid having at least 90% nucleic acid sequence identity with the sequence from residue 796 to a residue between 5676 and 8817 inclusive of SEQ ID NO: 18, and wherein the nucleic acid sequence of interest is inserted into or downstream of the mmyTOG region, or part thereof, in operative association with the mmyTOG promoter,
wherein:
  said mmyTOG promoter comprises a sequence having at least 60% nucleic acid identity with a fragment of at least 30 residues of residues 5452 to 5675 of SEQ ID NO: 18; and
  said mmyTOG region comprises the mmyT, mmyO and mmyG nucleic acid sequences,
and wherein:
  a. the mmyT nucleic acid sequence compnses a sequence having at least 90% nucleic acid identity with the sequence of residues 5676 to 6401 of SEQ ID NO: 18;
  b. the mmyO nucleic acid sequence comprises a sequence having at least 90% nucleic acid identity with the sequence of residues 6432 to 7553 of SEQ ID NO: 18; and
  c. the mmyG nucleic acid sequence comprises a sequence having at least 90% nucleic acid identity with the sequence of residues 7636 to 8817 of SEQ ID NO: 18.

23. The expression cassette according to claim 1, wherein the regulatory portion(s) include(s) nucleic acid having at least 90% nucleic acid sequence identity with the sequence from residues 796 to residue 5451 inclusive of SEQ ID NO: 18, and wherein the nucleic acid of interest is inserted into or downstream of the mmfHP region, in operative association with the mmfLHP promoter, wherein:
  said mmfLHP promoter comprises a sequence having at least 60% nucleic acid identity with a fragment of at least 30 residues of residues 4716 to 4909 of SEQ ID NO: 19; and
  said mmfHP region comprises the mmfH and mmfP nucleic acid sequence, and wherein:
  a. the mmfH nucleic acid sequence compnses a sequence having at least 90% nucleic acid identity with the sequence of residues 5968 to 7170 of SEQ ID NO: 19; and
  b. the mmfP nucleic acid sequence comprises a sequence having at least 90% nucleic acid identity with the sequence of residues 7167 to 7964, optionally excluding residues 7167 to 7169, of SEQ ID NO: 19.

24. The vector or set of vectors comprising an expression cassette according to claim 1.

25. The expression system comprising an expression cassette according to claim 1.

26. The expression system according to claim 25 which comprises a bacterial cell.

27. The expression system according to claim 26, wherein the bacterium is a streptomycete.

28. The expression system according to claim 25 further comprising a nucleic acid sequence mmyB, encoding an MmyB polypeptide wherein said MmyB polypeptide shows at least 90% amino acid sequence identity with the MmyB amino acid sequence set out in EMBL AJ276673 said MmyB polypeptide being effective to bind DNA.

29. The expression system according to claim 28, wherein the mmyB nucleic acid sequence is present within the expression cassette.

30. The expression system according to claim 28, wherein the mmyB nucleic acid sequence is present as part of the host cell genome.

31. The expression system according to claim 28, wherein the mmyB nucleic acid sequence is located on an SCP1 or pSV1 plasmid.

32. The expression system according to claim 25 which lacks the ability to translate the codon TTA (UUA in mRNA).

33. The expression system according to claim 28, wherein at least one of the nucleic acid sequences mmfL and mmyB is modified to lack a naturally occurring TTA codon.

34. A method of expressing a nucleic acid of interest, the method comprising providing an expression system according to claim 25 and maintaining the expression system under conditions suitable for expression of the nucleic acid of interest.

35. The method according to claim 34 for expressing the nucleic acid of interest substantially only when the host cell culture reaches high cell density.

36. The method according to claim 35 for expressing the nucleic acid of interest substantially only at or close to the stationary phase of host cell culture.

37. The method of expressing a nucleic acid of interest, the method comprising:
  a. providing in an expression system at least one regulatory portion as defined in claim 1;
  b. providing in the expression system the nucleic acid of interest;
  c. operatively associating the nucleic acid of interest with the repressible promoter of the regulatory portion(s); and
  d. maintaining the expression system under conditions suitable for the expression of the nucleic acid of interest.

38. The method according to claim 37, wherein the step of operative association occurs prior to introducing the regulatory portion(s) and nucleic acid of interest into the expression system.

39. The method according to claim 34, wherein the nucleic acid of interest is brought into operative association with the repressible promoter by inserting the nucleic acid of interest downstream of the repressible promoter.

40. The method according to claim 34, wherein the nucleic acid of interest is brought into operative association with the repressible promoter by inserting the repressible promoter into nucleic acid containing the nucleic acid of interest.

41. A method comprising providing a nucleic acid expression product produced by the method according to claim 34 and subjecting it to one or more purification steps.

42. An expression system comprising a vector or set of vectors according to claim 24.

43. An expression cassette according to claim 1 wherein:
  a. the MmyR polypeptide shows at least 90% amino acid sequence identity with residues 40 to 49 of SEQ ID NO: 12; and/or
  b. the MmfR polypeptide shows at least 90% amino acid sequence identity with residues 61 to 70 of SEQ ID NO: 11; and/or
  c. the MmfL polypeptide shows at least 90% amino acid sequence identity with at least one of (i) residues 77 to 87 and (ii) residues 240 to 255 of SEQ ID NO: 17.

44. An expression cassette according to claim 1 wherein:
  a. the mmyR nucleic acid sequence comprises a sequence having at least 90% nucleic acid identity with the sequence of residues 8115 to 8726 of SEQ ID NO: 19 (optionally excluding residues 8115 to 8132); and/or
  b the mmfR nucleic acid sequence comprises a sequence having at least 90% nucleic acid identity with the sequence of residues 4807 to 5451 of SEQ ID NO: 18; and/or
  c. the mmfL nucleic acid sequence comprises a sequence having at least 90% nucleic acid identity with the sequence of residues 4910 to 5971 of SEQ ID NO: 19.

45. An expression cassette according to claim 1 wherein:
  a. the mmyR nucleic acid sequence shows at least 90% nucleic acid sequence identity with the sequence of SEQ ID NO: 19 which corresponds to amino acid resides 40 to 49 of SEQ ID NO: 12; and/or
  b. the mmfR nucleic acid sequence shows at least 90% nucleic acid sequence identity with the sequence of SEQ ID NO: 18 which corresponds to amino acid residues 61 to 70 of SEQ ID NO: 11; and/or
  c. the mmfL nucleic acid sequence shows at least 90% nucleic acid sequence identity with the sequence of SEQ ID NO: 19 which corresponds to at least one of (i) amino acid residues 77 to 87 and (ii) amino acid residues 240 to 255 of SEQ ID NO: 17.

46. An expression cassette according to claim 8 wherein:
  a. the mmfP nucleic acid sequence encodes an MmfP polypeptide having the amino acid sequence of SEQ ID NO: 20; and/or
  b. the mmfH nucleic acid sequence encodes an MmfH polypeptide having the amino acid sequence of SEQ ID NO: 21; and/or
  c. the mmyT nucleic acid sequence encodes an MmyT polypeptide having the amino acid sequence of SEQ ID NO: 22; and/or
  d. the mmyO nucleic acid sequence encodes an MmyO polypeptide having the amino acid sequence of SEQ ID NO: 23; and/or
  e. the mmyG nucleic acid sequence encodes an MmyG polypeptide having the amino acid sequence of SEQ ID NO: 24; and/or
  f. the mmyB nucleic acid sequence encodes an MmyB polypeptide having the amino acid sequence set out in EMBL AJ276673.

47. An expression cassette according to claim 8 wherein:
  a. the mmfH nucleic acid sequence comprises a sequence having at least 90% nucleic acid identity with the sequence of residues 5968 to 7170 of SEQ ID NO: 19; and/or
  b. the mmfP nucleic acid sequence comprises a sequence having at least 90% nucleic acid identity with the sequence of residues 7167 to 7964, optionally excluding residues 7167 to 7169, of SEQ ID NO: 19; and/or
  c. the mmyT nucleic acid sequence comprises a sequence having at least 90% nucleic acid identity with the sequence of residues 5676 to 6401 of SEQ IID NO: 18; and/or
  d. the mmyO nucleic acid sequence comprises a sequence having at least 90% nucleic acid identity with the sequence of residues 6432 to 7553 of SEQ ID NO: 18; and/or
  e. the mmyG nucleic acid sequence comprises a sequence having at least 90% nucleic acid identity with the sequence of residues 7636 to 8817 of SEQ ID NO: 18; and/or
  f. the mmyB nucleic acid sequence comprises a sequence having at least 90% nucleic acid identity with the sequence of the complement of residues 18032 to 11892 of EMBL AJ276673.

48. The expression cassette according to claim 8, wherein the nucleic acid of interest is inserted into the regulatory portion.

49. The expression cassette according to claim 48, wherein the nucleic acid of interest is inserted within:
a. a nucleic acid sequence mmyT, mmyO or mmyG, in operative association with an mmyTOG promoter;
b. a nucleic acid sequence mmyD, mmyX, mmyC, mmyA, mmyP or mmyK or optionally a nucleic acid sequence mmyB, mmyQ or mmyE, in operative association with an mmy . . . XCAPK promoter;
c. a nucleic acid sequence mmfH or mmfP, in operative association with an mmfLHP promoter;
d. a nucleic acid sequence mmyY or mmyF, in operative association with an mmyYF promoter; and/or
e. a nucleic acid sequence mmyB, mmyQ or mmyE, in operative association with an mmyBQE promoter; wherein:
said mmyT nucleic acid sequence encodes a polypeptide which shows at least 90% amino acid sequence identity with the sequence of SEQ ID NO: 22 and retains mmy polypeptide function;
said mmyO nucleic acid sequence encodes a polypeptide which shows at least 90% amino acid sequence identity with the sequence of SEQ ID NO: 23 and retains mmy polypeptide function;
said mmyG nucleic acid sequence encodes a polypeptide which shows at least 90% amino acid sequence identity with the sequence of SEQ ID NO: 24 and retains mmy polypeptide function;
said mmfP nucleic acid sequence encodes a polypeptide which shows at least 90% amino acid sequence identity with the sequence of SEQ ID NO: 20 and retains mmf polypeptide function;
said mmfH nucleic acid sequence encodes a polypeptide which shows at least 90% amino acid sequence identity with the sequence of SEQ ID NO: 21c and retains mmf polypeptide function;
said mmyD, mmyX, mmyC, mmyA, mmyP, mmyK, mmyB, mmyQ, mmyE, mmyY and mmyF nucleic acid sequence each encodes a polypeptide which shows at least 90% amino acid sequence identity with the corresponding amino acid sequences set out in EMBL AJ276673 and retains mmf polypeptide function; and wherein:
a. the mmyTOG promoter comprises a sequence having at least 60% nucleic acid identity with a fragment of at least 30 residues of residues 5452 to 5675 of SEQ ID NO: 18;
b. the mmfLHP promoter comprises a sequence having at least 60% nucleic acid identity with a fragment of at least 30 residues of residues 4716 to 4909 of SEQ ID NO: 19;
c. the mmy . . . XCAPK promoter comprises a sequence having at least 60% nucleic acid identity with a fragment of at least 30 residues of the complement of residues 18892 to 19123 or 15404 to 15977 of EMBL AJ276673;
d. the mmyYF promoter comprises a fragment of at least 30 residues of residues 18892 to 19123 of EMBL AJ276673; and
e. the mmyBQE promoter comprises a fragment of at least 30 residues of the complement of residues 18892 to 19123 of EMBL AJ276673.

50. An expression cassette for the expression of a nucleic acid of interest, the expression cassette including:
a. at least one regulatory portion including:
a first regulatory element which includes a nucleic acid sequence mmyR encoding an MmyR polypeptide and/or a nucleic acid sequence mmfR encoding an MmfR polypeptide;
ii. a second regulatory element which includes the nucleic acid sequence mmfL encoding an MmfL polypeptide; and
iii. a repressible promoter, the function of which is repressed by the expression product of the first regulatory element, that repression being alleviated or removed by a product, the production of the last-mentioned product being conferred by the MmfL polypeptide; and
b. a heterologous nucleic acid of interest, in operative association with said promoter; wherein:
a. said MmyR polypeptide has the amino acid sequence of SEQ ID NO: 12 (optionally excluding the first 6 listed amino acids);
b. said MmfR polypeptide has the amino acid sequence of SEQ ID NO: 11; and
c. said MmfL polypeptide has the amino acid sequence of SEQ ID NO: 17.

* * * * *

SEQUENCE LISTING

<160> NUMBER OF SEQ ID NOS: 35

<210> SEQ ID NO 1
<211> LENGTH: 11
<212> TYPE: DNA
<213> ORGANISM: Artificial
<220> FEATURE:
<223> OTHER INFORMATION: Consensus sequence

<400> SEQUENCE: 1

```
ggycggtwyg k                                                11
```

```
<210> SEQ ID NO 2
<211> LENGTH: 11
<212> TYPE: DNA
<213> ORGANISM: Streptomyces coelicolor

<400> SEQUENCE: 2
ggaaggtatt a                                                11

<210> SEQ ID NO 3
<211> LENGTH: 216
<212> TYPE: PRT
<213> ORGANISM: Streptomyces sp.

<400> SEQUENCE: 3
```

Leu Thr Pro Lys Gln Glu Arg Ala Phe Arg Thr Arg Thr Gln Leu Val
1               5                  10                  15

Leu Ser Ala Ala Glu Ala Phe Asp Arg Gln Gly Phe Ala Thr Ala Ser
            20                  25                  30

Leu Thr Ala Ile Ser Asn Ser Ala Gly Val Ser Asn Gly Ala Leu His
        35                  40                  45

Phe His Phe Glu Ser Lys Glu Ala Leu Ala Ala Val Glu Ala Glu
    50                  55                  60

Ala Ala Glu Arg Met Arg Thr Ile Val Asp Gly Ala Ala Arg Arg Gly
65                  70                  75                  80

Ala Ser Ala Leu Gln Ala Leu Val Asp Thr Ser His Ala Val Met Leu
                85                  90                  95

Arg Leu Arg Gln Asp Val Val Arg Ala Gly Phe Arg Leu Ser Gly
            100                 105                 110

Asp Ala Ala Arg Gln Ala Thr His Asp Leu Pro Glu His Trp Arg Gln
        115                 120                 125

Ser Val Val Arg Leu Leu Glu Arg Ala Gly Arg Asp Gly Ser Leu Thr
    130                 135                 140

Ser Ala Val Thr Pro Ser Asp Val Ala Gly Val Val Thr Ala Thr Val
145                 150                 155                 160

Leu Gly Phe Gly Val Leu Ala Arg Phe Asp Ser Ala Trp Leu Ala Ser
                165                 170                 175

Gly Ser Leu Ser Gly Phe Trp Lys Leu Met Leu Pro Met Ile Ala Ala
            180                 185                 190

Gly Pro Val Glu Arg Gly Glu Leu Asp Cys Arg Pro Ala Val Pro Ala
        195                 200                 205

Asp Val Arg Arg Ala Pro Ala Val
    210                 215

```
<210> SEQ ID NO 4
<211> LENGTH: 196
<212> TYPE: PRT
<213> ORGANISM: Streptomyces sp.

<400> SEQUENCE: 4
```

Met Thr Lys Gln Glu Arg Ala Thr Arg Thr Arg Asp Ala Leu Ile Lys
1               5                  10                  15

Ser Ala Ala Arg Glu Phe Asp Glu His Gly Tyr Ala Leu Ala Lys Leu
            20                  25                  30

Ser Ala Ile Ser Ser Gly Ala Gly Val Ser Pro Gly Ala Leu His Phe
        35                  40                  45

His Phe Glu Asn Lys Val Ala Ala Val Glu Ile Asp Ala Ser Thr
        50                  55                  60

Thr Leu Arg Arg Thr Ala Arg Ile Val Tyr His Gln Arg Ser Asn Ala
65                  70                  75                  80

Leu Gln Asn Leu Ala Asp Thr Thr His Ala Leu Ala Arg Leu Val Arg
                85                  90                  95

Glu Asp Val Val Arg Ala Gly Phe Arg Leu Ser Cys Ser Gln Leu
            100                 105                 110

Cys Gly Thr Asp Leu Asn Leu Arg Gln Glu Trp Gln Ser Cys Val Gln
            115                 120                 125

Gln Arg Leu Ala Glu Ala Ala Asp Glu Gly Leu Leu Ala Ser Asp Ile
        130                 135                 140

Gly Gly Gln Gln Asp Leu Ala Arg Thr Ile Val Ala Ala Thr Ile Gly
145                 150                 155                 160

Leu Glu Ala Leu Cys Arg Asp Asn Gly Glu Trp Leu Ser Pro Gly Thr
                165                 170                 175

Val Thr Gly Leu Trp Arg Thr Leu Leu Pro Ile Val Ala Ala Pro Gly
            180                 185                 190

Arg Ser Pro Pro
        195

<210> SEQ ID NO 5
<211> LENGTH: 215
<212> TYPE: PRT
<213> ORGANISM: Streptomyces sp.

<400> SEQUENCE: 5

Met Ala Arg Gln Leu Arg Ala Glu Arg Thr Arg Ala Thr Ile Val Arg
1               5                   10                  15

Ala Ala Ala Asp Leu Phe Asp Arg His Gly Tyr Glu Ser Thr Ser Leu
            20                  25                  30

Ser Glu Ile Val Ala His Ala Gly Val Thr Lys Gly Ala Leu Tyr Phe
        35                  40                  45

His Phe Ala Ala Lys Glu Asp Leu Ala His Ala Ile Leu Glu Ile Gln
        50                  55                  60

Ser Arg Thr Ser Arg Arg Leu Ala Lys Asp Leu Asp Gly Arg Gly Tyr
65                  70                  75                  80

Ser Ser Leu Glu Ala Leu Met Arg Leu Thr Phe Gly Met Ala Arg Leu
                85                  90                  95

Cys Val Gln Gly Pro Val Leu Arg Ala Gly Thr Arg Leu Ala Thr Ala
            100                 105                 110

Gly Val Pro Val Arg Pro Pro Leu Pro His Pro Phe Thr Asp Trp Arg
            115                 120                 125

Glu Ile Ala Thr Ser Arg Leu Leu Asp Ala Val Arg Gln Ser Asp Val
        130                 135                 140

His Gln Asp Ile Asp Val Asp Ser Val Ala His Thr Leu Val Ser Ser
145                 150                 155                 160

Val Val Gly Thr Cys Val Val Gly Gly Thr Leu Glu Pro Ala Gly Arg
                165                 170                 175

Gln Pro Arg Arg Leu Ala Glu Met Trp Tyr Ile Leu Ile Arg Gly Met
            180                 185                 190

Val Pro Val Thr Arg Arg Ala Arg Tyr Val Thr Leu Ala Ala Arg Leu
        195                 200                 205

Glu Gln Glu Thr Gly Thr Thr

```
                210                 215

<210> SEQ ID NO 6
<211> LENGTH: 215
<212> TYPE: PRT
<213> ORGANISM: Streptomyces sp.

<400> SEQUENCE: 6

Met Ala Arg Gln Leu Arg Ala Glu Gln Thr Arg Ala Thr Ile Ile Gly
1               5                   10                  15

Ala Ala Ala Asp Leu Phe Asp Arg Arg Gly Tyr Glu Ser Thr Thr Leu
            20                  25                  30

Ser Glu Ile Val Ala His Ala Gly Val Thr Lys Gly Ala Leu Tyr Phe
        35                  40                  45

His Phe Ala Ala Lys Glu Asp Leu Ala His Ala Ile Leu Glu Ile Gln
    50                  55                  60

Ser Arg Thr Ser Arg Arg Leu Ala Lys Asp Leu Asp Gly Arg Gly Tyr
65                  70                  75                  80

Ser Ser Leu Glu Ala Leu Met Arg Leu Thr Phe Gly Met Ala Arg Leu
                85                  90                  95

Cys Val Gln Gly Pro Val Leu Arg Ala Gly Leu Arg Leu Ala Thr Ala
            100                 105                 110

Gly Val Pro Val Arg Pro Pro Leu Pro His Pro Phe Thr Glu Trp Arg
        115                 120                 125

Glu Ile Ala Thr Ser Arg Leu Leu Asp Ala Val Arg Gln Ser Asp Val
    130                 135                 140

His Gln Asp Ile Asp Val Asp Ser Val Ala His Thr Leu Val Cys Ser
145                 150                 155                 160

Val Val Gly Thr Arg Val Val Gly Gly Thr Leu Glu Pro Ala Gly Arg
                165                 170                 175

Glu Pro Arg Arg Leu Ala Glu Met Trp Tyr Ile Leu Ile Arg Gly Met
            180                 185                 190

Val Pro Val Thr Arg Arg Ala Arg Tyr Val Thr Leu Ala Ala Arg Leu
        195                 200                 205

Glu Gln Glu Thr Gly Thr Ala
    210                 215

<210> SEQ ID NO 7
<211> LENGTH: 221
<212> TYPE: PRT
<213> ORGANISM: Streptomyces sp.

<400> SEQUENCE: 7

Val Ala Glu Gln Val Arg Ala Ile Arg Thr Arg Gln Ala Ile Leu Ser
1               5                   10                  15

Ala Ala Ala Arg Val Phe Asp Glu Arg Gly Tyr Gln Ala Ala Thr Ile
            20                  25                  30

Ser Glu Ile Leu Thr Val Ala Gly Val Thr Lys Gly Ala Leu Tyr Phe
        35                  40                  45

His Phe Gln Ser Lys Glu Asp Leu Ala Gln Gly Leu Thr Ala Gln
    50                  55                  60

Asn Glu Asp Leu Leu Pro Glu Arg Pro Ala Lys Leu Gln Glu Val
65                  70                  75                  80

Val Asp Ala Val Met Leu His Thr His Arg Leu Arg Thr Asn Pro Met
                85                  90                  95

Val Arg Ala Gly Val Arg Leu Ser Leu Asp Val Asn Ala Gly Gly Leu
```

```
                100              105              110
Asp Arg Ser Ala Pro Phe Arg Asn Trp Val Asp Lys Phe Thr Asp Leu
            115                 120                 125

Leu Glu Lys Ala Gln Ala Gln Gly Glu Leu Leu Pro His Val Val Pro
        130                 135                 140

Ala Glu Thr Ala Asp Val Ile Thr Gly Ala Tyr Gly Val Gln Ser
145                 150                 155                 160

Met Ser Gln Ala Leu Thr Glu His Gln Asp Leu Gly Gln Arg Val Asn
                165                 170                 175

Ala Leu Leu Arg His Leu Met Pro Ser Ile Ala Gln Pro Ser Val Leu
            180                 185                 190

Ala Ser Leu His Leu Gly Glu Ser Arg Ala Glu Glu Val Tyr Leu Glu
        195                 200                 205

Ala Arg Gln Leu Ala Arg Glu Gln Ala Asp Glu Asp
    210                 215                 220

<210> SEQ ID NO 8
<211> LENGTH: 215
<212> TYPE: PRT
<213> ORGANISM: Streptomyces sp.

<400> SEQUENCE: 8

Met Ala Lys Gln Asp Arg Ala Ile Arg Thr Arg Gln Thr Ile Leu Asp
1               5                   10                  15

Ala Ala Ala Gln Val Phe Glu Lys Gln Gly Tyr Gln Ala Ala Thr Ile
            20                  25                  30

Thr Glu Ile Leu Lys Val Ala Gly Val Thr Lys Gly Ala Leu Tyr Phe
        35                  40                  45

His Phe Gln Ser Lys Glu Glu Leu Ala Leu Gly Val Phe Asp Ala Gln
    50                  55                  60

Glu Pro Pro Gln Ala Val Pro Glu Gln Pro Leu Arg Leu Gln Glu Leu
65                  70                  75                  80

Ile Asp Met Gly Met Leu Phe Cys His Arg Leu Arg Thr Asn Val Val
                85                  90                  95

Ala Arg Ala Gly Val Arg Leu Ser Met Asp Gln Gln Ala His Gly Leu
            100                 105                 110

Asp Arg Arg Gly Pro Phe Arg Arg Trp His Glu Thr Leu Leu Phe Leu
        115                 120                 125

Leu Asn Gln Ala Lys Glu Asn Gly Glu Leu Leu Pro His Val Val Thr
    130                 135                 140

Thr Asp Ser Ala Asp Leu Tyr Val Gly Thr Phe Ala Gly Ile Gln Val
145                 150                 155                 160

Val Ser Gln Thr Val Ser Asp Tyr Gln Asp Leu Glu His Arg Tyr Ala
                165                 170                 175

Leu Leu Gln Lys His Ile Leu Pro Ala Ile Ala Val Pro Ser Val Leu
            180                 185                 190

Ala Ala Leu Asp Leu Ser Glu Glu Arg Gly Ala Arg Leu Ala Ala Glu
        195                 200                 205

Leu Ala Pro Thr Gly Lys Asp
    210                 215

<210> SEQ ID NO 9
<211> LENGTH: 232
<212> TYPE: PRT
<213> ORGANISM: Streptomyces sp.
```

<400> SEQUENCE: 9

```
Met Ala Val Arg His Glu Arg Val Ala Val Arg Gln Glu Arg Ala Val
1               5                   10                  15

Arg Thr Arg Gln Ala Ile Val Arg Ala Ala Ser Val Phe Asp Glu
            20                  25                  30

Tyr Gly Phe Glu Ala Ala Thr Val Ala Glu Ile Leu Ser Arg Ala Ser
            35                  40                  45

Val Thr Lys Gly Ala Met Tyr Phe His Phe Ala Ser Lys Glu Glu Leu
    50                  55                  60

Ala Arg Gly Val Leu Ala Glu Gln Thr Leu His Val Ala Val Pro Glu
65                  70                  75                  80

Ser Gly Ser Lys Ala Gln Glu Leu Val Asp Leu Thr Met Leu Val Ala
                85                  90                  95

His Gly Met Leu His Asp Pro Thr Leu Arg Ala Gly Thr Arg Leu Ala
                100                 105                 110

Leu Asp Gln Gly Ala Val Asp Phe Ser Asp Ala Asn Pro Phe Gly Glu
            115                 120                 125

Trp Gly Asp Ile Cys Ala Gln Leu Leu Ala Glu Ala Gln Glu Arg Gly
    130                 135                 140

Glu Val Leu Pro His Val Asn Pro Lys Lys Thr Gly Asp Phe Ile Val
145                 150                 155                 160

Gly Cys Phe Thr Gly Leu Gln Ala Val Ser Arg Val Thr Ser Asp Arg
                165                 170                 175

Gln Asp Leu Gly His Arg Ile Ser Val Met Trp Asn His Val Leu Pro
            180                 185                 190

Ser Ile Val Pro Ala Ser Met Leu Thr Trp Ile Glu Thr Gly Glu Glu
        195                 200                 205

Arg Ile Gly Lys Val Ala Ala Ala Glu Ala Glu Ala Ala Glu
        210                 215                 220

Ala Ser Glu Ala Ala Ser Asp Glu
225                 230
```

<210> SEQ ID NO 10
<211> LENGTH: 276
<212> TYPE: PRT
<213> ORGANISM: Streptomyces sp.

<400> SEQUENCE: 10

```
Met Ala Lys Gln Ala Arg Ala Val Gln Thr Trp Arg Ser Ile Val Asp
1               5                   10                  15

Ala Ala Ala Ser Val Phe Asp Asp Tyr Gly Tyr Glu Arg Ala Ala Ile
            20                  25                  30

Ser Glu Ile Leu Arg Arg Ala Lys Val Thr Lys Gly Ala Leu Tyr Phe
        35                  40                  45

His Phe Ala Ser Lys Glu Ala Ile Ala Gln Ala Ile Met Asp Glu Gln
    50                  55                  60

Thr Ser Thr Val Glu Phe Glu Gln Gly Ser Pro Leu Gln Ser Leu
65                  70                  75                  80

Val Asp Gly Gly Gln Gln Phe Ala Phe Ala Leu Arg His Asn Ser Met
                85                  90                  95

Ala Arg Ala Gly Thr Arg Leu Ser Ile Ala Gly Val Phe Leu Gly Gly
                100                 105                 110

Pro His Pro Trp Gly Asp Trp Ile Asp Ala Thr Ala Arg Met Leu Glu
            115                 120                 125
```

```
Leu Gly Gln Glu Arg Gly Glu Val Phe Pro Gln Ile Asp Pro Met Val
    130                 135                 140
Ser Ala Lys Ile Ile Val Ala Ser Phe Thr Gly Ile Gln Leu Val Ser
145                 150                 155                 160
Glu Ala Asp Ser Gly Arg Ala Asp Leu Arg Glu Gln Val Ala Glu Met
                165                 170                 175
Trp Arg His Ile Leu Pro Ser Ile Ala His Pro Gly Val Ile Ala His
                180                 185                 190
Ile Lys Pro Glu Gly Arg Val Asp Leu Ala Ala Gln Ala Arg Glu Lys
                195                 200                 205
Ala Glu Arg Glu Glu Gln Glu Ala Arg Ile Ala Ala Glu Ala Lys Gly
    210                 215                 220
Ala Gly Ser Asp Pro Thr Ser Glu Gly Gly Thr Arg Ser Gly Gly Ser
225                 230                 235                 240
Gly Leu Arg Gly Gly Ser Gly Arg Gly Pro Arg Ala Gly Val Thr
                245                 250                 255
Gly Asp Glu Gly Asp Glu Pro Ala Gly Ala Gly Val Ala Ala Gly
                260                 265                 270
Gly Ile Val Ala
    275

<210> SEQ ID NO 11
<211> LENGTH: 214
<212> TYPE: PRT
<213> ORGANISM: Streptomyces coelicolor

<400> SEQUENCE: 11

Met Thr Ser Ala Gln Gln Pro Thr Pro Phe Ala Val Arg Ser Asn Val
1               5                   10                  15
Pro Arg Gly Pro His Pro Gln Glu Arg Ser Ile Lys Thr Arg Ala
                20                  25                  30
Gln Ile Leu Glu Ala Ala Ser Glu Ile Phe Ala Ser Arg Gly Tyr Arg
            35                  40                  45
Gly Ala Ser Val Lys Asp Val Ala Glu Arg Val Gly Met Thr Lys Gly
        50                  55                  60
Ala Val Tyr Phe His Phe Pro Ser Lys Glu Ser Leu Ala Ile Ala Val
65                  70                  75                  80
Val Glu Glu His Tyr Ala Arg Trp Pro Ala Ala Met Glu Glu Ile Arg
                85                  90                  95
Ile Gln Gly Phe Thr Pro Leu Glu Thr Val Glu Glu Met Leu His Arg
            100                 105                 110
Ala Ala Gln Ala Phe Arg Asp Asp Pro Val Met Gln Ala Gly Ala Arg
        115                 120                 125
Leu Gln Ser Glu Arg Ala Phe Ile Asp Ala Glu Leu Pro Leu Pro Tyr
    130                 135                 140
Val Asp Trp Thr His Leu Leu Glu Val Pro Leu Gln Asp Ala Arg Glu
145                 150                 155                 160
Ala Gly Gln Leu Arg Ala Gly Val Asp Pro Ala Ala Ala Arg Ser
                165                 170                 175
Leu Val Ala Ala Phe Gly Met Gln His Val Ser Asp Asn Leu His
                180                 185                 190
Gln Arg Ala Asp Ile Met Glu Arg Trp Gln Glu Leu Arg Glu Leu Met
        195                 200                 205
Phe Phe Ala Leu Arg Ala
    210
```

<210> SEQ ID NO 12
<211> LENGTH: 203
<212> TYPE: PRT
<213> ORGANISM: Streptomyces coelicolor

<400> SEQUENCE: 12

```
Val Lys Gln Ala Arg Ala Met Arg Thr Arg Asp Gln Val Leu Asp Ala
1               5                   10                  15

Ala Ala Glu Glu Phe Ala Leu His Gly Tyr Ala Gly Thr Asn Leu Ala
            20                  25                  30

Thr Val Ala Val Arg Thr Gly Met Thr Lys Gly Ala Leu Tyr Gly His
        35                  40                  45

Phe Pro Ser Lys Lys Ala Leu Ala Asp Glu Leu Val Ser Gln Ser Thr
    50                  55                  60

Glu Thr Trp Asn Thr Ile Gly Arg Ser Ile Ala Glu Thr Ala Cys Ala
65                  70                  75                  80

Pro Glu Thr Ala Leu Arg Ala Leu Val Leu Ala Val Ser Arg Gln Met
                85                  90                  95

Lys His Asp Ile Arg Phe Arg Ala Ala Leu Arg Leu Ala Ala Asp Cys
            100                 105                 110

Thr Met Pro Ala Gly Gly Ala Pro Asp Leu Leu Asp Arg Ile Arg Arg
        115                 120                 125

Glu Met Ala Ala Ala Arg Asp Thr Gln Gln Gln Ala Pro Tyr
    130                 135                 140

Ser Pro Leu Ala Thr Gln Pro Pro Asp Val Val His Leu Leu Leu
145                 150                 155                 160

Thr Val Ala Tyr Gly Leu Ser Phe Ala Ala Glu Arg Gly Ala Pro Gly
                165                 170                 175

Arg Ser Pro Ala Thr Thr Asp Lys Val Trp Glu Leu Leu Thr Ala
            180                 185                 190

Leu Gln Leu Glu Asp Ile Ser Thr Cys His Asn
        195                 200
```

<210> SEQ ID NO 13
<211> LENGTH: 301
<212> TYPE: PRT
<213> ORGANISM: Streptomyces sp.

<400> SEQUENCE: 13

```
Met Asp Ala Glu Ala Glu Val Val His Pro Gly Ile Glu Met Val
1               5                   10                  15

His Arg Thr Arg Pro Glu Asp Ala Phe Pro Arg Asn Trp Val Arg Leu
            20                  25                  30

Gly Arg Asp Arg Phe Ala Val Glu Ala Val Leu Pro His Asp His Pro
        35                  40                  45

Phe Phe Ala Pro Val Gly Asp Asp Leu His Asp Pro Leu Leu Val Ala
    50                  55                  60

Glu Ala Met Arg Gln Ala Ala Met Leu Ala Phe His Ala Gly Tyr Gly
65                  70                  75                  80

Ile Pro Leu Gly Tyr His Phe Leu Leu Thr Glu Leu Asp Tyr Val Cys
                85                  90                  95

His Pro Glu His Leu Gly Val Gly Gly Glu Pro Thr Glu Ile Gly Leu
            100                 105                 110

Glu Val Phe Cys Ser Asp Leu Lys Trp Arg Ala Gly Leu Pro Ala Gln
        115                 120                 125
```

```
Gly Arg Val Gly Trp Ala Val His Arg Gly Asp Arg Leu Ala Ala Thr
    130                 135                 140

Gly Val Ala Ala Thr Arg Phe Ser Thr Pro Lys Ala Tyr Arg Arg Met
145                 150                 155                 160

Arg Gly Asp Val Pro Val Glu Gly Ile Ser Leu Pro Glu Thr Ala Pro
                165                 170                 175

Val Pro Ala Ser Pro Ala Gly Arg Ala Arg Val Glu Asp Val Val Leu
            180                 185                 190

Ser Gly Thr Gly Arg Glu Gly Val Trp Glu Leu Arg Val Asp Thr Arg
    195                 200                 205

His Pro Thr Leu Phe Gln Arg Pro Asn Asp His Val Pro Gly Met Leu
    210                 215                 220

Leu Leu Glu Ala Ala Arg Gln Ala Ala Cys Leu Val Ala Gly Pro Ala
225                 230                 235                 240

Gly Ile Val Pro Val Glu Ala Arg Thr Arg Phe His Arg Tyr Ser Glu
                245                 250                 255

Phe Gly Ser Pro Cys Trp Ile Gly Ala Val Val Gln Pro Gly Ala Asp
            260                 265                 270

Glu Asp Thr Val Thr Val Arg Val Thr Gly His Gln Asp Gly Glu Thr
        275                 280                 285

Val Phe Ser Thr Val Leu Ser Gly Pro Arg Ala His Gly
    290                 295                 300

<210> SEQ ID NO 14
<211> LENGTH: 314
<212> TYPE: PRT
<213> ORGANISM: Streptomyces sp.

<400> SEQUENCE: 14

Met Pro Glu Ala Val Val Leu Ile Asn Ser Ala Ser Asp Ala Asn Ser
1               5                   10                  15

Ile Glu Gln Thr Ala Leu Pro Val Pro Met Ala Leu Val His Arg Thr
            20                  25                  30

Arg Val Gln Asp Ala Phe Pro Val Ser Trp Ile Pro Lys Gly Gly Asp
        35                  40                  45

Arg Phe Ser Val Thr Ala Val Leu Pro His Asp His Pro Phe Phe Ala
    50                  55                  60

Pro Val His Gly Asp Arg His Asp Pro Leu Leu Ile Ala Glu Thr Leu
65                  70                  75                  80

Arg Gln Ala Ala Met Leu Val Phe His Ala Gly Tyr Gly Val Pro Val
                85                  90                  95

Gly Tyr His Phe Leu Met Ala Thr Leu Asp Tyr Thr Cys His Leu Asp
            100                 105                 110

His Leu Gly Val Ser Gly Glu Val Ala Glu Leu Glu Val Glu Val Ala
        115                 120                 125

Cys Ser Gln Leu Lys Phe Arg Gly Gly Gln Pro Val Gln Gly Gln Val
    130                 135                 140

Asp Trp Ala Val Arg Arg Ala Gly Arg Leu Ala Ala Thr Gly Thr Ala
145                 150                 155                 160

Thr Thr Arg Phe Thr Ser Pro Gln Val Tyr Arg Arg Met Arg Gly Asp
                165                 170                 175

Phe Ala Thr Pro Thr Ala Ser Val Pro Gly Thr Ala Pro Val Pro Ala
            180                 185                 190

Ala Arg Ala Gly Arg Thr Arg Asp Glu Asp Val Val Leu Ser Ala Ser
```

```
               195                 200                 205
Ser Gln Gln Asp Thr Trp Arg Leu Arg Val Asp Thr Ser His Pro Thr
    210                 215                 220
Leu Phe Gln Arg Pro Asn Asp His Val Pro Gly Met Leu Leu Leu Glu
225                 230                 235                 240
Ala Ala Arg Gln Ala Ala Cys Leu Val Thr Gly Pro Ala Pro Phe Val
                245                 250                 255
Pro Ser Ile Gly Gly Thr Arg Phe Val Arg Tyr Ala Glu Phe Asp Ser
            260                 265                 270
Pro Cys Trp Ile Gln Ala Thr Val Arg Pro Gly Pro Ala Ala Gly Leu
        275                 280                 285
Thr Thr Val Arg Val Thr Gly His Gln Asp Gly Ser Leu Val Phe Leu
    290                 295                 300
Thr Thr Leu Ser Gly Pro Ala Phe Ser Gly
305                 310

<210> SEQ ID NO 15
<211> LENGTH: 314
<212> TYPE: PRT
<213> ORGANISM: Streptomyces sp.

<400> SEQUENCE: 15

Val Ala Val Pro Ala Arg Arg Thr Ala Phe Gln Thr Gly Arg Pro Ala
1               5                   10                  15
Arg Ala Ser Ala Met Thr Ser Thr Val Pro Arg Glu Leu Val His Arg
            20                  25                  30
Ala Ala Val Ala Glu Val Phe Leu Thr Gly Trp Ser Arg Thr Ala Glu
        35                  40                  45
Asn Arg Phe Ala Leu Thr Ala Gln Trp Pro Arg Ala His Ser Tyr Phe
    50                  55                  60
Thr Pro Val Asn Gly Cys Tyr Asp Pro Leu Leu Ala Ser Glu Thr Ile
65                  70                  75                  80
Arg Gln Val Gly Thr Leu Leu Ser His Ala Glu Phe Gly Val Ser Phe
                85                  90                  95
Gly Asp Gln Phe Leu Met Trp Asp Leu His His Ser Val Arg Pro Glu
            100                 105                 110
Gln Ala Gly Val Gly Ala Ala Pro Ala Asp Leu Glu Leu Asp Val Ile
        115                 120                 125
Cys Ser Asp Ile Arg Arg Gly Arg Arg Leu Ala Gly Met Arg Tyr
130                 135                 140
Glu Val Thr Leu Tyr Cys Gly Gly Gln Val Ile Ala Thr Gly Gly Ala
145                 150                 155                 160
Ala Phe Asp Cys Thr Ser Pro Ala Val Tyr Gln Arg Leu Arg Gly Asp
                165                 170                 175
Arg Val Gly Ala Thr Gly Val Arg Pro Leu Pro Gln Pro Leu Ala Pro
            180                 185                 190
Ala Ser Val Gly Arg Phe Leu Thr Thr Asp Val Leu Ser Ala Thr
        195                 200                 205
Glu Arg Pro Leu Glu Trp Gln Leu Arg Val Asp Glu Gln His Pro Val
    210                 215                 220
Leu Phe Asp His Pro Val Asp His Val Pro Gly Met Val Leu Met Glu
225                 230                 235                 240
Ser Ala Arg Gln Ala Ala Gln Ala Ile Asp Pro Ser Arg Pro Phe Leu
                245                 250                 255
```

-continued

```
Pro Thr Thr Met Arg Ser Glu Phe Ser Arg Tyr Ala Glu Leu Asp Arg
            260                 265                 270

Pro Cys Trp Ile Gln Ala Glu Pro Leu Pro Ala Ala Asp Asn Gly Asp
            275                 280                 285

Arg Gln Val Arg Val Thr Gly His Gln Asp Asp Thr Thr Val Phe Ser
        290                 295                 300

Cys Leu Ile Gly Thr Arg Gly Ala Ala Glu
305                 310

<210> SEQ ID NO 16
<211> LENGTH: 291
<212> TYPE: PRT
<213> ORGANISM: Streptomyces sp.

<400> SEQUENCE: 16

Leu Val His Arg Thr Ser Thr Ala Gln Val Leu Leu Thr Asp Trp Gln
1               5                   10                  15

Arg Leu Asp Asp Ala Arg Phe Ser Val Thr Ala Arg Trp Pro Leu Ser
            20                  25                  30

His Ala Phe Phe Thr Pro Val Gly Asp Gly Tyr Tyr Asp Pro Leu Met
        35                  40                  45

Cys Ala Glu Thr Ile Arg Gln Ile Ala Tyr Leu Leu Gly His Ala Glu
    50                  55                  60

Phe Ala Val Pro Phe Gly His Gln Phe Val Leu Trp Asp Leu Ser Val
65                  70                  75                  80

Ser Val Val Arg Pro Glu Leu Leu Arg Val Gly Leu Val Pro Ala Thr
                85                  90                  95

Val Asp Leu Ala Ile Thr Cys Val Glu Ile Lys Arg Arg Ala Gly Arg
            100                 105                 110

Leu Ser Gly Leu Gly Tyr Glu Ala Val Val Arg Arg Asp Gly Gln Val
        115                 120                 125

Val Ala Thr Gly Arg Ala Ser Val Thr Cys Thr Ser Pro Ala Val Tyr
    130                 135                 140

Gln Arg Ile Arg Pro Glu His Val Leu Thr Pro Glu His Arg Pro Leu
145                 150                 155                 160

Pro Leu Thr Ala Pro Ala Ala Pro Gln Ser Val Ala Arg Leu Ser Pro
                165                 170                 175

Thr Asp Val Val Leu Ser Pro Leu Asp Arg Glu Asn Arg Trp Gln Leu
            180                 185                 190

Arg Val Asp Thr Asn His Pro Val Leu Phe Asp His Trp Val Asp His
        195                 200                 205

Val Pro Gly Met Val Leu Met Glu Ala Ala Arg Gln Ala Ala Ala Ser
    210                 215                 220

Ala Leu Gly Arg Pro Ser Phe Met Pro Leu Gly Val Ala Gly Glu Phe
225                 230                 235                 240

Lys Arg Tyr Val Glu Leu Asp Ala Pro Cys Val Ile Glu Ser Glu Arg
                245                 250                 255

Leu Phe Gln Asp Val Pro Gly Ala Glu Glu Val Val Arg Val Thr Gly
            260                 265                 270

His Gln Asn Gly Glu Leu Thr Phe Val Gly Thr Val Thr Ala Ser Ser
        275                 280                 285

Tyr Gly Tyr
    290

<210> SEQ ID NO 17
```

```
<211> LENGTH: 353
<212> TYPE: PRT
<213> ORGANISM: Streptomyces coelicolor

<400> SEQUENCE: 17
```

| | | | | | | | | | | | | | | | |
|---|---|---|---|---|---|---|---|---|---|---|---|---|---|---|---|
|Met|Asn|His|Thr|Asn|Arg|Leu|Leu|Pro|Ala|Pro|His|Asp|Leu|Leu| |
|1| | | |5| | | | |10| | | | |15| |
|Phe|Asp|Gly|Cys|Pro|Pro|Leu|Ser|Phe|Ala|Arg|Pro|Leu|Pro|Pro|Ala|
| | | |20| | | | |25| | | | |30| | |
|Asp|Val|His|Lys|Ala|Ala|Ala|Glu|Val|Leu|Leu|Thr|Asp|Ala|Arg| |
| | | | |35| | | | |40| | | | |45| |
|Pro|Leu|Gly|Glu|Asn|Arg|Phe|Ala|Val|Ala|Ala|Leu|Trp|Pro|Arg|Asn|
| |50| | | | |55| | | | |60| | | | |
|Thr|Phe|Leu|Ala|His|Arg|Ala|Thr|Ser|Ser|Pro|Cys|Asp|Pro|Leu|Leu|
|65| | | | |70| | | | |75| | | | |80|
|Ala|Ala|Glu|Thr|Ile|Arg|Gln|Ser|Ala|Ile|His|Leu|Ser|His|Thr|Phe|
| | | | |85| | | | |90| | | | |95| |
|Cys|Asp|Val|Pro|Ile|Gly|His|His|Phe|Val|Leu|Ser|Gly|Leu|Asp|Leu|
| | | | |100| | | | |105| | | | |110| |
|Asp|Leu|Asp|Leu|Pro|Val|Trp|Asp|Ser|Gly|Pro|Leu|Pro|Val|Val|Leu|
| | | |115| | | | |120| | | | |125| | |
|Asp|Val|Thr|Ser|Thr|Lys|Thr|Thr|Thr|Asn|Pro|Arg|Arg|Met|Ala|Arg|
| |130| | | | |135| | | | |140| | | | |
|Ala|Leu|Asn|Ala|Asp|Val|Tyr|Val|Ala|Gly|Leu|His|Arg|Gly|Arg|Cys|
|145| | | | |150| | | | |155| | | | |160|
|Ala|Ile|Arg|Phe|Glu|Val|Leu|Ala|Pro|Arg|Arg|Tyr|Ala|Met|Ile|Arg|
| | | | |165| | | | |170| | | | |175| |
|Asp|Arg|Ala|Arg|Arg|Ala|Glu|Arg|Pro|Ala|Gln|Gln|Ala|Ala|Ala|Gly|
| | | |180| | | | |185| | | | |190| | |
|Ala|Ala|Thr|Ala|Leu|Pro|Pro|Glu|Thr|Val|Gly|Phe|His|Asp|Asp|Leu|
| | | |195| | | | |200| | | | |205| | |
|His|Val|Leu|Leu|Ala|Thr|Ala|Gln|Gly|Leu|Pro|Asp|Thr|Ala|Trp|Gln|
| |210| | | | |215| | | | |220| | | | |
|Leu|Arg|Leu|Arg|Arg|Asp|His|Pro|Val|Leu|Phe|Asp|His|Glu|Ser|Asp|
|225| | | | |230| | | | |235| | | | |240|
|His|Ile|Ser|Gly|Met|Ala|Leu|Leu|Glu|Ala|Cys|Arg|Gln|Ala|Ala|Thr|
| | | | |245| | | | |250| | | | |255| |
|Ala|Leu|Thr|Pro|Pro|Ala|Pro|Gly|Ala|Phe|Gly|Pro|Arg|Gln|Val|Ala|
| | | |260| | | | |265| | | | |270| | |
|Leu|Thr|Ala|Val|Ala|Ser|Ser|Tyr|Gln|Ala|Phe|Gly|Glu|Leu|Asp|Ser|
| | |275| | | | |280| | | | |285| | | |
|Pro|Val|Thr|Ile|Thr|Thr|Leu|Pro|Ala|Ala|His|Gly|His|Ser|Pro|Asp|
| |290| | | | |295| | | | |300| | | | |
|Ser|Gly|Thr|Arg|Thr|Leu|Gln|Leu|Thr|Ala|Arg|Gln|Gly|Ser|Arg|Thr|
|305| | | | |310| | | | |315| | | | |320|
|Leu|Ile|Thr|Ala|Thr|Val|Thr|Thr|Thr|Thr|Ala|Gly|Thr|Gly|Ser| |
| | | | |325| | | | |330| | | | |335| |
|Pro|Gly|Pro|Thr|Val|Pro|His|His|Gly|Asp|Gln|Thr|Lys|Ala|Val|Ala|
| | | |340| | | | |345| | | | |350| | |
|Ser| | | | | | | | | | | | | | | |

```
<210> SEQ ID NO 18
<211> LENGTH: 9521
<212> TYPE: DNA
<213> ORGANISM: Streptomyces coelicolor
```

```
<400> SEQUENCE: 18
ctcgagacat ggctggcatc gaggtcgacg acaccactgc ggacgagctg cgggccctgg      60
ccgacgcggc cgggctgccg ctggacgcct acctcgcgca ggtcgccgag gagaagcggc     120
gcgagcgcgc gctggccgag ggcgcggaga tcttccgccg ggtcaccggc accccggaga     180
ccgtcgccgc cttcgacgcg gagtacgcg gccccgcgca ggcgcagacc gccccgcggg     240
cggcctgacc tgtgcctgcc gagtactacg tcgactaccg gtggttcctg gagcgccagg     300
ccgagctgct ggacgatctc gcggtcagcg actactccgt cttcgtcggc ctagccgccc     360
ggcacagggt cgacccgccc cgtcacgacc agcatcaccc ggacgccttc tggcgggcgg     420
ccgtgatgct ggaggagtgc gtcgtgctcc ggccctgcc cgcccgcaac gagctgtacg     480
gcttcggcgt ggccgtggcg tacctcggga tgcacgggga gcgggtgaac acgaaaattc     540
gaggcctggc gggacctgat ctccgacatc accgccctgc gtctcgactc cttcgccgtc     600
gccgagcggc tgcgctcgct ccgtctgccg ccggcctgac ctcgctgtcg ctctccccg      660
caggaaacgg actgcctgat ccgtaaccgg acgccacgcg ctctggcgct cttctttgcc     720
ggtgcccgtg agcccggagc cggcatggtc tgcctgggcc ggagctcgtt gtccgccgga     780
tcctggtcgc cgcagtcagt tgtggcaggt tgaaatgtcc tccaactgca gcgcagtaag     840
caggagttcc cacaccttgt cagtcgtggc aggtgagcgt cccggcgccc ctcgttcagc     900
cgcgaacgac aacccatagg caacggtcag cagcaggtgg accaccacgt ccggtggctg     960
cgtggccaag ggtgagtagg gggcttgctg ttgctgggtg tcacgggcgg ccgcggccat    1020
ctcgcggcgg atgcggtcca ggagatccgg cgccccgccc gcgggcatgg tgcagtccgc    1080
tgccagccgc agcgccgcac ggaaccggat gtcgtgcttc atttgacggc ttacggccag    1140
cacgagggca cgcaaggcgg tttcgggcgc gcaggcggtc tcggcgatgg agcggccgat    1200
ggtgttccat gtctctgtcg actggctcac cagttcgtcg gcgagcgcct tcttggatgg    1260
gaagtgcccg tagagagcgc ccttcgtcat gcctgtgcgt acggcgaccg ttgccagatt    1320
ggtgcctgca tagccgtgca gggcgaactc ttcagccgcc gcatccagca cctggtcccg    1380
ggtgcgcatc gcccttgcct gcttcaccaa cgcccgagtc ctctcaaggt cgtgagccaa    1440
cgggcccgga aaacatatccc tcgggaaggt atgttagtgg gggcggtcgg cgcacgtgga    1500
cgatgtccca gtcatcggcg caaaagtgga ggcagcacgg ctaccgcgcg gcaggattca    1560
accgatggcc gacggatcgt cgtggcctag cgggcctgga cgccgtgcgc atgcacagcg    1620
gggtcccgcg tcggcgggca gcaccggcca gttggacccc tgggcgtggc gcaccagcac    1680
gaggtccgtg ccgaccacga ccgggttccc cacggcctgc agcatgccga agtcgctctc    1740
gtggtccccg taggcaaagc agtctgccgg caccacccc ctcttcgcca tcacttcggt    1800
cacgcctca gccttcgctt cgccgatcat cgggcgattc acctcgccgg tgaggacgcc    1860
ctgggcgtcg gcgaactgct cggtgcacag aatccggtcc gcgccgaggt cctgcgccag    1920
gggcgtgagc agtggccggg ccgagcccga gatcagaacg atcgtgtggc cggcccggcg    1980
gtgccgagcg agtgccgcca ggccggccct gacgtagccg tccggccgcg tgcggtaagc    2040
gtggtaccag tcgcggccgg cctcctgcag gcgagccagg gaaacaccgg cgtagcgccg    2100
gtagtagacg cggttcatct ccacccggct cgcccctcgg cgccgcatcg ccgtcagatc    2160
ggcatcagca ctgtgcgtt gcccgctcgc ctgcgcggtg atgtcgtccc gcaagctgtg    2220
cggcgcctgc cgtgcgaagt cgagcatgct cttggcggtg atcagtgtct cgtccacatc    2280
```

```
gaagaaggcg atgggggcgta tggcgggcga ccggttcgcg gctgtgcgac gttcgcgcgg    2340
gggctcgggc atcacgccgt acgtctttct gtgtctggtg cggtcgcggt tctgccgggt    2400
gggccggccg ggccgcccgg ctcggcgggg ccgacgccgg tcgatgggtc cgcacggtcg    2460
aagagagcag gcgtgtatgc gccggctgct gcgtcgatgc tcagggccct gtgcgtggca    2520
gcggtggtga tgtcccgcca gtggcgctgt accgggtcgt cttctgcctg gccacgtgat    2580
cccgaggcgc gcagcagttg gtcgacggct tcggagcaca gttccacagc cgcggcggcg    2640
tcccgctgcc cctcggcgac gaggagcggg gtcactggcg cgtggtcggc ccgctctgcc    2700
gctgcctcca ggagcaggcc tgcggcgcgt atgcgtgctg ctgctctggt cagggtgttg    2760
gacgccgggg gcactgcggt gccctgtcgt tctgtggcgg cgtgtgtcca ggcgtcaaga    2820
gctccgcggg ccgccccgag aaccggaaag gcgaacatca gcgcgcccac catgcgtag    2880
ggcaccgtgt ggcagcgggc cgagccgggc aggggagca gcaggtccga caaggtgcag    2940
gtgcggtggc ggggaaccag cacccccgtcc gcctcgacgg tgttgctgcc ggtcccgcgc    3000
atgccgaggg tgtgccaggt gtcggtgacc gtcagctcgt ccctggggac ggcgaacagc    3060
cggtgccgct cgggaacgtt ccggcccggt gtccagcttg cgagcagcac ccagtcggcg    3120
tggtcgacgc cgctggcgaa tccccagcgc ccggtgagcc gccagccgcc cggctcgagg    3180
ttggcctcgc ccgacggggg catgatggcc gcggcgatac gggcgtcggg cgaggagtgc    3240
cacagttcgc gttgggcctt tcgggcagg tacgaggcca gccgcccatg ggccgcatac    3300
agcgtggcgc accaggcggt ggcggcgcag gtccgggcga gcgtggtcgc cgccgtgagc    3360
agttcgccga aggtcccggc gcggccgccg aagcgccggg ggacgaagtg gcgtggaaag    3420
ccgacgtcgg tgaccgcccg ggccacgtcg tctgtgagtc gtcggtgtgt ctcctggact    3480
ccgtggtccc ggtgcgcgag agccacggcg tgttccaccc cgtcgcggga aaactccctg    3540
agcggcgcgg tcatgaggcc accgccttcg tctggtcgcc gtggtgcggg acggtgggcc    3600
cggggcttcc cgtcccggct gtcgtcgtcg tggtgacggt cgcggtgatg agcgtgcggc    3660
tgccttgccg ggcggtgagt tgcagcgtac gtgtgccgct gtccgggctg tgccgtggg    3720
cggcggggag ggtggtgatg gtgacagggg agtcgagttc gccgaatgcc tggtaggaac    3780
ttgcgacggc cgtgagggcc acctgccgcg ggccgaaggc tccggggcgcg ggtggggtga    3840
gggctgtggc ggcctgacgg caggcctcca gcagtgccat gccggaaatg tggtccgatt    3900
cgtggtcgaa gaggaccgga tggtcccggc gcagccgcag ttgccaggct gtatcgggca    3960
ggccttgcgc ggtggcaagc aggacgtgca ggtcgtcgtg gaagccgacg gttttcgggag    4020
gaagggcggt cgccgcgcct gcggctgcct gctgtgcggg gcgctctgcc cgcctggcgc    4080
gatcgcggat catcgcgtac cgccgggggg cgaggacctc gaagcggatg gcgcagcggc    4140
cgcggtggag tccggccacg tacacgtcgg cgttcaacgc cctggccatc cggcgcgggt    4200
tcgtggtggt cttcgtactc gtgacgtcca ggacgacagg cagcgggccg gagtcccaga    4260
cagggagatc gagatcaaga tcgaggcccg acagcacgaa gtggtggcct atgggcacgt    4320
cacagaaggt gtgtgagagg tggatcgccg actgtcgtat ggtctccgcg gctaggaggg    4380
ggtcgcacgg gctcgatgtc gcgcggtgcg cgaggaaggt gtttcggggc cacagggcgg    4440
cgacggcgaa ccggttctcg cccagcggtc gcgcgtcggt gaggagtact ctgccgcgg    4500
cagccttgtg tacgtcggcc ggcggcaggg ggcgcgcgaa ggagagcgga gggcagccgt    4560
cgaacaggag gtcgtggggg gcgggcagta aaagacggtt tgtatggttc ataggggcgc    4620
tacatctccc ggtgtgtcct cgtacgggac caccggctgg cttgccgcgc tgcaagacag    4680
```

```
ccgggatcgg taagctgacc gagagaaata tacctgcggg aaggtattat gcaatgggtt    4740
tccgtgccga cccgggtcgc accagcatgg cgcccgcagg gcccgcacac acgaaggaag    4800
gcagccatga cgagcgccca acaacccacg cctttcgcgg tccggtccaa cgtgccgcgt    4860
ggacctcacc cgcagcagga gcggtcgatc aagacccggg cccagatcct ggaggcggcg    4920
tcggagatct tcgcgtcgcg cggctaccga ggggcctccg tcaaggacgt tgccgagcgt    4980
gtcggcatga ccaagggcgc ggtgtacttc cacttcccca gcaaggaatc actggccatc    5040
gccgtggtgg aggagcacta cgcgcgctgg cccgcagcga tggaagagat ccgcatccag    5100
ggcttcacac cgctggagac ggtcgaggag atgctccatc gcgcggcgca ggccttccgc    5160
gacgaccccg tgatgcaggc cggtgcccgg ctgcagagtg agcgcgcctt catcgacgcg    5220
gagctgcccc tgccctacgt ggactggacc cacctgctgg aggtgccgtt gcaggacgcc    5280
cgtgaggccg gccagttgcg ggcgggcgtc gatcccgcag cagctgcccg ttccctggtg    5340
gccgccttct tcggcatgca gcacgtctcc gacaatctgc accagcgagc ggacatcatg    5400
gagcggtggc aggagctgcg ggagctgatg ttcttcgctc tccgcgcctg acggggagcg    5460
tccgcaaaac tggtggtgcc actgatagga gaatctccct cttttccctg cgctccagca    5520
ccgattacgt tctctgcatg attgcggaca ccgcgacgac cagcgcgcgg acgggagccc    5580
cggccgcagc gttgcgtctg ttctgttttc atcatgcagg aggccaggga acagcattcc    5640
tcggatggca gaagagactg ggagcgcggg cggaggtgat tcccgtccgg ctgccccgc     5700 ccgaggacgt ctctgcagag acagcggacg ggagcggaat gtcgatgacc ctcgtagtcg    5760
cttccctcga tcacgaactc ggcccaatgc tgcggcggcc cttcctgttc tacgggcaca    5820
gcatgggcgc tctcgtggcc taccacctca cccgcctgcg ccagtcccgc ggccggcccc    5880
tgccggagcg gttgctcatc ggcgcctacc cggcccccca tctgccgcac cggctcgccc    5940
actgcacgca cttgcctgac gaggacctgc tcgcgctgct gccgccgcac cctgccggcc    6000
actctcgcct gctgcgccag gcgcccggcc tggcgacagc gactgcggcg cggctgcgcc    6060
tgcacctcgg cctgtgtgac agcgccgcgc cggcggcacc gaaccccgcg cagcacaccg    6120
gccacggttc cccgcagggg aggagtgaac cgctgaggtg tccggtggat gtgttcaccg    6180
ggatcagcga tccgctggtg acggacgccg aggcagccgc atggcggcac cacacccgcg    6240
caggctgccg tatacaccgc atccccggcg ggcatttctt cacgcgcgag accccggaat    6300
ctagggccgc gttcttcgac cggctgtgca cggtgcttgc agggccgtcg gaatgggcgg    6360
ccggagcatc gggtcccctc cctgtcaccg tcgcttcgta aaagcgtttc ccgcaaccca    6420
ggaggacgtt catgtacccc gagacgctcg gattcggtgc tttcctctcc cccatgcatc    6480
cgctgggcga gaatcccacg ctgcaatttc agcgcgacct tgagctgata gaactcctcg    6540
accggctcga ctacaacgaa ttctgggtcg gcgagcatca ctccatgggc tggaacacca    6600
tcggcagccc ggagctgatg gttgcggctg ccgccgagcg gacccgtcgt atcaccctgg    6660
ccaccggtgt gatgacgctg ccgtaccacc accccgttcat ggtggcgagc cgtgcggtgc    6720
acctcgacca tctgacccgt ggccggttcg tgctcggtgt gggcgcgggc ggcatcccga    6780
ccgacgcccg catgatcggc cgtgagatga gcgaactgcg caccatgttc ggcgaggcac    6840
tggaggcggt cgtcgcgctg gtcaacgcgc aggagcgggt gaccaagaag acctcgtggt    6900
tcacgctgaa ggacgccaag ctccagctgt cccgtaccg tgcatcaggg ctggagatcg     6960
ccgctgccag cgtcgcctcc ggcaacagca tgcggctggc cggccgctac gggatcagca    7020
```

-continued

```
ccgtctcctt cggtgcgccg cggcctggtc atccccgacc cgacatgcgt acccagtggt    7080
cgtatgcgga ggaggctgcg gccgaacagg gcaccacggt ggaccgcagg aactggcgaa    7140
tcaccctgcc ggtatacgtg gcagagacgc gcgagcaggc ccttgccgat gtccgggagg    7200
gttacgaccg ctgggcctac ggatactggg gcgacatccg cggcctcgac gtcagcgtcc    7260
ccggcgtcaa gcgtgcgcag gctctggagg ctgccgtgga cgcgggcagc gccatcgtcg    7320
gctccgtcga ggacgtggtg gccggcgtcg agcggctccg tgaggaggtc ggcggcttcg    7380
ggaccctgct cgtctacgcg caggactggg ccgactggga aagacgaag cggagctatg    7440 acctgctggc ccgctacgtc gccccgcact tcaccggctc cacccggcga ctgtacgagt    7500
cggtgcagtg gtaccaggac aaccgcgacc tgtttccgca gctcatcccg taaaccgtgc    7560
acgccgtgcc tgccggcgcc acgggcagct ccaggcacgg ctcggcatcc ctccctggag    7620
tgacagcgac accccatggc caccgaaccg atacgcatcg gcgtggtcgg cgcctccccg    7680
gaccggggct gggccgccga cgcacacctg ccggccctgc agcacctgcc gcagtacaag    7740
atcaccgcgg tcggcacccg ccgggcggac agtgcgcacc gggccgctcg ccggtacggg    7800
gcgacccacg ctttcaccga cccccgcagc ctcgccgcac atcccgacgt ggaactggtc    7860
gcgatcgtcg tgaaagtgcc ggaccatgcg cggctggtgg aggcggcgct cgcggcgggc    7920
aagcatgtcc tgtgcgagtg gccccttgcc cggaccaccg aggaggccgc ccagctaacg    7980
gcggccgctc acggagccgg tgtggtgaac gccgtcggcc tccaggcgcg gcacaccccg    8040 acgtcgtcc gggcccggga actgatcagg caggggtacg tcggccgggt cacctcggtc     8100
accgtgtaca gcacgcgggg ggtcgcggcc ggggggcggc tgcccgccgc cttcgcctac    8160
accctcgact ccacgaacgg cgccggcacc ttcgaggtcg ccggcgggca cacgctcgac    8220
gcggtgcagt acctgctcgg cagggagatg accggcctgt cggctgcgct gtccgttcag    8280
catccgcgga tcacactcga cgaggacgcc cggcagacgg gggcgaccag ccccgatcat    8340
gtcgcgctgc acgcgacgct ggaaggcggc gccgcgctgg tggtccacat ccacgatgcc    8400
aagaacagcg gcgcgggcac ccgcatcgag atctccggca cgcaagggga gctggccatc    8460
gtatccaccg gaccacgaag cggcagcggg ctgcagatca gcgaactggc cctgctcgga    8520
gcgcagggga cagagccgtc cgggcaggag ctgcccttc ccggctcctg ggcacggcc     8580 gtgccagcgg acggtctcga tgcggcccag cacaccatgc tgtgcagta cgcggctctg    8640 gccgcggaca tccgcgaggg cggcagtcgt gtgcctcgtt tcgccgacgg gatcgagctg    8700
caccggctgc tggacgccgt acggctgtcc tccgcaaccg gctgccggct ggagcgccgt    8760
gcgggcgagc ggtggccggt cagctctccc tggccgcggc gtcgacgatc gcggtgagca    8820
ggccggggaa ggcctgatcg agatcatcgg tgcgaagcgt gttcatcttc gaggtgccga    8880
tgtagtactg cctgatgatc ccggcctggc gcaacacctt gaagtggtga gtgccggtcg    8940
agcgggagac ggtgatgtcg aaggtgccgc aggcgatgtc ctcgggtgcc ttagccagct    9000
gccggacgat gctgcggcgc accggatcga ccagcgcgtc caggacgccc tggagggtga    9060
tggcgtcagc gtccggatgg tcggtgatgc gctctgtcgt gatccgtgcc gccacggctg    9120
tccgcctcct cgtcgcgtgt cgttccacca tggtacgaca gccatcaaat gttgacggcc    9180
atcaaagttt gacagccgtc gtcatatgag cttcagtgag aacgcacggt aattccggcg    9240
cagttgggcg gccgccatcc ccccccggcc ggcctctgcc ggccactcct caggacgcgg    9300
cccatacccg accccacag gagcagaaca gcatgaccac tgtccgaaca ggcggggcgc     9360
agaccgccga agtcccggcg gcggccggc gcgatgtccc cagcggggtg aagatcaccg    9420
```

-continued

| | |
|---|---:|
| ctctggccac gggattcgtc atggcgaccc tggacgtcac cgtggtgaac gtcgccggag | 9480 |
| ccaccatcca ggagagcctg acaccacgc tgacccagct g | 9521 |

<210> SEQ ID NO 19
<211> LENGTH: 9521
<212> TYPE: DNA
<213> ORGANISM: Streptomyces coelicolor

<400> SEQUENCE: 19

| | |
|---|---:|
| cagctgggtc agcgtggtgt ccaggctctc ctggatggtg ctccggcga cgttcaccac | 60 |
| ggtgacgtcc agggtcgcca tgacgaatcc cgtggccaga gcggtgatct tcaccccgct | 120 |
| ggggacatcg cgccgccgc ccgccgggac ttcggcggtc tgcgcccgc ctgttcggac | 180 |
| agtggtcatg ctgttctgct cctgtggggg tcgggtatgg gccgcgtcct gaggagtggc | 240 |
| cggcagaggg cggccggggg gggatggcgg ccgcccaact cgccggaat taccgtgcgt | 300 |
| tctcactgaa gctcatatga cgacggctgt caaactttga tggccgtcaa catttgatgg | 360 |
| ctgtcgtacc atggtggaac gacacgcgac gaggaggcgg acagccgtgg cggcacggat | 420 |
| cacgacagag cgcatcaccg accatccgga cgctgacgcc atcaccctcc agggcgtcct | 480 |
| ggacgcgctg gtcgatccgg tgcgccgcag catcgtccgg cagctggcta aggcacccga | 540 |
| ggacatcgcc tgcggcacct tcgacatcac cgtctcccgc tcgaccggca ctcaccactt | 600 |
| caaggtgttg cgccaggccg ggatcatcag gcagtactac atcggcacct cgaagatgaa | 660 |
| cacgcttcgc accgatgatc tcgatcaggc cttccccggc ctgctcaccg cgatcgtcga | 720 |
| cgccgcggcc agggagagct gaccggccac cgctcgcccg cacggcgctc cagccggcag | 780 |
| ccggttgcgg aggacagccg tacggcgtcc agcagccggt gcagctcgat cccgtcggcg | 840 |
| aaacgaggca cacgactgcc gccctcgcgg atgtccgcgg ccagagccgc gtactgcaca | 900 |
| gccatggtgt gctgggccgc atcgagaccg tccgctggca cggccgtgcc ccaggagccg | 960 |
| ggaaagggca gctcctgccc ggacggctct gtccctgcg ctccgagcag ggccagttcg | 1020 |
| ctgatctgca gcccgctgcc gcttcgtggt ccggtggata cgatggccag ctcccccttgc | 1080 |
| gtgccggaga tctcgatgcg ggtgcccgcg ccgctgttct tggcatcgtg gatgtggacc | 1140 |
| accagcgcgg cgccgccttc cagcgtcgcg tgcagcgcga catgatcggg gctggtcgcc | 1200 |
| cccgtctgcc gggcgtcctc gtcgagtgtg atccgcggat gctgaacgga cagcgcagcc | 1260 |
| gacaggccgg tcatctccct gccgagcagg tactgcaccg cgtcgagcgt gtgcccgccg | 1320 |
| gcgacctcga aggtgccggc gccgttcgtg gagtcgaggg tgtaggcgaa ggcggcgggc | 1380 |
| agccgccccc cggccgcgac ccccgcgtg ctgtacacgg tgaccgaggt gacccggccg | 1440 |
| acgtacccct gcctgatcag ttcccgggcc cggacgaccg tcggggtgtg ccgcgcctgg | 1500 |
| aggccgacgg cgttcaccac accggctccg tgagcggccg ccgttagctg ggcggcctcc | 1560 |
| tcggtggtcc gggcaagggg ccactcgcac aggacatgct tgcccgccgc gagcgccgcc | 1620 |
| tccaccagcc gcgcatggtc cggcactttc acgacgatcg cgaccagttc cacgtcggga | 1680 |
| tgtgcggcga ggctgcgggg gtcggtgaaa gcgtgggtcg ccccgtaccg gcgagcggcc | 1740 |
| cggtgcgcac tgtccgcccg gcgggtgccg accgcggtga tcttgtactg cggcaggtgc | 1800 |
| tgcagggccg gcaggtgtgc gtcggcggcc cagcccggt ccggggaggc gccgaccacg | 1860 |
| ccgatgcgta tcggttcggt ggccatgggg tgtcgctgtc actccaggga gggatgccga | 1920 |
| gccgtgcctg gagctgcccg tggcgccggc aggcacggcg tgcacggttt acgggatgag | 1980 |

```
ctgcggaaac aggtcgcggt tgtcctggta ccactgcacc gactcgtaca gtcgccgggt    2040
ggagccggtg aagtgcgggg cgacgtagcg ggccagcagg tcatagctcc gcttcgtctt    2100
ctcccagtcg gcccagtcct gcgcgtagac gagcagggtc ccgaagccgc cgacctcctc    2160
acggagccgc tcgacgccgg ccaccacgtc ctcgacggag ccgacgatgg cgctgcccgc    2220
gtccacggca gcctccagag cctgcgcacg cttgacgccg gggacgctga cgtcgaggcc    2280
gcggatgtcg ccccagtatc cgtaggccca gcggtcgtaa ccctcccgga catcggcaag    2340
ggcctgctcg cgcgtctctg ccacgtatac cggcagggtg attcgccagt tcctgcggtc    2400
caccgtggtg ccctgttcgg ccgcagcctc ctccgcatac gaccactggg tacgcatgtc    2460
gggtcgggga tgaccaggcc gcggcgcacc gaaggagacg tgctgatcc cgtagcggcc    2520 ggccagccga atgctgttgc cggaggcgac gctggcagcg gcgatctcca gcccgatgc    2580 acggtacggg gacagctgga gcttggcgtc cttcagcgtg aaccacgagg tcttcttggt    2640
cacccgctcc tcgccgttga ccagcgcgac gaccgcctcc agtgcctcgc cgaacatggt    2700
gcgcagttcg ctcatctcac ggccgatcat gcgggcgtcg gtcgggatgc cgcccgcgcc    2760
cacaccgagc acgaaccggc cacgggtcag atggtcgagg tgcaccgcac ggctcgccac    2820
catgaacggg tggtggtacg gcagcgtcat cacaccggtg gccagggtga tacgacgggt    2880
ccgctcggcg gcagccgcaa ccatcagctc cgggctgccg atggtgttcc agcccatgga    2940
gtgatgctcg ccgacccaga attcgttgta gtcgagccgg tcgaggagtt ctatcagctc    3000
aaggtcgcgc tgaaattgca gcgtgggatt ctcgcccagc ggatgcatgg gggagaggaa    3060
agcaccgaat ccgagcgtct cggggtacat gaacgtcctc ctgggttgcg ggaaacgctt    3120
ttacgaagcg acggtgacag ggaggggacc cgatgctccg gccgcccatt ccgacggccc    3180
tgcaagcacc gtgcacagcc ggtcgaagaa cgcggcccta gattccgggg tctcgcgcgt    3240
gaagaaatgc ccgccgggga tgcggtgtat acggcagcct gcgcgggtgt ggtgccgcca    3300
tgcggctgcc tcggcgtccg tcaccagcgg atcgctgatc ccggtgaaca catccaccgg    3360
acacctcagc ggttcactcc tccctgcgg ggaaccgtgg ccggtgtgct gcgcggggtt    3420
cggtgccgcc ggcgcggcgc tgtcacacag gccgaggtgc aggcgcagcc gcgccgcagt    3480
cgctgtcgcc aggccgggcg cctggcgcag caggcgagag tggccggcag ggtgcggcgg    3540
cagcagcgcg agcaggtcct cgtcaggcaa gtgcgtgcag tgggcgagcc ggtgcggcag    3600 atgggggggcc gggtaggcgc cgatgagcaa ccgctccggc aggggccggc cgcgggactg    3660
gcgcaggcgg gtgaggtggt aggccacgag agcgcccatg ctgtgcccgt agaacaggaa    3720
gggccgccgc agcattgggc cgagttcgtg atcgagggaa gcgactacga gggtcatcga    3780
cattccgctc ccgtccgctg tctctgcaga gacgtcctcg gcgggggca gccggacggg    3840 aatcacctcc gcccgcgctc ccagtctctt ctgccatccg aggaatgctg ttccctggcc    3900
tcctgcatga tgaaaacaga acagacgcaa cgctgcggcc ggggctcccg tccgcgcgct    3960
ggtcgtcgcg gtgtccgcaa tcatgcagag aacgtaatcg gtgctggagc gcagggaaaa    4020
gagggagatt ctcctatcag tggcaccacc agttttgcgg acgctccccg tcaggcgcgg    4080
agagcgaaga acatcagctc ccgcagctcc tgccaccgct ccatgatgtc cgctcgctgg    4140
tgcagattgt cggagacgtg ctgcatgccg aagaaggcgg ccaccaggga acgggcagct    4200
gctgcgggat cgacgcccgc ccgcaactgg ccggcctcac gggcgtcctg caacggcacc    4260
tccagcaggt gggtccagtc cacgtagggc aggggcagct ccgcgtcgat gaaggcgcgc    4320
tcactctgca gccgggcacc ggcctgcatc acggggtcgt cgcggaaggc ctgcgccgcg    4380
```

```
cgatggagca tctcctcgac cgtctccagc ggtgtgaagc cctggatgcg gatctcttcc    4440
atcgctgcgg gccagcgcgc gtagtgctcc tccaccacgg cgatggccag tgattccttg    4500
ctggggaagt ggaagtacac cgcgcccttg gtcatgccga cacgctcggc aacgtccttg    4560
acggaggccc ctcggtagcc gcgcgacgcg aagatctccg acgccgcctc caggatctgg    4620
gcccgggtct tgatcgaccg ctcctgctgc gggtgaggtc cacgcggcac gttggaccgg    4680
accgcgaaag gcgtggggttg ttgggcgctc gtcatggctg ccttccttcg tgtgtgcggg    4740
ccctgcgggc gccatgctgg tgcgacccgg gtcggcacgg aaacccattg cataatacct    4800
tcccgcaggt atatttctct cggtcagctt accgatcccg gctgtcttgc agcgcggcaa    4860
gccagccggt ggtcccgtac gaggacacac cgggagatgt agcgcccccta tgaaccatac    4920 aaaccgtctt ttactgcccg ccccccacga cctcctgttc gacggctgcc ctccgctctc    4980
cttcgcgcgc ccctgccgc cggccgacgt acacaaggct gccgcggcag aagtactcct    5040
caccgacgcg cgaccgctgg gcgagaaccg gttcgccgtc gccgccctgt ggccccgaaa    5100
caccttcctc gcgcaccgcg cgacatcgag cccgtgcgac ccctcctag ccgcggagac    5160 catacgacag tcggcgatcc acctctcaca caccttctgt gacgtgccca taggccacca    5220
cttcgtgctg tcgggcctcg atcttgatct cgatctccct gtctgggact ccggcccgct    5280
gcctgtcgtc ctggacgtca cgagtacgaa gaccaccacg aacccgcgcc ggatggccag    5340
ggcgttgaac gccgacgtgt acgtggccgg actccaccgc ggccgctgcg ccatccgctt    5400
cgaggtcctc gccccccggc ggtacgcgat gatccgcgat cgcgccaggc gggcagagcg    5460
ccccgcacag caggcagccg caggcgcggc gaccgccctt cctcccgaaa ccgtcggctt    5520
ccacgacgac ctgcacgtcc tgcttgccac cgcgcaaggc ctgcccgata cagcctggca    5580
actgcggctg cgccgggacc atccggtcct cttcgaccac gaatcggacc acatttccgg    5640
catggcactg ctggaggcct gccgtcaggc cgccacagcc ctcaccccac ccgcgcccgg    5700
agccttcggc ccgcggcagg tggccctcac ggccgtcgca agttcctacc aggcattcgg    5760
cgaactcgac tccctgtca ccatcaccac cctccccgcc gcccacgggc acagcccgga    5820
cagcggcaca cgtacgctgc aactcaccgc ccggcaaggc agccgcacgc tcatcaccgc    5880
gaccgtcacc acgacgacga cagccgggac gggaagcccc gggcccaccg tcccgcacca    5940
cggcgaccag acgaaggcgg tggcctcatg accgcgccgc tcagggagtt ttcccgcgac    6000
ggggtggaac acgccgtggc tctcgcgcac cgggaccacg gagtccagga cacacccga    6060 cgactcacag acgacgtggc ccgggcggtc accgacgtcg gctttccacg ccacttcgtc    6120
ccccggcgct tcgcggccg cgccgggacc ttcggcgaac tgctcacggc ggcgaccacg    6180
ctcgcccgga cctgcgccgc caccgcctgg tgcgccacgc tgtatgcggc ccatgggcgg    6240
ctggcctcgt acctgcccga aaaggcccaa cgcgaactgt ggcactcctc gcccgacgcc    6300
cgtatcgccg cggccatcat gccccgtcg ggcgaggcca acctcgagcc gggcggctgg    6360
cggctcaccg ggcgctgggg attgccagc ggcgtcgacc acgccgactg ggtgctgctc    6420
gcaagctgga caccgggccg gaacgttccc gagcggcacc ggctgttcgc cgtccccagg    6480
gacgagctga cggtcaccga cacctggcac accctcggca tgcgcgggac cggcagcaac    6540
accgtcgagg cggacggggt gctggttccc cgccaccgca cctgcacctt gtcggacctg    6600 ctgctcccc tgcccggctc ggcccgctgc cacacggtgc cctacgccat ggtgggcgcg    6660
ctgatgttcg cctttccggt tctcggggcg gcccgcggag ctcttgacgc ctggacacac    6720
```

```
gccgccacag aacgacaggg caccgcagtg cccccggcgt ccaacaccct gaccagagca   6780
gcagcacgca tacgcgccgc aggcctgctc ctggaggcag cggcagagcg ggccgaccac   6840
gcgccagtga ccccgctcct cgtcgccgag gggcagcggg acgccgccgc ggctgtggaa   6900
ctgtgctccg aagccgtcga ccaactgctg cgcgcctcgg gatcacgtgg ccaggcagaa   6960
gacgacccgg tacagcgcca ctggcgggac atcaccaccg ctgccacgca cagggccctg   7020
agcatcgacg cagcagccgg cgcatacacg cctgctctct tcgaccgtgc ggacccatcg   7080
accggcgtcg gccccgccga gccgggcggc ccggccggcc cacccggcag aaccgcgacc   7140
gcaccagaca cagaaagacg tacggcgtga tgcccgagcc cccgcgcgaa cgtcgcacag   7200
ccgcgaaccg gtcgcccgcc atacgcccca tcgccttctt cgatgtggac gagacactga   7260
tcaccgccaa gagcatgctc gacttcgcac ggcaggcgcc gcacagcttg cgggacgaca   7320
tcaccgcgca ggcgagcggg caacgccaca gtgctgatgc cgatctgacg gcgatgcggc   7380
gccgaggggc gagccgggtg gagatgaacc gcgtctacta ccggcgctac gccggtgttt   7440
ccctggctcg cctgcaggag gccggccgcg actggtacca cgcttaccgc acgcggccgg   7500
acggctacgt cagggccggc ctgcggcac tcgctcggca ccgccgggcc ggccacacga   7560
tcgttctgat ctcgggctcg gcccggccac tgctcacgcc cctggcgcag gacctcggcg   7620
cggaccggat tctgtgcacc gagcagttcg ccgacgccca gggcgtcctc accggcgagg   7680
tgaatcgccc gatgatcggc gaagcgaagg ctgaggccgt gaccgaagtg atggcgaaga   7740
ggggggtggt gccggcagac tgctttgcct acggggacca cgagagcgac ttcggcatgc   7800
tgcaggccgt ggggaacccg gtcgtggtcg gcacggacct cgtgctggtg cgccacgccc   7860
aggggtccaa ctgccggtg ctgcccgccg acgcgggacc ccgctgtgca tgcgcacggc   7920
gtccaggccc gctaggccac gacgatccgt cggccatcgg ttgaatcctg ccgcgcggta   7980
gccgtgctgc ctccactttt cgccgatga ctgggacatc gtccacgtgc gccgaccgcc   8040
cccactaaca taccttcccg agggtatgtt ttccgggccc gttggctcac gaccttgaga   8100
ggactcgggc gttggtgaag caggcaaggg cgatgcgcac ccgggaccag gtgctggatg   8160
cggcggctga agagttcgcc ctgcacggct atgcaggcac caatctggca acggtcgccg   8220
tacgcacagg catgacgaag ggcgctctct acgggcactt cccatccaag aaggcgctcg   8280
ccgacgaact ggtgagccag tcgacagaga catggaacac catcggccgc tccatcgccg   8340
agaccgcctg cgcgcccgaa accgccttgc gtgccctcgt gctggccgta agccgtcaaa   8400
tgaagcacga catccggttc cgtgcggcgc tgcggctggc agcggactgc accatgcccg   8460
cgggcggggc gccggatctc ctggaccgca tccgccgcga gatggccgcg ccgcccgtg   8520
acacccagca acagcaagcc ccctactcac ccttggccac gcagccaccg gacgtggtgg   8580
tccacctgct gctgaccgtt gcctatgggt tgtcgttcgc ggctgaacga ggggcgccgg   8640
gacgctcacc tgccacgact gacaaggtgt gggaactcct gcttactgcg ctgcagttgg   8700
aggacatttc aacctgccac aactgactgc ggcgaccagg atccggcgga caacgagctc   8760
cggcccaggc agaccatgcc ggctccggc tcacgggcac cggcaaagaa gagcgccaga   8820
gcgcgtggcg tccggttacg gatcaggcag tccgtttcct gcgggggaga gcgacagcga   8880
ggtcaggccg gcggcagacg gagcgagcgc agccgctcgg cgacggcgaa ggagtcgaga   8940
cgcagggcgg tgatgtcgga gatcaggtcc cgccaggcct cgaattttcg tgttcacccg   9000
ctccccgtgc atcccgaggt acgccacggc cacgccgaag ccgtacagct cgttgcgggc   9060
gggcaggggc cggagcacga cgcactcctc cagcatcacg gccgcccgcc agaaggcgtc   9120
```

```
cgggtgatgc tggtcgtgac ggggcgggtc gaccctgtgc cgggcggcta ggccgacgaa    9180
gacggagtag tcgctgaccg cgagatcgtc cagcagctcg gcctggcgct ccaggaacca    9240
ccggtagtcg acgtagtact cggcaggcac aggtcaggcc gcccgcgggg cggtctgcgc    9300
ctgcgcgggg ccgccgtact ccgcgtcgaa ggcggcgacg tctccgggg tgccggtgac     9360 ccggcggaag atctccgcgc cctcggccag cgccgcgctcg cgccgcttct cctcggcgac    9420
ctgcgcgagg taggcgtcca gcggcagccc ggccgcgtcg gccagggccc gcagctcgtc    9480
cgcagtggtg tcgtcgacct cgatgccagc catgtctcga g                        9521
```

<210> SEQ ID NO 20
<211> LENGTH: 265
<212> TYPE: PRT
<213> ORGANISM: Streptomyces coelicolor

<400> SEQUENCE: 20

```
Val Met Pro Glu Pro Pro Arg Glu Arg Arg Thr Ala Ala Asn Arg Ser
1               5                   10                  15

Pro Ala Ile Arg Pro Ile Ala Phe Phe Asp Val Asp Glu Thr Leu Ile
            20                  25                  30

Thr Ala Lys Ser Met Leu Asp Phe Ala Arg Gln Ala Pro His Ser Leu
        35                  40                  45

Arg Asp Asp Ile Thr Ala Gln Ala Ser Gly Gln Arg His Ser Ala Asp
    50                  55                  60

Ala Asp Leu Thr Ala Met Arg Arg Gly Ala Ser Arg Val Glu Met
65                  70                  75                  80

Asn Arg Val Tyr Tyr Arg Arg Tyr Ala Gly Val Ser Leu Ala Arg Leu
                85                  90                  95

Gln Glu Ala Gly Arg Asp Trp Tyr His Ala Tyr Arg Thr Arg Pro Asp
            100                 105                 110

Gly Tyr Val Arg Ala Gly Leu Ala Ala Leu Ala Arg His Arg Arg Ala
        115                 120                 125

Gly His Thr Ile Val Leu Ile Ser Gly Ser Ala Arg Pro Leu Leu Thr
    130                 135                 140

Pro Leu Ala Gln Asp Leu Gly Ala Asp Arg Ile Leu Cys Thr Glu Gln
145                 150                 155                 160

Phe Ala Asp Ala Gln Gly Val Leu Thr Gly Glu Val Asn Arg Pro Met
                165                 170                 175

Ile Gly Glu Ala Lys Ala Glu Ala Val Thr Glu Val Met Ala Lys Arg
            180                 185                 190

Gly Val Val Pro Ala Asp Cys Phe Ala Tyr Gly Asp His Glu Ser Asp
        195                 200                 205

Phe Gly Met Leu Gln Ala Val Gly Asn Pro Val Val Gly Thr Asp
    210                 215                 220

Leu Val Leu Val Arg His Ala Gln Gly Ser Asn Trp Pro Val Leu Pro
225                 230                 235                 240

Ala Asp Ala Gly Pro Arg Cys Ala Cys Ala Arg Arg Pro Gly Pro Leu
                245                 250                 255

Gly His Asp Asp Pro Ser Ala Ile Gly
            260                 265
```

<210> SEQ ID NO 21
<211> LENGTH: 400
<212> TYPE: PRT
<213> ORGANISM: Streptomyces coelicolor

<400> SEQUENCE: 21

```
Met Thr Ala Pro Leu Arg Glu Phe Ser Arg Asp Gly Val Glu His Ala
1               5                   10                  15
Val Ala Leu Ala His Arg Asp His Gly Val Gln Glu Thr His Arg Arg
            20                  25                  30
Leu Thr Asp Asp Val Ala Arg Ala Val Thr Asp Val Gly Phe Pro Arg
        35                  40                  45
His Phe Val Pro Arg Arg Phe Gly Gly Arg Ala Gly Thr Phe Gly Glu
    50                  55                  60
Leu Leu Thr Ala Ala Thr Thr Leu Ala Arg Thr Cys Ala Ala Thr Ala
65                  70                  75                  80
Trp Cys Ala Thr Leu Tyr Ala Ala His Gly Arg Leu Ala Ser Tyr Leu
                85                  90                  95
Pro Glu Lys Ala Gln Arg Glu Leu Trp His Ser Ser Pro Asp Ala Arg
            100                 105                 110
Ile Ala Ala Ile Met Pro Pro Ser Gly Glu Ala Asn Leu Glu Pro
        115                 120                 125
Gly Gly Trp Arg Leu Thr Gly Arg Trp Gly Phe Ala Ser Gly Val Asp
    130                 135                 140
His Ala Asp Trp Val Leu Leu Ala Ser Trp Thr Pro Gly Arg Asn Val
145                 150                 155                 160
Pro Glu Arg His Arg Leu Phe Ala Val Pro Arg Asp Glu Leu Thr Val
                165                 170                 175
Thr Asp Thr Trp His Thr Leu Gly Met Arg Gly Thr Gly Ser Asn Thr
            180                 185                 190
Val Glu Ala Asp Gly Val Leu Val Pro Arg His Arg Thr Cys Thr Leu
        195                 200                 205
Ser Asp Leu Leu Leu Pro Leu Pro Gly Ser Ala Arg Cys His Thr Val
    210                 215                 220
Pro Tyr Ala Met Val Gly Ala Leu Met Phe Ala Phe Pro Val Leu Gly
225                 230                 235                 240
Ala Ala Arg Gly Ala Leu Asp Ala Trp Thr His Ala Ala Thr Glu Arg
                245                 250                 255
Gln Gly Thr Ala Val Pro Pro Ala Ser Asn Thr Leu Thr Arg Ala Ala
            260                 265                 270
Ala Arg Ile Arg Ala Ala Gly Leu Leu Leu Glu Ala Ala Glu Arg
        275                 280                 285
Ala Asp His Ala Pro Val Thr Pro Leu Leu Val Ala Glu Gly Gln Arg
    290                 295                 300
Asp Ala Ala Ala Val Glu Leu Cys Ser Glu Ala Val Asp Gln Leu
305                 310                 315                 320
Leu Arg Ala Ser Gly Ser Arg Gly Gln Ala Glu Asp Pro Val Gln
                325                 330                 335
Arg His Trp Arg Asp Ile Thr Thr Ala Ala Thr His Arg Ala Leu Ser
            340                 345                 350
Ile Asp Ala Ala Ala Gly Ala Tyr Thr Pro Ala Leu Phe Asp Arg Ala
        355                 360                 365
Asp Pro Ser Thr Gly Val Gly Pro Ala Glu Pro Gly Gly Pro Ala Gly
    370                 375                 380
Pro Pro Gly Arg Thr Ala Thr Ala Pro Asp Thr Glu Arg Arg Thr Ala
385                 390                 395                 400
```

```
<210> SEQ ID NO 22
<211> LENGTH: 241
<212> TYPE: PRT
<213> ORGANISM: Streptomyces coelicolor

<400> SEQUENCE: 22

Val Ile Pro Val Arg Leu Pro Pro Glu Asp Val Ser Ala Glu Thr
1               5                   10                  15

Ala Asp Gly Ser Gly Met Ser Met Thr Leu Val Val Ala Ser Leu Asp
                20                  25                  30

His Glu Leu Gly Pro Met Leu Arg Arg Pro Phe Leu Phe Tyr Gly His
            35                  40                  45

Ser Met Gly Ala Leu Val Ala Tyr His Leu Thr Arg Leu Arg Gln Ser
    50                  55                  60

Arg Gly Arg Pro Leu Pro Glu Arg Leu Leu Ile Gly Ala Tyr Pro Ala
65                  70                  75                  80

Pro His Leu Pro His Arg Leu Ala His Cys Thr His Leu Pro Asp Glu
                85                  90                  95

Asp Leu Leu Ala Leu Leu Pro Pro His Pro Ala Gly His Ser Arg Leu
                100                 105                 110

Leu Arg Gln Ala Pro Gly Leu Ala Thr Ala Thr Ala Ala Arg Leu Arg
            115                 120                 125

Leu His Leu Gly Leu Cys Asp Ser Ala Ala Pro Ala Ala Pro Asn Pro
    130                 135                 140

Ala Gln His Thr Gly His Gly Ser Pro Gln Gly Arg Ser Glu Pro Leu
145                 150                 155                 160

Arg Cys Pro Val Asp Val Phe Thr Gly Ile Ser Asp Pro Leu Val Thr
                165                 170                 175

Asp Ala Glu Ala Ala Ala Trp Arg His His Thr Arg Ala Gly Cys Arg
                180                 185                 190

Ile His Arg Ile Pro Gly Gly His Phe Phe Thr Arg Glu Thr Pro Glu
            195                 200                 205

Ser Arg Ala Ala Phe Phe Asp Arg Leu Cys Thr Val Leu Ala Gly Pro
    210                 215                 220

Ser Glu Trp Ala Ala Gly Ala Ser Gly Pro Leu Pro Val Thr Val Ala
225                 230                 235                 240

Ser

<210> SEQ ID NO 23
<211> LENGTH: 373
<212> TYPE: PRT
<213> ORGANISM: Streptomyces coelicolor

<400> SEQUENCE: 23

Met Tyr Pro Glu Thr Leu Gly Phe Gly Ala Phe Leu Ser Pro Met His
1               5                   10                  15

Pro Leu Gly Glu Asn Pro Thr Leu Gln Phe Gln Arg Asp Leu Glu Leu
                20                  25                  30

Ile Glu Leu Leu Asp Arg Leu Asp Tyr Asn Glu Phe Trp Val Gly Glu
            35                  40                  45

His His Ser Met Gly Trp Asn Thr Ile Gly Ser Pro Glu Leu Met Val
    50                  55                  60

Ala Ala Ala Ala Glu Arg Thr Arg Arg Ile Thr Leu Ala Thr Gly Val
65                  70                  75                  80

Met Thr Leu Pro Tyr His His Pro Phe Met Val Ala Ser Arg Ala Val
                85                  90                  95
```

```
His Leu Asp His Leu Thr Arg Gly Arg Phe Val Leu Val Gly Ala
            100                 105                 110

Gly Gly Ile Pro Thr Asp Ala Arg Met Ile Gly Arg Glu Met Ser Glu
        115                 120                 125

Leu Arg Thr Met Phe Gly Glu Ala Leu Glu Ala Val Val Ala Leu Val
        130                 135                 140

Asn Gly Glu Glu Arg Val Thr Lys Lys Thr Ser Trp Phe Thr Leu Lys
145                 150                 155                 160

Asp Ala Lys Leu Gln Leu Ser Pro Tyr Arg Ala Ser Gly Leu Glu Ile
                165                 170                 175

Ala Ala Ala Ser Val Ala Ser Gly Asn Ser Met Arg Leu Ala Gly Arg
            180                 185                 190

Tyr Gly Ile Ser Thr Val Ser Phe Gly Ala Pro Arg Pro Gly His Pro
        195                 200                 205

Arg Pro Asp Met Arg Thr Gln Trp Ser Tyr Ala Glu Glu Ala Ala Ala
    210                 215                 220

Glu Gln Gly Thr Thr Val Asp Arg Arg Asn Trp Arg Ile Thr Leu Pro
225                 230                 235                 240

Val Tyr Val Ala Glu Thr Arg Glu Gln Ala Leu Ala Asp Val Arg Glu
                245                 250                 255

Gly Tyr Asp Arg Trp Ala Tyr Gly Tyr Trp Gly Asp Ile Arg Gly Leu
            260                 265                 270

Asp Val Ser Val Pro Gly Val Lys Arg Ala Gln Ala Leu Glu Ala Ala
        275                 280                 285

Val Asp Ala Gly Ser Ala Ile Val Gly Ser Val Glu Asp Val Val Ala
    290                 295                 300

Gly Val Glu Arg Leu Arg Glu Glu Val Gly Gly Phe Gly Thr Leu Leu
305                 310                 315                 320

Val Tyr Ala Gln Asp Trp Ala Asp Trp Glu Lys Thr Lys Arg Ser Tyr
                325                 330                 335

Asp Leu Leu Ala Arg Tyr Val Ala Pro His Phe Thr Gly Ser Thr Arg
            340                 345                 350

Arg Leu Tyr Glu Ser Val Gln Trp Tyr Gln Asp Asn Arg Asp Leu Phe
        355                 360                 365

Pro Gln Leu Ile Pro
    370

<210> SEQ ID NO 24
<211> LENGTH: 393
<212> TYPE: PRT
<213> ORGANISM: Streptomyces coelicolor

<400> SEQUENCE: 24

Met Ala Thr Glu Pro Ile Arg Ile Gly Val Val Gly Ala Ser Pro Asp
1               5                   10                  15

Arg Gly Trp Ala Ala Asp Ala His Leu Pro Ala Leu Gln His Leu Pro
            20                  25                  30

Gln Tyr Lys Ile Thr Ala Val Gly Thr Arg Arg Ala Asp Ser Ala His
        35                  40                  45

Arg Ala Ala Arg Arg Tyr Gly Ala Thr His Ala Phe Thr Asp Pro Arg
    50                  55                  60

Ser Leu Ala Ala His Pro Asp Val Glu Leu Val Ala Ile Val Val Lys
65                  70                  75                  80

Val Pro Asp His Ala Arg Leu Val Glu Ala Ala Leu Ala Ala Gly Lys
```

```
                85                  90                  95
His Val Leu Cys Glu Trp Pro Leu Ala Arg Thr Thr Glu Glu Ala Ala
            100                 105                 110

Gln Leu Thr Ala Ala Ala His Gly Ala Gly Val Val Asn Ala Val Gly
            115                 120                 125

Leu Gln Ala Arg His Thr Pro Thr Val Val Arg Ala Arg Glu Leu Ile
    130                 135                 140

Arg Gln Gly Tyr Val Gly Arg Val Thr Ser Val Thr Val Tyr Ser Thr
145                 150                 155                 160

Arg Gly Val Ala Ala Gly Gly Arg Leu Pro Ala Ala Phe Ala Tyr Thr
                165                 170                 175

Leu Asp Ser Thr Asn Gly Ala Gly Thr Phe Glu Val Ala Gly Gly His
            180                 185                 190

Thr Leu Asp Ala Val Gln Tyr Leu Leu Gly Arg Glu Met Thr Gly Leu
        195                 200                 205

Ser Ala Ala Leu Ser Val Gln His Pro Arg Ile Thr Leu Asp Glu Asp
    210                 215                 220

Ala Arg Gln Thr Gly Ala Thr Ser Pro Asp His Val Ala Leu His Ala
225                 230                 235                 240

Thr Leu Glu Gly Gly Ala Ala Leu Val Val His Ile His Asp Ala Lys
                245                 250                 255

Asn Ser Gly Ala Gly Thr Arg Ile Glu Ile Ser Gly Thr Gln Gly Glu
            260                 265                 270

Leu Ala Ile Val Ser Thr Gly Pro Arg Ser Gly Ser Gly Leu Gln Ile
        275                 280                 285

Ser Glu Leu Ala Leu Leu Gly Ala Gln Gly Thr Glu Pro Ser Gly Gln
    290                 295                 300

Glu Leu Pro Phe Pro Gly Ser Trp Gly Thr Ala Val Pro Ala Asp Gly
305                 310                 315                 320

Leu Asp Ala Ala Gln His Thr Met Ala Val Gln Tyr Ala Ala Leu Ala
                325                 330                 335

Ala Asp Ile Arg Glu Gly Gly Ser Arg Val Pro Arg Phe Ala Asp Gly
            340                 345                 350

Ile Glu Leu His Arg Leu Leu Asp Ala Val Arg Leu Ser Ser Ala Thr
        355                 360                 365

Gly Cys Arg Leu Glu Arg Arg Ala Gly Glu Arg Trp Pro Val Ser Ser
    370                 375                 380

Pro Trp Pro Arg Arg Arg Ser Arg
385                 390

<210> SEQ ID NO 25
<211> LENGTH: 38
<212> TYPE: DNA
<213> ORGANISM: Artificial
<220> FEATURE:
<223> OTHER INFORMATION: Primer

<400> SEQUENCE: 25
tttttctaga tgattaggag gaccgtgcgc ggcgcgat                        38

<210> SEQ ID NO 26
<211> LENGTH: 39
<212> TYPE: DNA
<213> ORGANISM: Artificial
<220> FEATURE:
<223> OTHER INFORMATION: Primer
```

-continued

```
<400> SEQUENCE: 26
ttttaagctt atcgcggtca tggacgacgt ggtacgtgt                    39

<210> SEQ ID NO 27
<211> LENGTH: 20
<212> TYPE: DNA
<213> ORGANISM: Artificial
<220> FEATURE:
<223> OTHER INFORMATION: Oligonucleotide linker

<400> SEQUENCE: 27
catggaggaa gcttatgatc                                          20

<210> SEQ ID NO 28
<211> LENGTH: 20
<212> TYPE: DNA
<213> ORGANISM: Artificial
<220> FEATURE:
<223> OTHER INFORMATION: Oligonucleotide linker

<400> SEQUENCE: 28
gatcataagc ttcctccatg                                          20

<210> SEQ ID NO 29
<211> LENGTH: 37
<212> TYPE: DNA
<213> ORGANISM: Artificial
<220> FEATURE:
<223> OTHER INFORMATION: Primer

<400> SEQUENCE: 29
tataagcttg gtgaactcct tcggcgagtg gttcgga                       37

<210> SEQ ID NO 30
<211> LENGTH: 36
<212> TYPE: DNA
<213> ORGANISM: Artificial
<220> FEATURE:
<223> OTHER INFORMATION: Primer

<400> SEQUENCE: 30
tatggtaccg gggagaactc cttgggatac ttcctg                        36

<210> SEQ ID NO 31
<211> LENGTH: 36
<212> TYPE: DNA
<213> ORGANISM: Artificial
<220> FEATURE:
<223> OTHER INFORMATION: Oligonucleotide primer

<400> SEQUENCE: 31
attactagtt cgccgagcgg ctgcgctcgc tccgtc                        36

<210> SEQ ID NO 32
<211> LENGTH: 27
<212> TYPE: DNA
<213> ORGANISM: Artificial
<220> FEATURE:
<223> OTHER INFORMATION: Oligonucleotide primer

<400> SEQUENCE: 32
ccgccgacgc gggaccccgc tgtgcat                                  27

<210> SEQ ID NO 33
<211> LENGTH: 33
```

```
<212> TYPE: DNA
<213> ORGANISM: Artificial
<220> FEATURE:
<223> OTHER INFORMATION: Oligonucleotide primer

<400> SEQUENCE: 33
aatcactggc catcgccgtg gtggaggagc act                          33

<210> SEQ ID NO 34
<211> LENGTH: 36
<212> TYPE: DNA
<213> ORGANISM: Artificial
<220> FEATURE:
<223> OTHER INFORMATION: Oligonucleotide primer

<400> SEQUENCE: 34
tttcatatgc gcccgcgctc ccagtctctt ctgcca                       36

<210> SEQ ID NO 35
<211> LENGTH: 36
<212> TYPE: DNA
<213> ORGANISM: Artificial
<220> FEATURE:
<223> OTHER INFORMATION: Oligonucleotide primer

<400> SEQUENCE: 35
tataagcttg gggagaactc cttgggatac ttcctg                       36
```